US012692484B2

(12) United States Patent
Boghospor et al.

(10) Patent No.: US 12,692,484 B2
(45) Date of Patent: Jul. 28, 2026

(54) PUMA1 POLYMERASES AND USES THEREOF

(71) Applicant: 10x Genomics, Inc., Pleasanton, CA (US)

(72) Inventors: Lorita Boghospor, Lathrop, CA (US); Yufeng Qian, Union City, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 301 days.

(21) Appl. No.: 18/448,548

(22) Filed: Aug. 11, 2023

(65) Prior Publication Data

US 2024/0101978 A1    Mar. 28, 2024

Related U.S. Application Data

(60) Provisional application No. 63/397,638, filed on Aug. 12, 2022.

(51) Int. Cl.
| | |
|---|---|
| *C12N 9/12* | (2006.01) |
| *C12N 15/63* | (2006.01) |
| *C12Q 1/6844* | (2018.01) |

(52) U.S. Cl.
CPC ........... *C12N 9/1252* (2013.01); *C12N 15/63* (2013.01); *C12Q 1/6844* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 4,318,846 | A | 3/1982 | Khanna et al. |
| 4,683,195 | A | 7/1987 | Mullis et al. |
| 4,683,202 | A | 7/1987 | Mullis |
| 4,757,141 | A | 7/1988 | Fung et al. |
| 4,800,159 | A | 1/1989 | Mullis et al. |
| 4,849,336 | A | 7/1989 | Miyoshi et al. |
| 4,965,188 | A | 10/1990 | Mullis et al. |
| 5,066,580 | A | 11/1991 | Lee |
| 5,091,519 | A | 2/1992 | Cruickshank |
| 5,151,507 | A | 9/1992 | Hobbs et al. |
| 5,188,934 | A | 2/1993 | Menchen |
| 5,192,782 | A | 3/1993 | Djuric et al. |
| 5,198,537 | A | 3/1993 | Huber et al. |
| 5,344,757 | A | 9/1994 | Holtke et al. |
| 5,354,657 | A | 10/1994 | Boehringer et al. |
| 5,366,860 | A | 11/1994 | Bergot et al. |
| 5,512,462 | A | 4/1996 | Cheng |
| 5,599,675 | A | 2/1997 | Brenner |
| 5,635,352 | A | 6/1997 | Urdea et al. |
| 5,688,648 | A | 11/1997 | Mathies |
| 5,695,940 | A | 12/1997 | Drmanac et al. |
| 5,702,888 | A | 12/1997 | Holtke et al. |
| 5,750,341 | A | 5/1998 | Macevicz |
| 5,800,996 | A | 9/1998 | Lee et al. |

| | | | |
|---|---|---|---|
| 5,847,162 | A | 12/1998 | Lee et al. |
| 5,990,479 | A | 11/1999 | Weiss et al. |
| 6,172,218 | B1 | 1/2001 | Brenner |
| 6,207,392 | B1 | 3/2001 | Weiss et al. |
| 6,251,303 | B1 | 6/2001 | Bawendi et al. |
| 6,265,552 | B1 | 7/2001 | Schatz |
| 6,306,597 | B1 | 10/2001 | Macevicz |
| 6,319,426 | B1 | 11/2001 | Bawendi et al. |
| 6,322,901 | B1 | 11/2001 | Bawendi et al. |
| 6,423,551 | B1 | 7/2002 | Weiss et al. |
| 6,426,513 | B1 | 7/2002 | Bawendi et al. |
| 6,444,143 | B2 | 9/2002 | Bawendi et al. |
| 6,534,266 | B1 | 3/2003 | Singer |
| 6,576,291 | B2 | 6/2003 | Bawendi et al. |
| 6,969,488 | B2 | 11/2005 | Bridgham et al. |
| 7,057,026 | B2 | 6/2006 | Barnes et al. |
| 7,255,994 | B2 | 8/2007 | Lao |
| 7,345,159 | B2 | 3/2008 | Ju et al. |
| 7,473,767 | B2 | 1/2009 | Dimitrov |
| 7,534,991 | B2 | 5/2009 | Miller et al. |
| 7,544,794 | B1 | 6/2009 | Benner |
| 7,555,155 | B2 | 6/2009 | Levenson et al. |
| 7,566,537 | B2 | 7/2009 | Balasubramanian et al. |
| 7,655,898 | B2 | 2/2010 | Miller |
| 7,893,227 | B2 | 2/2011 | Wu et al. |

(Continued)

FOREIGN PATENT DOCUMENTS

| | | |
|---|---|---|
| WO | WO 2017/143155 | 8/2017 |
| WO | WO 2018/026873 | 2/2018 |

(Continued)

OTHER PUBLICATIONS

Chica et al. Curr Opin Biotechnol. Aug. 2005;16(4):378-84. (Year: 2005).*

Singh et al. Curr Protein Pept Sci. 2017, 18, 1-11 (Year: 2017).*

Bornscheuer et al. Curr Protoc Protein Sci. Nov. 2011;Chapter 26:Unit26.7. (Year: 2011).*

Yoshikuni et al. Curr Opin Chem Biol. Apr. 2007; 11(2):233-9. (Year: 2007).*

Accession A0A5Q2WD83. Feb. 26, 2020 (Year: 2020).*

"Database accession No. A0A5Q2WD83," Retrieved from UNIPROT, https://www.uniprot.org/uniprotkb/A0A5Q2WD83. Retrieved Feb. 26, 2020.

"Database accession No. A0A7T8C2C7," Retrieved from UNIPROT, https://www.uniprot.org/uniprotkb/A0A7T8C2C7. Retrieved Jun. 2, 2021.

(Continued)

*Primary Examiner* — Christian L Fronda

(74) *Attorney, Agent, or Firm* — MORRISON & FOERSTER LLP

(57) ABSTRACT

The present disclosure relates in some aspects to recombinant polymerases, variant PumA1 polymerases, and compositions thereof. Also provided herein are methods of using the recombinant polymerases and/or variant PumA1 polymerases for nucleic acid amplification (e.g., rolling circle amplification). In some aspects, the compositions and methods disclosed herein provide more robust amplification (e.g., RCA) reactions for improved in vitro and in situ analysis.

20 Claims, 8 Drawing Sheets

Specification includes a Sequence Listing.

(56) References Cited

U.S. PATENT DOCUMENTS

| | | | |
|---|---|---|---|
| 7,910,304 B2 | 3/2011 | Drmanac | |
| 7,941,279 B2 | 5/2011 | Hwang et al. | |
| 7,989,166 B2 | 8/2011 | Koch et al. | |
| 8,124,751 B2 | 2/2012 | Pierce et al. | |
| 8,199,999 B2 | 6/2012 | Hoyt et al. | |
| 8,268,554 B2 | 9/2012 | Schallmeiner | |
| 8,330,087 B2 | 12/2012 | Domenicali | |
| 8,415,102 B2 | 4/2013 | Geiss et al. | |
| 8,431,691 B2 | 4/2013 | McKernan et al. | |
| 8,460,865 B2 | 6/2013 | Chee et al. | |
| 8,462,981 B2 | 6/2013 | Determan et al. | |
| 8,481,258 B2 | 7/2013 | Church et al. | |
| 8,519,115 B2 | 8/2013 | Webster et al. | |
| 8,551,710 B2 | 10/2013 | Bernitz et al. | |
| 8,562,989 B2 | 10/2013 | Jakobovits et al. | |
| 8,632,975 B2 | 1/2014 | Vander Horn et al. | |
| 8,658,361 B2 | 2/2014 | Wu et al. | |
| 8,771,950 B2 | 7/2014 | Church et al. | |
| 8,986,926 B2 | 3/2015 | Ferree et al. | |
| 9,201,063 B2 | 12/2015 | Sood et al. | |
| 9,217,178 B2 | 12/2015 | Fedurco et al. | |
| 9,273,349 B2 | 3/2016 | Nguyen et al. | |
| 9,371,563 B2 | 6/2016 | Geiss et al. | |
| 9,371,598 B2 | 6/2016 | Chee | |
| 9,376,717 B2 | 6/2016 | Gao et al. | |
| 9,541,504 B2 | 1/2017 | Hoyt | |
| 9,551,032 B2 | 1/2017 | Landegren et al. | |
| 9,624,538 B2 | 4/2017 | Church et al. | |
| 9,650,406 B2 | 5/2017 | Zhou et al. | |
| 9,714,446 B2 | 7/2017 | Webster et al. | |
| 9,714,937 B2 | 7/2017 | Dunaway | |
| 9,727,810 B2 | 8/2017 | Fodor et al. | |
| 9,778,155 B2 | 10/2017 | Gradinaru et al. | |
| 9,783,841 B2 | 10/2017 | Nolan et al. | |
| 9,909,167 B2 | 3/2018 | Samusik et al. | |
| 10,032,064 B2 | 7/2018 | Hoyt | |
| 10,059,990 B2 | 8/2018 | Boyden et al. | |
| 10,126,242 B2 | 11/2018 | Miller et al. | |
| 10,138,509 B2 | 11/2018 | Church et al. | |
| 10,179,932 B2 | 1/2019 | Church et al. | |
| 10,227,639 B2 | 3/2019 | Levner et al. | |
| 10,246,700 B2 | 4/2019 | Dunaway et al. | |
| 10,266,888 B2 | 4/2019 | Daugharthy et al. | |
| 10,267,808 B2 | 4/2019 | Cai | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,370,698 B2 | 8/2019 | Nolan et al. | |
| 10,415,080 B2 | 9/2019 | Dunaway et al. | |
| 10,457,980 B2 | 10/2019 | Cai et al. | |
| 10,465,235 B2 | 11/2019 | Gullberg et al. | |
| 10,494,662 B2 | 12/2019 | Church et al. | |
| 10,495,554 B2 | 12/2019 | Deisseroth et al. | |
| 10,501,777 B2 | 12/2019 | Beechem et al. | |
| 10,501,791 B2 | 12/2019 | Church et al. | |
| 10,510,435 B2 | 12/2019 | Cai et al. | |
| 10,526,649 B2 | 1/2020 | Chen et al. | |
| 10,545,075 B2 | 1/2020 | Deisseroth et al. | |
| 10,550,429 B2 | 2/2020 | Harada et al. | |
| 10,580,128 B2 | 3/2020 | Miller | |
| 10,640,816 B2 | 5/2020 | Beechem et al. | |
| 10,640,826 B2 | 5/2020 | Church et al. | |
| 10,669,569 B2 | 6/2020 | Gullberg et al. | |
| 10,746,981 B2 | 8/2020 | Tomer et al. | |
| 10,774,372 B2 | 9/2020 | Chee et al. | |
| 10,774,374 B2 | 9/2020 | Frisén et al. | |
| 10,794,802 B2 | 10/2020 | Gradinaru et al. | |
| 10,802,262 B2 | 10/2020 | Tomer et al. | |
| 10,815,519 B2 | 10/2020 | Husain et al. | |
| 10,829,814 B2 | 11/2020 | Fan et al. | |
| 10,844,426 B2 | 11/2020 | Daugharthy et al. | |
| 10,858,698 B2 | 12/2020 | Church et al. | |
| 10,872,679 B2 | 12/2020 | Cai et al. | |
| 10,964,001 B2 | 3/2021 | Miller | |
| 11,174,281 B1 | 11/2021 | Graham et al. | |
| 11,287,422 B2 | 3/2022 | Previte et al. | |
| 11,434,525 B2 | 9/2022 | Glezer | |
| 11,459,603 B2 | 10/2022 | Tyagi et al. | |
| 11,499,185 B2 | 11/2022 | Vijayan et al. | |
| 11,643,679 B2 | 5/2023 | Glezer et al. | |
| 11,999,999 B2 | 6/2024 | Ju et al. | |
| 12,116,626 B2* | 10/2024 | Shastry | C12Y 207/07007 |
| 12,319,956 B2* | 6/2025 | Wang | C12Q 1/6874 |
| 2002/0045045 A1 | 4/2002 | Adams et al. | |
| 2003/0017264 A1 | 1/2003 | Treadway et al. | |
| 2005/0100900 A1 | 5/2005 | Kawashima et al. | |
| 2006/0188901 A1 | 8/2006 | Barnes et al. | |
| 2006/0240439 A1 | 10/2006 | Smith et al. | |
| 2006/0281109 A1 | 12/2006 | Barr et al. | |
| 2007/0166705 A1 | 7/2007 | Milton et al. | |
| 2008/0096258 A1* | 4/2008 | Korfhage | C12Q 1/6846 |
| | | | 435/91.2 |
| 2009/0118128 A1 | 5/2009 | Liu et al. | |
| 2011/0059865 A1 | 3/2011 | Smith et al. | |
| 2011/0223585 A1 | 9/2011 | Gullberg et al. | |
| 2012/0270305 A1 | 10/2012 | Reed et al. | |
| 2013/0079232 A1 | 3/2013 | Kain et al. | |
| 2013/0260372 A1 | 10/2013 | Buermann et al. | |
| 2013/0288249 A1 | 10/2013 | Gullbert | |
| 2013/0323729 A1 | 12/2013 | Landegren et al. | |
| 2016/0024555 A1 | 1/2016 | Church et al. | |
| 2016/0108458 A1 | 4/2016 | Frei et al. | |
| 2016/0305856 A1 | 10/2016 | Boyden et al. | |
| 2016/0369329 A1 | 12/2016 | Cai et al. | |
| 2016/0376642 A1 | 12/2016 | Landegren et al. | |
| 2017/0009278 A1 | 1/2017 | Söderberg et al. | |
| 2017/0081489 A1 | 3/2017 | Rodriques et al. | |
| 2017/0101672 A1 | 4/2017 | Luo et al. | |
| 2017/0220733 A1 | 8/2017 | Zhuang et al. | |
| 2017/0253918 A1 | 9/2017 | Kohman | |
| 2018/0052081 A1 | 2/2018 | Kohman | |
| 2018/0080876 A1 | 3/2018 | Rockel et al. | |
| 2018/0208967 A1 | 7/2018 | Larman et al. | |
| 2018/0237864 A1 | 8/2018 | Imler et al. | |
| 2018/0320226 A1 | 11/2018 | Church et al. | |
| 2019/0017106 A1 | 1/2019 | Frisen et al. | |
| 2019/0032128 A1 | 1/2019 | Chen et al. | |
| 2019/0055594 A1* | 2/2019 | Samusik | C12Q 1/682 |
| 2019/0112599 A1 | 4/2019 | Church et al. | |
| 2019/0119735 A1 | 4/2019 | Deisseroth et al. | |
| 2019/0155835 A1 | 5/2019 | Daugharthy et al. | |
| 2019/0161796 A1 | 5/2019 | Hauling et al. | |
| 2019/0177718 A1 | 6/2019 | Church et al. | |
| 2019/0177800 A1 | 6/2019 | Boutet et al. | |
| 2019/0194709 A1 | 6/2019 | Church et al. | |
| 2019/0218608 A1 | 7/2019 | Daugharthy et al. | |
| 2019/0249248 A1 | 8/2019 | Beechem et al. | |
| 2019/0264270 A1 | 8/2019 | Zhuang et al. | |
| 2019/0271028 A1 | 9/2019 | Khafizov et al. | |
| 2019/0276881 A1 | 9/2019 | Zhuang et al. | |
| 2019/0339203 A1 | 11/2019 | Miller et al. | |
| 2019/0367969 A1 | 12/2019 | Belhocine | |
| 2020/0010891 A1 | 1/2020 | Beechem et al. | |
| 2020/0071751 A1 | 3/2020 | Daugharthy et al. | |
| 2020/0123597 A1 | 4/2020 | Daniel | |
| 2020/0140920 A1 | 5/2020 | Pierce et al. | |
| 2020/0224243 A1 | 7/2020 | Desai et al. | |
| 2020/0224244 A1 | 7/2020 | Nilsson et al. | |
| 2020/0239946 A1 | 7/2020 | Dewal | |
| 2020/0277671 A1* | 9/2020 | Kamtekar | C12Q 1/686 |
| 2020/0354774 A1 | 11/2020 | Church et al. | |
| 2020/0354782 A1 | 11/2020 | Dewal | |
| 2020/0362398 A1 | 11/2020 | Kishi et al. | |
| 2020/0393343 A1 | 12/2020 | Kennedy-Darling et al. | |
| 2021/0017587 A1 | 1/2021 | Cai et al. | |
| 2021/0115504 A1 | 4/2021 | Cai et al. | |
| 2021/0155909 A1 | 5/2021 | Ong et al. | |
| 2021/0238662 A1 | 8/2021 | Bava | |
| 2021/0238674 A1 | 8/2021 | Bava | |
| 2021/0254140 A1 | 8/2021 | Stahl et al. | |
| 2021/0262018 A1 | 8/2021 | Bava et al. | |
| 2021/0277460 A1 | 9/2021 | Bava | |
| 2021/0340618 A1 | 11/2021 | Kuhnemund et al. | |
| 2021/0340621 A1 | 11/2021 | Daugharthy et al. | |

(56) References Cited

U.S. PATENT DOCUMENTS

| | | |
|---|---|---|
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.

Capodieci et al., "Gene expression profiling in single cells within tissue," Nat Methods. (2005) 2(9): 663-5.

Chen et al., "RNA imaging. Spatially resolved, highly multiplexed RNA profiling in single cells," Science. (2015) 348(6233): aaa6090. 16 pgs.

Conze et al., "Single molecule analysis of combinatorial splicing," Nucleic Acids Res. (2010) 38(16): e163.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Han et al., "Improving protein solubility and activity by introducing small peptide tags designed with machine learning models," Metab Eng Commun. (2020) 11:e00138.

(56) References Cited

OTHER PUBLICATIONS

Henegariu et al., "Custom fluorescent-nucleotide synthesis as an alternative method for nucleic acid labeling," Nature Biotechnol. (2000) 18:345.

Henikoff et al., "Amino acid substitution matrices from protein blocks," Proc Natl Acad Sci USA. (1992) 89(22):10915-9.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Kimple et al., "Overview of affinity tags for protein purification," Curr Protoc Protein Sci. (2013) 73: 9.9.1-9.9.23.

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177): 1360-1363.

Lei et al., "Structure-function analysis of human glucose-6-phosphatase, the enzyme deficient in glycogen storage disease type 1a," J Biol Chem. (1995) 270(20):11882-6.

Levene et al. "Zero-mode waveguides for single-molecule analysis at high concentrations." science 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lundquist et al. "Parallel confocal detection of single molecules in real time." Optics letters 33.9 (2008): 1026-1028.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mitra et al., "Fluorescent in situ sequencing on polymerase colonies," Anal. Biochem. (2003) 320, 55-65.

Payne et al. "In situ genome sequencing resolves DNA sequence and structure in intact biological samples," Science. (2021) 371(6532): eaay3446. doi: 10.1126/science.aay3446. Epub Dec. 31, 2020.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Rouhanifard et al. "ClampFISH detects individual nucleic acid molecules using click chemistry-based amplification," Nat Biotechnol. (2018) 17 pages. doi: 10.1038/nbt.4286.

Shendure et al, "Accurate multiplex polony sequencing of an evolved bacterial genome," Science (2005) 309(5741); 1728-1732.

Stanton et al., "Isolation and Characterisation of the Bundooravirus Genus and Phylogenetic Investigation of the Salasmaviridae Bacteriophages," Viruses. (2021) 13(8):1557.

Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.

Wahlby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wetmur, "DNA Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.

Zhao et al., "Advances of multiplex and high throughput biomolecular detection technologies based on encoding microparticles," Sci China Chem. (2011) 54(8):1185.

Chen et al., "Efficient in situ barcode sequencing using padlock probe-based BaristaSeq," Nucleic Acids Res. (2018) 46(4): e22.

Sun et al., "Composite organic-inorganic nanoparticles as Raman labels for tissue analysis," Nano Lett. (2007) 7(2): 351-6.

* cited by examiner

| | protein expression |
|---|---|
| Lane 1 | |
| Lane 2 | Lysate |
| Lane 3 | Insoluble |
| Lane 4 | Soluble |
| Lane 5 | PEI supernatant |
| Lane 6 | PEI pellet |

| C-His/SET | |
|---|---|
| | 59.992 kDa |

| pre-cleavage MW | 80.307 kDa |
|---|---|
| post-cleavage MW | 67.691 kDa |

FIG. 2

Sensitivity (detected object density)

PUMA1 POLYMERASES AND USES THEREOF

CROSS-REFERENCE TO RELATED APPLICATIONS

This application claims priority to U.S. Provisional Patent Application No. 63/397,638, filed Aug. 12, 2022, entitled "PUMA1 POLYMERASES AND USES THEREOF," which is herein incorporated by reference in its entirety for all purposes.

INCORPORATION BY REFERENCE OF SEQUENCE LISTING

The present application is being filed along with a Sequence Listing in electronic format. The Sequence Listing is provided as a file entitled 202412016100SeqList.xml, created Aug. 8, 2023, which is 36,613 bytes in size. The information in the electronic format of the Sequence Listing is incorporated by reference in its entirety.

FIELD

The present disclosure relates in some aspects to compositions and methods of using recombinant PumA1 polymerases and variants thereof.

BACKGROUND

Rolling circle amplification (RCA) allows production of multiple copies of a circular nucleic acid template. Phi29 DNA polymerase is the current standard DNA polymerase used for rolling circle amplification. However, existing Phi29 DNA polymerases have can have limited thermostability and/or exhibit limited sensitivity in rolling circle amplification based-assays. Improved polymerases for rolling circle amplification are needed. Provided herein are compositions and methods that address such and other needs.

SUMMARY

Rolling circle amplification and other methods that benefit from high nucleic acid processivity such as multiplex displacement amplification are typically performed with Phi29 polymerase. Phi29 polymerase is a mesophilic DNA polymerase derived from the *Bacillus subtilis* phage Phi29. Phi29 polymerase has both a 3'-5' exonuclease activity and nucleic acid polymerization activity. RCA is useful for many types of assays reactions, including in situ analysis of biological samples for endogenous analyte detection at spatially localized positions in a biological sample. Such exemplary assays are important tools for understanding the molecular basis of the biology of cells and organisms, and also for assessment and/or treatment of diseases. In some cases, Phi29 polymerase has certain limitations, including limited thermostability, with an optimal reaction temperature of 30° C., which results in slower reaction kinetics, less amplification product, and greater heterogeneity and amplification bias, especially with DNA having high guanine/cytosine (G/C) content.

In some aspects, provided herein are novel recombinant polymerase polypeptides and variants of a PumA1 polymerase (or PumA1 Pol) derived from a PumA1 bacteriophage. In some cases, the recombinant polymerases and variant PumA1 polymerases are thermostable, provide a high yield of amplification products, and/or can be used in wider range of nucleic acid amplification methods or samples.

The present application provides recombinant polymerases comprising an amino acid sequence of a PumA1 polymerase or variant thereof. Phylogenetic investigation shows that the polymerase protein encoded by the PumA1 genome shares 58% sequence identity to the Phi29 polymerase (Phi29 Pol). The recombinant polymerases provided herein comprising a PumA1 polymerase or variant thereof are soluble and well-expressed. Moreover, the present application provides data demonstrating that recombinant polymerases comprising a PumA1 polymerase sequence have features advantageous for performing rolling circle amplification. Notably, the recombinant PumA1 polymerase polypeptides provided herein provide greater sensitivity than Phi29 in a rolling circle amplification assay (e.g., producing a higher number of detectable rolling circle amplification products under the same conditions). Also provided herein are PumA1 polymerase variants. In some aspects, the PumA1 polymerase variants exhibit enhanced thermostability relative to a reference polymerase (e.g., wherein the reference polymerase is a wild-type PumA1 polymerase or Phi29). The present application also provides nucleic acids (e.g., recombinant nucleic acids and vectors) encoding the recombinant polymerases or PumA1 variants, expression systems and methods for producing the recombinant polymerases or PumA1 variants, and methods and kits for using the recombinant polymerases comprising a PumA1 polymerase or variant thereof (e.g., for rolling circle amplification).

In some aspects, provided herein is an isolated recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2. In some embodiments, the isolated recombinant polymerase comprises one or more amino acid substitutions at one or more positions selected from among positions 545, 574, and 575 corresponding to the positions of the sequence set forth in SEQ ID NO:1. In any of the embodiments herein, the isolated recombinant polymerase may comprise one or more amino acid substitutions selected from the group consisting of I545E, A574S, and P575V, wherein the amino acid numbering corresponds to the positions of the sequence set forth in SEQ ID NO:1. In any of the embodiments herein, the isolated recombinant polymerase may comprise amino acid substitutions I545E, A574S, and P575V, wherein the amino acid numbering corresponds to the positions of the sequence set forth in SEQ ID NO: 1. In any of the embodiments herein, the isolated recombinant polymerase may comprise the sequence of amino acid residues 2-30 of SEQ ID NO:1. In any of the embodiments herein, the isolated recombinant polymerase may comprise an N-terminal deletion of the methionine residue at position 1, corresponding to the positions of the sequence set forth in SEQ ID NO:1.

In some aspects, provided herein is an isolated recombinant polymerase comprising the amino acid sequence set forth in SEQ ID NO:1. In some aspects, provided herein is an isolated recombinant polymerase comprising the amino acid sequence set forth in SEQ ID NO:2.

In some aspects, provided herein is an isolated recombinant polymerase comprising the amino acid sequence set forth in SEQ ID NO:10. In some aspects, provided herein is an isolated recombinant polymerase comprising the amino acid sequence set forth in SEQ ID NO: 11.

In any of the embodiments herein, the recombinant polymerase can further comprise a heterologous sequence. In any of the embodiments herein, the recombinant polymerase can comprise, from amino-terminus (N-terminus) to carboxy-terminus (C-terminus), the amino acid sequence having at least or about 90%, 95%, 96%, 97%, 98%, 99%, or 99.5% sequence identity to the sequence set forth in SEQ ID NO:1 or SEQ ID NO:2, and the heterologous sequence. In any of the embodiments herein, the recombinant polymerase can comprise, from N-terminus to C-terminus, the heterologous sequence and the amino acid sequence having at least or about 90%, 95%, 96%, 97%, 98%, 99%, or 99.5% sequence identity to the sequence set forth in SEQ ID NO:1 or SEQ ID NO: 2.

In some of any of the embodiments herein, the recombinant polymerase comprises an affinity tag, a linker, and/or a solubility tag. In any of the embodiments herein, the heterologous sequence can comprise a cleavable sequence. In any of the embodiments herein, the heterologous sequence can comprise an affinity tag selected from the group consisting of a poly histidine tag (His-tag), a glutathione-s-transferase (GST) tag, a maltose-binding protein (MBP) tag, a mutated dehalogenase (Halo) tag, a *Fasciola hepatica* 8-kDa antigen (Fh8) tag, a streptavidin-binding peptide (SBP) tag, and a Tamavidin tag. In some instances, the affinity tag is a His-tag.

In any of the embodiments herein, the heterologous sequence can comprise a solubility tag selected from the group consisting of thioredoxin (Trx) tag, a small ubiquitin modified (SUMO) tag, an IgG domain B1 of protein G (GB1) tag, and a solubility-enhancement tag (SET). In any of the embodiments herein, the solubility tag can be positioned between the affinity tag and the amino acid sequence having at least or about 90%, 95%, 96%, 97%, 98%, 99%, or 99.5% sequence identity to the sequence set forth in SEQ ID NO:1 or SEQ ID NO:2. In any of the embodiments herein, the solubility tag can be connected to the N-terminus of the amino acid sequence having at least or about 90%, 95%, 96%, 97%, 98%, 99%, or 99.5% sequence identity to the sequence set forth in SEQ ID NO: 1 or SEQ ID NO:2. In any of the embodiments herein, the affinity tag can be positioned between the solubility tag and the amino acid sequence having at least or about 90%, 95%, 96%, 97%, 98%, 99%, or 99.5% sequence identity to the sequence set forth in SEQ ID NO:1 or SEQ ID NO:2. In any of the embodiments herein, the solubility tag can be a SUMO tag. In any of the embodiments herein, the SUMO tag can comprise the sequence set forth in SEQ ID NO:6.

In any of the embodiments herein, the solubility tag can have a net negative charge at pH 7. In any of the embodiments herein, the solubility tag can have a net negative charge of at least or at least about −6, −10, −12, −14, −15, −16, −17, or −18 at pH 7. In any of the embodiments herein, the solubility tag can comprise at least 2, 3, 4, 5, 6, 7, 8, 9, 10, or more acidic amino acid residues. In any of the embodiments herein, the solubility tag can be between 5 and 20 amino acid residues in length. In any of the embodiments herein, the solubility tag can be between 5 and 12 amino acid residues in length. In any of the embodiments herein, the solubility tag can be a sequence $S(E/D)_n K_m (E/D)_p G$ (SEQ ID NO:12), wherein S is serine, (E/D) is aspartate or glutamate, K is lysine, G is glycine, n is 5 or 6, m is 1 or 0, and p is an integer between 2 and 6. In any of the embodiments herein, the solubility tag can be a sequence set forth in any one of SEQ ID NOs: 13-18. In any of the embodiments herein, the solubility tag can have the sequence set forth in SEQ ID NO: 14.

In any of the embodiments herein, the heterologous sequence can comprise a linker. In any of the embodiments herein, the linker can comprise one or more glycine and/or serine residues. In any of the embodiments herein, the linker can comprise a sequence selected from the group consisting of SEQ ID NOs: 19-26.

In any of the embodiments herein, the recombinant polymerase can comprise, from N-terminus to C-terminus, a poly histidine tag (His-tag), a linker, a SUMO tag, and the amino acid sequence having at least or about 90%, 95%, 96%, 97%, 98%, 99%, or 99.5% sequence identity to the sequence set forth in SEQ ID NO:1 or SEQ ID NO:2. In any of the embodiments herein, the recombinant polymerase can comprise, from N-terminus to C-terminus, the amino acid sequence having at least or about 90%, 95%, 96%, 97%, 98%, 99%, or 99.5% sequence identity to the sequence set forth in SEQ ID NO:1 or SEQ ID NO:2, a linker, a poly histidine tag (His-tag), and a solubility tag.

In any of the embodiments herein, the isolated recombinant polymerase can be at least 85%, at least 90%, or at least 95% soluble. In any of the embodiments herein, the apparent molecular weight of the recombinant polymerase determined by sodium dodecyl sulfate-polyacrylamide gel electrophoresis may be between about 55 kDa and about 80 kDa, or between about 60 and about 70 kDa.

In some aspects, provided herein is a variant PumA1 polymerase comprising one or more amino acid substitutions at one or more positions selected from among positions 545, 574, and 575 corresponding to the positions of the sequence set forth in SEQ ID NO:1. In some embodiments, the variant PumA1 polymerase comprises one or more amino acid substitutions selected from the group consisting of I545E, A574S, and P575V, wherein the amino acid numbering corresponds to the positions of the sequence set forth in SEQ ID NO:1. In any of the embodiments herein, the variant PumA1 polymerase can comprise amino acid substitutions I545E, A574S, and P575V, wherein the amino acid numbering corresponds to the positions of the sequence set forth in SEQ ID NO:1. In any of the embodiments herein, the variant PumA1 polymerase can comprise the sequence of amino acid residues 2-30 of SEQ ID NO:1. In any of the embodiments herein, the variant PumA1 polymerase can comprise the sequence of amino acid residues 2-100 of SEQ ID NO: 1. In any of the embodiments herein, the variant PumA1 polymerase can comprise the sequence of amino acid residues 2-150 of SEQ ID NO:1. In any of the embodiments herein, the variant PumA1 polymerase can comprise the sequence of amino acid residues 2-190 of SEQ ID NO:1. In any of the embodiments herein, the variant PumA1 polymerase can comprise an N-terminal deletion of the methionine residue at position 1, corresponding to the positions of the sequence set forth in SEQ ID NO:1.

In any of the embodiments herein, the variant PumA1 polymerase can comprise the amino acid sequence of SEQ ID NO: 10. In any of the embodiments herein, the variant PumA1 polymerase can comprise the amino acid sequence of SEQ ID NO:11.

In any of the embodiments herein, the variant PumA1 polymerase may exhibit an improved polymerization rate compared to a reference PumA1 polymerase at 42° C. In any of the embodiments herein, the variant PumA1 polymerase may generate a comparable density of detected rolling-circle amplification (RCA) products in an RCA reaction compared to a reference Phi29 polymerase. In any of the embodiments herein, the variant PumA1 polymerase may generates a higher signal intensity for an RCA product generated in an RCA reaction compared to a an RCA product generated by a reference PumA1 polymerase at 42° C.

In any of the embodiments herein, the variant PumA1 polymerase may be at least 85%, at least 90%, or at least 95% soluble. In any of the embodiments herein, the apparent molecular weight of the variant PumA1 polymerase determined by sodium dodecyl sulfate-polyacrylamide gel electrophoresis may be between about 55 kDa and about 80 kDa, or between about 60 and about 70 kDa.

In some aspects, provided herein is a composition comprising the recombinant polymerase of any one of claims or the variant PumA1 polymerase of any of the preceding embodiments. In some embodiments, the composition comprises no more than 105, no more than 104, no more than 103, no more than 102, or no more than 10 genome equivalents of bacterial or phage DNA per unit of recombinant polymerase.

In any of the embodiments herein, the composition may comprise between about 0.05 μM and about 1 μM of the recombinant polymerase or variant PumA1 polymerase. In any of the embodiments herein, the composition may comprise at least 1, 10, 50, or 100 μM of the recombinant polymerase or variant PumA1 polymerase. In any of the embodiments herein, the recombinant polymerase or variant PumA1 polymerase may be at least 85%, at least 90%, or at least 95% soluble in the composition. In any of the embodiments herein, the recombinant polymerase or variant PumA1 polymerase may be at least 85%, at least 90%, or at least 95% soluble in the composition at 20° C.

In any of the embodiments herein, the composition may have a pH of about 8.5. In any of the embodiments herein, the composition may comprise between about 5 mM and about 10 mM MgCl$_2$. In any of the embodiments herein, the composition may comprise between about 0.1 mM and about 0.2 mM dNTPs. In any of the embodiments herein, the composition may comprise between about 1 mM and about 4 mM DTT. In any of the embodiments herein, the composition may comprise about 2 mg/mL BSA. In any of the embodiments herein, the composition may comprise about 10 mM NH$_4$SO$_4$.

In any of the embodiments herein, the apparent molecular weight of the recombinant polymerase or variant PumA1 polymerase determined by sodium dodecyl sulfate-polyacrylamide gel electrophoresis is between about 55 kDa and about 80 kDa, or between about 60 and about 70 kDa.

In some aspects, provided herein is a polynucleotide encoding the recombinant polymerase of any or the variant PumA1 polymerase of any of the preceding embodiments. In some embodiments, the polynucleotide may have at least 90%, 95%, 96%, 97%, 98%, 99%, or 99.5% sequence identity to the nucleic acid sequence of SEQ ID NO:8 or SEQ ID NO:9.

In some aspects, provided herein is a recombinant nucleic acid molecule comprising the polynucleotide of any of the preceding claims. In any of the embodiments herein, the recombinant nucleic acid molecule can further comprise a transcription regulatory sequence operatively linked to the polynucleotide. In any of the embodiments herein, the transcription regulatory sequence can comprise a promoter selected from the group consisting of a bacterial promoter, a viral promoter, and a mammalian promoter.

In some aspects, provided herein is a vector comprising the polynucleotide or the recombinant nucleic acid molecule of any of the preceding embodiments. In any of the embodiments herein, the vector can be a plasmid, a phagemid, a viral vector, a cosmid, or a transposon.

In some aspects, provided herein is a recombinant expression system comprising the polynucleotide, the recombinant nucleic acid molecule, or the vector of any of the preceding embodiments. In any of the embodiments herein, the recombinant expression system may generate the recombinant polymerase or the variant PumA1 polymerase of any of the preceding embodiments. In any of the embodiments herein, the recombinant expression system may be a cell system or cell-free system. In any of the embodiments herein, the recombinant expression system may comprise one or more cell systems selected from the group consisting of a bacterial cell, a fungal cell, an insect cell, and a mammalian cell.

In any of the embodiments herein, the polynucleotide sequence encoding the recombinant polymerase or variant PumA1 polymerase can be codon-optimized for the recombinant expression system.

In some aspects, provided herein is a method for producing the recombinant polymerase of or the variant PumA1 polymerase of any of the preceding embodiments, the method comprising culturing a cell population comprising a polynucleotide encoding the recombinant polymerase or the variant PumA1 polymerase and isolating the recombinant polymerase or variant PumA1 polymerase from the cell population. In any of the preceding embodiments, the method can comprise inducing expression of the recombinant polymerase or the variant PumA1 polymerase. In any of the preceding embodiments, the recombinant polymerase or variant PumA1 polymerase can be isolated using the affinity tag. In any of the preceding embodiments, the method can comprise cleaving the heterologous sequence.

In some aspects, provided herein is a method for amplifying a DNA, the method comprising contacting a biological sample containing DNA to be amplified with the recombinant polymerase, the variant PumA1 polymerase, or the composition of any of the preceding embodiments. In some embodiments, the DNA is amplified by a rolling circle amplification (RCA). In any of the embodiments herein, the DNA can be amplified by an RCA in situ in the biological sample (e.g., at a location in the biological sample). In some embodiments, the biological sample is on a substrate.

In some aspects, provided herein is a method of performing a rolling circle amplification (RCA), the method comprising contacting a biological sample containing DNA to be amplified with the recombinant polymerase, the variant PumA1 polymerase, or the composition of any of the preceding embodiments. In some embodiments, the method comprises incubating the recombinant polymerase or composition and the biological sample.

In any of the embodiments herein, the recombinant polymerase or composition and the biological sample may be incubated at a temperature of at least or about 5° C., 10° C., 15° C., 20° C., 25° C., 30° C., 35° C., 40° C., 42° C., 45° C., or higher. In any of the embodiments herein, the recombinant polymerase may comprise amino acid substitutions I545E, A574S, and P575V, wherein the amino acid numbering corresponds to the positions of the sequence set forth in SEQ ID NO: 1, and the RCA is performed at a temperature of at least 42° C. In any of the embodiments herein, the method may result in an increased signal intensity for a detected RCA product compared to a reference RCA product produced using a reference polymerase. In some embodiments, the reference polymerase is a wild-type Phi29 polymerase. In some embodiments, the reference polymerase is a wild-type PumA1 polymerase. In any of the embodiments herein, the RCA can be performed for at least or about 15 minutes, 30 minutes, 45 minutes, 1 hour, 2 hours, 3 hours, 6 hours, 12 hours, or longer. In some of any of the embodiments herein, the RCA can be performed for no more than about 15 minutes, 30 minutes, 45 minutes, 1 hour, 2 hours, or 3 hours.

In any of the embodiments herein, the method can comprise detecting an RCA product generated by the RCA. In any of the embodiments herein, the detecting can comprise detecting a sequence in the RCA product. In any of the embodiments herein, the RCA product can be detected at a location in the biological sample. In any of the embodiments herein, the detecting can comprise: contacting the biological sample with one or more detectably-labeled probes that directly or indirectly bind to the one or more barcode sequences or complements thereof, and detecting signals associated with the one or more detectably-labeled probes. In any of the embodiments herein, the detecting can comprise: contacting the biological sample with one or more intermediate probes that directly or indirectly bind to the one or more barcode sequences or complements thereof, wherein the one or more intermediate probes are detectable using one or more detectably-labeled probes, and detecting signals associated with the one or more detectably-labeled probes. In any of the embodiments herein, the method can further comprise removing the one or more intermediate probes and/or the one or more detectably-labeled probes.

In any of the embodiments herein, the recombinant polymerase or the variant PumA1 polymerase may exhibit an average processivity of at least 10 kb, at least 20 kb, at least 30 kb, at least 40 kb, at least 50 kb, at least 60 kb, or at least 70 kb. In any of the embodiments herein, the recombinant polymerase or the variant PumA1 polymerase may have strand displacing activity. In any of the embodiments herein, the recombinant polymerase or variant PumA1 polymerase may exhibit a mean nucleotide polymerization rate of at least 1000 nucleotides (nt)/min, at least 1500 nt/min, at least 2000 nt/min, or at least 2280 nt/min. In any of the embodiments herein, the recombinant polymerase or variant PumA1 polymerase may exhibit a nucleic acid replication error rate of fewer than $10^{-5}$ errors/bp, fewer than $10^{-6}$ errors/bp, or fewer than $10^{-7}$ errors/bp. In any of the embodiments herein, the recombinant polymerase or the variant PumA1 polymerase may exonuclease activity. In any of the embodiments herein, the recombinant polymerase or the variant PumA1 polymerase may have reverse transcriptase activity. In any of the embodiments herein, the recombinant polymerase or variant PumA1 polymerase may produce at least 10%, at least 15%, at least 20%, at least 25%, or at least 30% more rolling circle amplification products than a reference Phi29 polymerase under the same reaction conditions.

In any of the embodiments herein, the method may comprise contacting the biological sample with a buffer. In any of the embodiments herein, the buffer can have a pH of about 8.5. In any of the embodiments herein, the buffer can comprise between about 5 mM and about 10 mM $MgCl_2$. In any of the embodiments herein, the buffer can comprise between about 0.1 mM and about 0.2 mM dNTPs. In any of the embodiments herein, the buffer can comprise between about 1 mM and about 4 mM DTT. In any of the embodiments herein, the buffer can comprise about 2 mg/mL BSA. In any of the embodiments herein, the buffer can comprise about 10 mM $NH_4SO_4$.

In some aspects, provided herein is a kit comprising the recombinant polymerase, the variant PumA1 polymerase, or the composition of any of the preceding embodiments. In some embodiments, the kit comprises one or more of: (a) dNTPs; (b) one or more di-cation; (c) reaction buffer; (d) a buffer for use with any of (a)-(c); and (e) instructions for performing rolling circle amplification using the recombinant polymerase, the variant PumA1 polymerase, or the composition. In any of the embodiments herein, the kit can further comprise one or more primers. In any of the embodiments herein, the kit can further comprise one or more circularizable probes. In any of the embodiments herein, the kit can be for amplification of nucleic acid. In any of the embodiments herein, the kit can further comprise a detection probe for detection of the amplified nucleic acid.

BRIEF DESCRIPTION OF THE DRAWINGS

The drawings illustrate certain features and advantages of this disclosure. These embodiments are not intended to limit the scope of the appended claims in any manner.

FIG. 2 depicts results from an SDS-PAGE comparing the heparin purification of N-His/SUMO or C-His/SET recombinant PumA1 polypeptides.

FIG. 5A shows results for the sensitivity of detected RCPs with respect to different RCA buffer formulations. FIG. 5B shows results for the signal intensity of detected RCPs with respect to different RCA buffer formulations.

DETAILED DESCRIPTION

Figure 1:
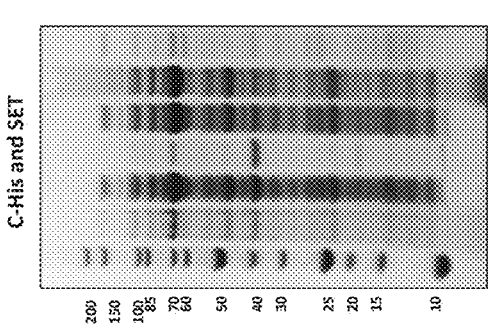
FIG. 1 depicts results from an SDS-PAGE comparing the protein solubility of a recombinant PumA1 polypeptide having an amino terminal polyhistidine/SUMO tag (N-His/Sumo) and a recombinant PumA1 polypeptide having a carboxy-terminal polyhistidine/SET tag (C-His/SET).
Figure 1:
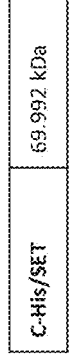
Figure 1:
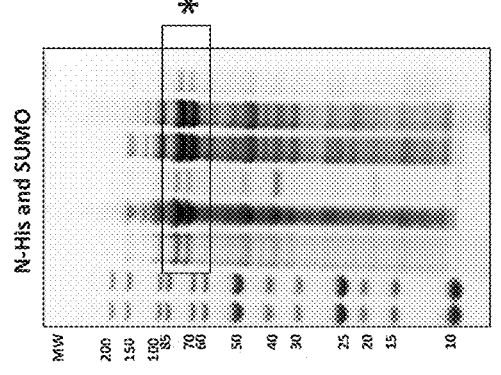

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. OVERVIEW

In some aspects, provided herein is a recombinant polymerase comprising an amino acid sequence of a PumA1 polymerase or variant thereof (e.g., an amino acid sequence having at least or about 90%, 95%, 96%, 97%, 98%, 99%, or 99.5% sequence identity to the sequence set forth in SEQ ID NO:1 or SEQ ID NO:2). In some embodiments, the recombinant polymerase comprises a heterologous sequence. In some cases, the heterologous sequence comprises a cleavable sequence. In some cases, the heterologous sequence remains part of the recombinant polymerase after purification (e.g., during nucleic acid amplification using the recombinant polymerase). In some embodiments, the heterologous sequence comprises an affinity tag. Exemplary affinity tags include but are not limited to a poly histidine tag (His-tag), a glutathione-s-transferase (GST) tag, a maltose-binding protein (MBP) tag, a mutated dehalogenase (Halo) tag, a *Fasciola hepatica* 8-kDa antigen (Fh8) tag, a streptavidin-binding peptide (SBP) tag, or a Tamavidin tag. In some instances, the affinity tag is a His-tag. In some cases, the heterologous sequence comprises a solubility tag. Exemplary solubility tags include but are not limited to a thioredoxin (Trx) tag, a small ubiquitin modified (SUMO) tag, an IgG domain B1 of protein G (GB1) tag, or a solubility-enhancement tag (SET). In some cases, the recombinant polymerase is at least 85%, at least 86%, at least 87%, at least 88%, at least 90%, or at least 95% soluble (e.g., at 20° C., 30° C., 35° C., 40° C., or 42° C.). In some aspects, the recombinant polymerase is functional in a nucleic acid amplification method (e.g., a rolling circle amplification). In some embodiments, the recombinant polymerase exhibits one or more improved features relative to a Phi29 polymerase in a method of rolling circle amplification, such as generating a higher number of RCA products using a similar amount of starting templates.

In some aspects, provided herein are PumA1 polymerases (e.g., recombinant PumA1 polymerases and/or variant PumA1 polymerases). In some aspects, the provided recombinant PumA1 polymerase or variant PumA1 polymerase comprises one or more mutations, such as amino acid substitutions, compared to a wild-type PumA1 polymerase. In some aspects, the provided variant PumA1 polymerases exhibit improved properties, such as improved activity, thermostability and/or processivity, compared to a wild-type Phi29 or PumA1 polymerase. In some aspects, the provided recombinant PumA1 polymerases exhibit improved properties, such as improved activity, thermostability and/or processivity, compared to a wild-type Phi29 polymerase. Also provided are related polynucleotides, recombinant nucleic acid molecules, vectors, recombinant expression systems, compositions, and methods for use and uses thereof.

In some aspects, the provided variant PumA1 polymerases exhibit one or more improved features or properties compared to a reference Phi29 or PumA1 polymerase, such as a wild-type Phi29 or PumA1 polymerase, respectively. In some aspects, the provided variant PumA1 polymerases exhibit one or more features, such as improved thermostability and improved processivity, for example, compared to a reference Phi29 or PumA1 polymerase such as a wild-type Phi29 or PumA1 polymerase, respectively. In some aspects, the provided variant PumA1 polymerases exhibit improved stability or activity, processivity, increased thermostability and/or yield, as compared to a reference Phi29 or PumA1 polymerase such as a wild-type Phi29 or PumA1 polymerase, respectively. In some aspects, the provided PumA1 polymerases (e.g., recombinant wild-type PumA1 polymerases) exhibit improved stability or activity, processivity, increased thermostability and/or yield, as compared to a reference Phi29 polymerase such as a wild-type Phi29.

In some aspects, the provided embodiments are based on an observation that in an exemplary PumA1 polymerase exhibited various improved properties for nucleic acid amplification, including improved thermostability at an elevated temperature (e.g., 37° C. or 42° C.), improved polymerization rate and increased rolling circle amplification (RCA) product generation, for example as observed by higher RCA product signal density, and/or signal intensity, compared to a wild-type Phi29 polymerase, in different types of assays and contexts for nucleic acid amplification, such as rolling circle amplification (RCA), both in in vitro assays and in situ assays.

In some aspects, the provided PumA1 polymerases can be used to improve nucleic acid amplification, such as in RCA, and result in improved analysis of biological samples, for example in RCA-based assays performed in solution (e.g., in vitro) or in situ in a biological sample such as a tissue sample or matrix-embedded biological sample.

II. RECOMBINANT POLYMERASES

Provided herein are recombinant polymerases comprising an amino acid sequence of a PumA1 polymerase or a variant or derivative thereof (e.g., an amino acid sequence having at least or about 90%, 95%, 96%, 97%, 98%, 99%, or 99.5% sequence identity to the sequence set forth in SEQ ID NO:1 or SEQ ID NO:2). Expression, purification, and functional characteristics of various exemplary recombinant polymerases comprising the amino acid sequence of SEQ ID NO:1 or SEQ ID NO:2 are provided in Examples 1-4. Provided herein are isolated and purified recombinant polymerases for performing an amplification reaction.

In some aspects, provided herein are variant PumA1 polymerases, such as PumA1 polymerases that comprise one or more variations or modifications compared to a wild-type or unmodified PumA1 polymerase. Characterization of an exemplary variant PumA1 polymerase demonstrating improved characteristics such as improved thermostability is provided in Example 7.

A. Recombinant and/or Variant Polymerases

In some embodiments, provided herein is a recombinant polymerase comprising an amino acid sequence having at least or about 90%, 95%, 96%, 97%, 98%, 99%, 99.2%, 99.4%, 99.5%, or 99.6% sequence identity to the sequence set forth in SEQ ID NO: 1 or SEQ ID NO:2. In some embodiments, the recombinant polymerase comprises the amino acid sequence set forth in SEQ ID NO:1. In some embodiments, the recombinant polymerase comprises the amino acid sequence set forth in SEQ ID NO:2. In some embodiments, the recombinant polymerase comprises the amino acid sequence of a wild-type PumA1 polymerase. In some embodiments, the recombinant polymerase comprises the amino acid sequence of a variant PumA1 polymerase disclosed herein.

In some embodiments, the recombinant polymerase further comprises one or more heterologous sequences. In some embodiments, the heterologous sequence comprises between 1 and 300, 2 and 250, 3 and 200, 4 and 150, 5 and 100, 10 and 90, 20 and 80, 30 and 70, or 40 and 60 amino acid residues. In some embodiments, the heterologous sequence comprises 1, 2, 3, 4, 5, 6, 7, 8, 9, 10, 20, 30, 40, 50, 60, 70, 80, 90, 100 or more amino acid residues, or a range defined by any of the foregoing. In some embodiments, the recombinant polymerase comprises two or more heterologous sequences. In some embodiments, the heterologous sequence is fused to the N- and/or C-terminal end of the amino acid sequence having at least or about 90%, 95%, 96%, 97%, 98%, 99%, 99.2%, 99.4%, 99.5%, or 99.6% sequence identity to the sequence set forth in SEQ ID NO:1 or SEQ ID NO:2, optionally via a linker. In some embodiments, the heterologous sequence is fused to the N-terminal end of amino acid sequence having at least or about 90%, 95%, 96%, 97%, 98%, 99%, 99.2%, 99.4%, 99.5%, or 99.6% sequence identity to the sequence set forth in SEQ ID NO:1 or SEQ ID NO:2, optionally via a linker. In some embodiments, the heterologous sequence is fused to the C-terminal end of the amino acid sequence having at least or about 90%, 95%, 96%, 97%, 98%, 99%, 99.2%, 99.4%, 99.5%, or 99.6% sequence identity to the sequence set forth in SEQ ID NO: 1 or SEQ ID NO:2, optionally via a linker. In some embodiments, a first heterologous sequence is fused to the N-terminal end of the amino acid sequence having at least or about 90%, 95%, 96%, 97%, 98%, 99%, 99.2%, 99.4%, 99.5%, or 99.6% sequence identity to the sequence set forth in SEQ ID NO: 1 or SEQ ID NO:2, and a second heterologous sequence is fused to the C-terminal end of the amino acid sequence having at least or about 90%, 95%, 96%, 97%, 98%, 99%, 99.2%, 99.4%, 99.5%, or 99.6% sequence identity to the sequence set forth in SEQ ID NO: 1 or SEQ ID NO:2 (optionally wherein the first and second heterologous sequences are different, and wherein the first and/or second heterologous sequences are optionally fused to the amino acid sequence via a linker). In some embodiments, the heterologous sequence comprises a cleavable sequence. Cleavable sequences are often cleaved, for example, by enzymatic or reductive mechanisms. Exemplary cleavable sequences include protease sensitive sequences, cyclopeptide sequences, and/or disulfide sensitive sequences. In some embodiments, the recombinant PumA1 polymerase (e.g., a recombinant wild-type PumA1 polymerase comprising the amino acid sequence of SEQ ID NO:1 or SEQ ID NO:2) or the variant PumA1 polymerase comprises two or more heterologous sequences. In some embodiments, the cleavable sequence is a SUMO tag.

In some embodiments, provided herein are variant PumA1 polymerases. In some aspects, a wild-type PumA1 polymerase is modified. In some embodiments, the variant PumA1 polymerase comprises one or more variations or modifications, e.g., amino acid substitutions, mutations, deletions, insertions, and/or fusions of additional peptide or protein sequences (e.g., for immobilizing the polymerase on a surface or otherwise tagging the polymerase enzyme), compared to the sequence of a reference PumA1 polymerase, such as a wild-type PumA1 polymerase. In some embodiments, provided herein is a variant PumA1 polymerase that exhibits improved thermostability relative to a wild-type PumA1 polymerase.

Also provided herein are compositions comprising any of the recombinant (e.g., wild-type) or variant PumA1 polymerases, polynucleotides encoding any of the recombinant or variant PumA1 polymerases, recombinant nucleic acid molecules encoding any of the recombinant or variant PumA1 polymerases or comprising any of the polynucleotides, vectors encoding any of the recombinant or variant PumA1 polymerases or comprising any of the polynucleotides, recombinant expression systems encoding any of the recombinant or variant PumA1 polymerases or comprising any of the polynucleotides and kits comprising or encoding any of the recombinant or variant PumA1 polymerases, and methods for use and uses of any of the foregoing.

In some aspects, provided herein are variant PumA1 polymerases comprising amino acid substitutions at one or more positions compared to a reference PumA1 polymerase. In some aspects, the reference PumA1 polymerase is a wild-type PumA1 polymerase. In some aspects, the reference PumA1 polymerase comprises the sequence set forth in SEQ ID NO:1.

In some aspects, corresponding positions of the one or more modifications, such as one or more substitutions, can be determined in reference to positions of a reference amino acid sequence or a reference nucleotide sequence. In some aspects, recitation that amino acid positions or nucleotide positions corresponding to amino acid positions or nucleotide positions in a disclosed sequence, such as a reference sequence set forth in the Sequence Listing, refers to amino acid positions or nucleotide positions identified upon alignment with the disclosed sequence based on structural sequence alignment or using a standard alignment algorithm, such as the GAP algorithm or other available algorithms. In general, to identify corresponding positions, the sequences of amino acids are aligned so that the highest order match is obtained. Alignment for determining corresponding positions can be obtained in various ways, for instance, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared. For example, corresponding residues can be determined by alignment of a reference sequence that is a wild-type PumA1 polymerase set forth in SEQ ID NO: 1 to a sequence of interest (e.g., a variant PumA1 polymerase sequence) by alignment methods available to one skilled in the art. By aligning the sequences (e.g., the reference sequence and the variant PumA1 polymerase sequence), one skilled in the art can identify corresponding residues, for example, using conserved and/or identical amino acid residues as guides.

In some aspects, the positions (e.g., amino acid residue numbers) of the one or more amino acid substitutions present in the variant PumA1 polymerase are described with reference to the corresponding position numbers or corresponding amino acid residue numbers of the reference PumA1 polymerase set forth in SEQ ID NO:1. In some aspects, the positions of the one or more substitutions are described with reference to the corresponding positions as set forth in SEQ ID NO:1, which includes the initial methionine residue at position 1. In some aspects, the positions of the one or more substitutions are described with reference to the positions as set forth in SEQ ID NO:2, which does not include an initial methionine residue. In some embodiments, position 545 (isoleucine, I545) of SEQ ID NO: 1 corresponds to position 544 (isoleucine, I544) of SEQ ID NO:2. In some embodiments, position 574 (alanine, A574) of SEQ ID NO: 1 corresponds to position 573 (alanine, A573) of SEQ ID NO:2. In some embodiments, position 575 (proline, P575) of SEQ ID NO: 1 corresponds to position 574 (proline, P574) of SEQ ID NO:2. In some aspects, the corresponding positions of the one or more substitutions, such as substitutions at positions corresponding to positions 1545, A574, and/or P575 with reference to SEQ ID NO:1, can be identified by available alignment methods. In some embodiments, the sequence set forth in SEQ ID NO: 1 is a wild-type PumA1 polymerase amino acid sequence, which includes an initial methionine residue at position 1, and the substitutions are present at positions corresponding to the described positions of SEQ ID NO:1. In some aspects, the corresponding positions of the one or more substitutions, such as substitutions at positions corresponding to positions I545, A574, and/or P575 with reference to SEQ ID NO:2, can be identified by available alignment methods. In some embodiments, the sequence set forth in SEQ ID NO:2 is a wild-type PumA1 polymerase amino acid sequence, which does not include an initial methionine residue, and the substitutions are present at positions corresponding to the described positions of SEQ ID NO:2.

In some aspects, the recombinant (e.g., wild-type) or variant PumA1 polymerase comprises a deletion or truncation. In some aspects, the recombinant or variant PumA1 polymerase comprises an N-terminal deletion or truncation. In some aspects, the recombinant or variant PumA1 polymerase comprises a C-terminal deletion or truncation.

In some embodiments, the recombinant or variant PumA1 polymerase comprises one or more substitutions and an N-terminal deletion or truncation of the methionine (M) residue at position 1, corresponding to the positions of the sequence set forth in SEQ ID NO:1. In some embodiments, the recombinant or variant PumA1 polymerase comprises one or more substitutions at positions corresponding to the positions of the sequence set forth in SEQ ID NO:2, which does not include the initial methionine (M) residue. In some embodiments, the variant PumA1 polymerase comprises one or more amino acid substitutions compared to the sequence set forth in SEQ ID NO: 2, with the one or more amino acid substitutions being at positions corresponding to at positions I544, A573, and/or P574 with reference to positions of SEQ ID NO:2. In some embodiments, the variant PumA1 polymerase comprises one or more amino acid substitutions compared to the sequence set forth in SEQ ID NO:2, with the one or more amino acid substitutions being at positions corresponding to at positions I544, A573, and/or P574 with reference to positions of SEQ ID NO:2. In some embodiments, the variant PumA1 polymerase comprises 2, 3, 4, 5, 6, 7, 8, 9, 10, or more amino acid substitutions compared to a reference PumA1 polymerase, e.g., wherein the reference sequence is the sequence set forth in SEQ ID NO:1 or SEQ ID NO:2. In some embodiments, the variant PumA1 polymerase comprises 2 amino acid substitutions compared to a reference PumA1 polymerase, e.g., wherein the reference sequence is the sequence set forth in SEQ ID NO:1 or SEQ ID NO: 2. In some embodiments, the variant PumA1 polymerase comprises 3 amino acid substitutions compared to a reference PumA1 polymerase, e.g., wherein the reference sequence is the sequence set forth in SEQ ID NO:1 or SEQ ID NO:2. In some embodiments, the variant PumA1 polymerase comprises 4 amino acid substitutions compared to a reference PumA1 polymerase, e.g., wherein the reference sequence is the sequence set forth in SEQ ID NO: 1 or SEQ ID NO:2. In some embodiments, the variant PumA1 polymerase comprises 5 amino acid substitutions compared to a reference PumA1 polymerase, e.g., wherein the reference sequence is the sequence set forth in SEQ ID NO: 1 or SEQ ID NO:2. In some embodiments, the variant PumA1 polymerase has at least or about 90%, 95%, 96%, 97%, 98%, 99%, 99.2%, 99.4%, 99.5%, or 99% sequence identity to the amino acid sequence set forth in SEQ ID NO:1 or SEQ ID NO:2.

In some embodiments, the variant PumA1 polymerase comprises one or more amino acid substitutions at positions selected from among 545, 574 and 575, corresponding to the positions of the sequence set forth in SEQ ID NO:1. In some embodiments, the variant PumA1 polymerase comprises one or more amino acid substitutions at positions selected from among 545 and 574, corresponding to the positions of the sequence set forth in SEQ ID NO:1. In some embodiments, the variant PumA1 polymerase comprises one or more amino acid substitutions at positions selected from among 545 and 575, corresponding to the positions of the sequence set forth in SEQ ID NO:1. In some embodiments, the variant PumA1 polymerase comprises one or more amino acid substitutions at positions selected from among 574 and 575, corresponding to the positions of the sequence set forth in SEQ ID NO:1.

In some embodiments, the variant PumA1 polymerase comprises one or more amino acid substitutions at positions selected from among 544, 573 and 574, corresponding to the positions of the sequence set forth in SEQ ID NO:2. In some embodiments, the variant PumA1 polymerase comprises one or more amino acid substitutions at positions selected from among 544 and 573, corresponding to the positions of the sequence set forth in SEQ ID NO:2. In some embodiments, the variant PumA1 polymerase comprises one or more amino acid substitutions at positions selected from among 544 and 574, corresponding to the positions of the sequence set forth in SEQ ID NO:2. In some embodiments, the variant PumA1 polymerase comprises one or more amino acid substitutions at positions selected from among 573 and 574, corresponding to the positions of the sequence set forth in SEQ ID NO:2.

In some aspects, where the position numbers are described with reference to the sequence set forth in SEQ ID NO:1, the corresponding positions can be determined using available alignment algorithms. In some aspects, where the position numbers are described with reference to the sequence set forth in SEQ ID NO:2, the corresponding positions can be determined using available alignment algorithms.

In some embodiments, provided herein are variant PumA1 polymerases comprising one or more amino acid substitutions, at positions corresponding to the positions of a reference PumA1 polymerase, such as a wild-type PumA1 polymerase sequence set forth in SEQ ID NO: 1. In some embodiments, provided herein are variant PumA1 polymerases comprising one or more amino acid substitutions, at positions corresponding to the positions of a reference PumA1 polymerase, such as a wild-type PumA1 polymerase sequence set forth in SEQ ID NO:2. In some embodiments, the variant PumA1 polymerase comprises an amino acid substitution at position 545, corresponding to the positions of the sequence set forth in SEQ ID NO:1. In some embodiments, the variant PumA1 polymerase comprises an amino acid substitution at position 544, corresponding to the positions of the sequence set forth in SEQ ID NO:2. In some embodiments, the variant PumA1 polymerase comprises an amino acid substitution at position 574, corresponding to the positions of the sequence set forth in SEQ ID NO:1. In some embodiments, the variant PumA1 polymerase comprises an amino acid substitution at position 573, corresponding to the positions of the sequence set forth in SEQ ID NO:2. In some embodiments, the variant PumA1 polymerase comprises an amino acid substitutions at position 575, corresponding to the positions of the sequence set forth in SEQ ID NO:1. In some embodiments, the variant PumA1 polymerase comprises an amino acid substitution at position 574, corresponding to the positions of the sequence set forth in SEQ ID NO: 2.

In some embodiments, the variant PumA1 polymerase comprises two or more amino acid substitutions, including amino acid substitutions at positions 545 and 574, corresponding to the positions of the sequence set forth in SEQ ID NO:1. In some embodiments, the variant PumA1 polymerase comprises two or more amino acid substitutions, including amino acid substitutions at positions 545 and 575, corresponding to the positions of the sequence set forth in SEQ ID NO:1. In some embodiments, the variant PumA1 polymerase comprises two or more amino acid substitutions, including amino acid substitutions at positions 574 and 575, corresponding to the positions of the sequence set forth in SEQ ID NO:1. In some embodiments, the variant PumA1 polymerase comprises three or more amino acid substitutions, including amino acid substitutions at positions 545, 574 and 575, corresponding to the positions of the sequence set forth in SEQ ID NO: 1.

In some embodiments, the variant PumA1 polymerase comprises an amino acid substitution at position 545, corresponding to the positions of the sequence set forth in SEQ ID NO: 1. In some embodiments, in a wild-type PumA1, the amino acid residue at position 545, corresponding to the positions of the sequence set forth in SEQ ID NO:1, is an isoleucine (I). In some aspects, in an exemplary variant PumA1 polymerase, the isoleucine at position 545, wherein the numbering is based on the positions in SEQ ID NO:1 (I545), is substituted with a different amino acid residue. In some embodiments, the amino acid substitution is a conservative substitution. In some embodiments, the amino acid substitution is a non-conservative substitution. In some embodiments, the amino acid substitution at position 545, wherein the numbering is based on the positions in SEQ ID NO: 1, is selected from among I545E, I545D, I545Q, I545V, I545A, and I545G. In some embodiments, the amino acid substitution at position 545 is I545E or I545D. In some embodiments, the amino acid substitution at position 545 is I545E (wherein the numbering is based on the positions in SEQ ID NO:1). In some embodiments, the variant PumA1 polymerase comprises a I545E amino acid substitution. In some embodiments, the amino acid substitution at position 545 is a conservative substitution of a substitution with glutamic acid (E). Exemplary conservative substitutions for E include, for example, D, Q, V, A, or G. In some embodiments, the amino acid substitution at position 545 is I545D. In some embodiments, the variant PumA1 polymerase further comprises one or more amino acid substitutions other than at position 545, corresponding to the positions of the sequence set forth in SEQ ID NO:1, and/or one or more other modifications.

In some embodiments, the variant PumA1 polymerase comprises an amino acid substitution at position 574, corresponding to the positions of the sequence set forth in SEQ ID NO: 1. In some embodiments, the sequence set forth in SEQ ID NO: 1 is the wild-type PumA1 amino acid sequence. In some embodiments, in a wild-type PumA1, the amino acid residue at position 574, corresponding to the positions of the sequence set forth in SEQ ID NO:1, is an alanine (A). In some aspects, in an exemplary variant PumA1 polymerase, the alanine at position 574, wherein the numbering is based on the positions in SEQ ID NO:1 (A574) is substituted with a different amino acid residue. In some embodiments, the amino acid substitution is a conservative substitution. In some embodiments, the amino acid substitution is a non-conservative substitution. In some embodiments, the amino acid substitution at position 574 is selected from the among A574S, A574C, A574N, A574P, A574T, A574W, and A574Y. In some embodiments, the amino acid substitution at position 574 is A574S or A574T. In some embodiments, the amino acid substitution at position 574 is A574S. In some embodiments, the variant PumA1 polymerase comprises a A574S amino acid substitution. In some embodiments, the amino acid substitution at position 574 is a conservative substitution of a substitution with serine(S). Exemplary conservative substitutions for S include, for example, A, C, N, P, T, W, or Y. In some embodiments, the amino acid substitution at position 574 is A574T. In some embodiments, the variant PumA1 polymerase further comprises one or more amino acid substitutions other than at position 574, corresponding to the positions of the sequence set forth in SEQ ID NO:1, and/or one or more other modifications.

In some embodiments, the variant PumA1 polymerase comprises an amino acid substitution at position 575, corresponding to the positions of the sequence set forth in SEQ ID NO: 1. In some embodiments, in a wild-type PumA1, the amino acid residue at position 575, corresponding to the positions of the sequence set forth in SEQ ID NO:1, is a proline (P). In some aspects, in an exemplary variant PumA1 polymerase, the proline at position 575, wherein the numbering is based on the positions in SEQ ID NO:1 (P575) is substituted with a different amino acid residue. In some embodiments, the amino acid substitution is a conservative substitution. In some embodiments, the amino acid substitution is a non-conservative substitution. In some embodiments, the amino acid substitution at position 575 is, for example, P575V, P575D, P575E, P575I, P575L, or P575M. In some embodiments, the amino acid substitution at position 575 is P575V, P575I, or P575L. In some embodiments, the amino acid substitution at position 575 is P575V. In some embodiments, the variant PumA1 polymerase comprises a P575V amino acid substitution. In some embodiments, the amino acid substitution at position 575 is a conservative substitution of a substitution with valine (V). Exemplary conservative substitutions for V include, for example, D, E, I, L, or M. In some embodiments, the amino acid substitution at position 575 is P575I. In some embodiments, the amino acid substitution at position 575 is P575L. In some embodiments, the variant PumA1 polymerase further comprises one or more amino acid substitutions other than at position 575, corresponding to the positions of the sequence set forth in SEQ ID NO:1, and/or one or more other modifications.

In some embodiments, the variant PumA1 polymerase comprises amino acid substitutions at one or more positions selected from among positions 545 and 574, corresponding to the positions of the sequence set forth in SEQ ID NO:1. In some embodiments, the variant PumA1 polymerase comprises amino acid substitutions at positions 545 and 574, corresponding to the positions of the sequence set forth in SEQ ID NO:1. In some embodiments, in a wild-type PumA1, the amino acid residue at position 545, corresponding to the positions of the sequence set forth in SEQ ID NO:1, is an isoleucine (I) and the amino acid residue at position 574, corresponding to the positions of the sequence set forth in SEQ ID NO:1, is an alanine (A). In some aspects, in an exemplary variant PumA1 polymerase, the isoleucine at position 545 (I545) and the alanine at position 574 (A574) are substituted with different amino acid residues, such as any substitutions described herein. In some embodiments, the amino acid substitution at position 545 is, for example, I545E, I545D, I545Q, I545V, I545A, or I545G, and the amino acid substitution at position 574 is, for example, A574S, A574A, A574C, A574N, A574P, A574T, A574W, or A574Y. In some embodiments, the amino acid substitution at position 545 is I545E or I545D, and the amino acid substitution at position 574 is A574S or A574T. In some embodiments, the amino acid substitution at position 545 is I545E, and the amino acid substitution at position 574 is A574S. In some embodiments, the variant PumA1 polymerase comprises I545E and A574S amino acid substitutions. In some embodiments, the amino acid substitutions at positions 545 and 574 are I545E and A574S, respectively. In some embodiments, the variant PumA1 polymerase further comprises one or more amino acid substitutions other than at positions 545 and 574, corresponding to the positions of the sequence set forth in SEQ ID NO:1, and/or one or more other modifications.

In some embodiments, the variant PumA1 polymerase further comprises an amino acid substitution at position 575, corresponding to the positions of the sequence set forth in SEQ ID NO:1. In some embodiments, the variant PumA1 polymerase comprises amino acid substitutions at positions 545 and 575, corresponding to the positions of the sequence set forth in SEQ ID NO:1. In some embodiments, in a wild-type PumA1, the amino acid residue at position 545, corresponding to the positions of the sequence set forth in SEQ ID NO:1, is an isoleucine (I) and the amino acid residue at position 575, corresponding to the positions of the sequence set forth in SEQ ID NO:1, is a proline (P). In some aspects, in an exemplary variant PumA1 polymerase, the isoleucine at position 545 (I545) and the proline at position 575 (P575) are substituted with different amino acid residues, such as any substitutions described herein. In some embodiments, the amino acid substitution at position 545 is, for example, I545E, I545D, I545Q, I545V, I545A, or I545G, and the amino acid substitution at position 575 is, for example, P575V, P575D, P575E, P575I, P575L, or P575M. In some embodiments, the amino acid substitution at position 545 is I545E or I545D, and the amino acid substitution at position 575 is P575V, P575I, or P575L. In some embodiments, the amino acid substitution at position 545 is I545E, and the amino acid substitution at position 575 is P575V. In some embodiments, the variant PumA1 polymerase comprises I545E and P575V amino acid substitutions. In some embodiments, the amino acid substitutions at positions 545 and 575 are I545E and P575V, respectively. In some embodiments, the variant PumA1 polymerase further comprises one or more amino acid substitutions other than at positions 545 and 575, corresponding to the positions of the sequence set forth in SEQ ID NO:1, and/or one or more other modifications.

In some embodiments, the variant PumA1 polymerase comprises amino acid substitutions at positions 574 and 575, corresponding to the positions of the sequence set forth in SEQ ID NO:1. In some embodiments, in a wild-type PumA1, the amino acid residue at position 574, corresponding to the positions of the sequence set forth in SEQ ID NO:1, is an alanine (A) and the amino acid residue at position 575, corresponding to the positions of the sequence set forth in SEQ ID NO:1, is a proline (P). In some aspects, in an exemplary variant PumA1 polymerase, the alanine at position 574 (A574) and the proline at position 575 (P575) are substituted with different amino acid residues, such as any described herein. In some embodiments, the amino acid substitution at position 574 is, for example, A574S, A574A, A574C, A574N, A574P, A574T, A574W, or A574Y, and the amino acid substitution at position 575 is, for example, P575V, P575D, P575E, P575I, P575L, or P575M. In some embodiments, the amino acid substitution at position 574 is A574S or A574T, and the amino acid substitution at position 575 is P575V, P575I, or P575L. In some embodiments, the amino acid substitution at position 574 is A574S, and the amino acid substitution at position 575 is P575V. In some embodiments, the variant PumA1 polymerase comprises A574S and P575V amino acid substitutions. In some embodiments, the amino acid substitutions at positions 574 and 575 are A574S and P575V, respectively. In some embodiments, the variant PumA1 polymerase further comprises one or more amino acid substitutions other than at positions 574 and 575, corresponding to the positions of the sequence set forth in SEQ ID NO:1, and/or one or more other modifications. In some embodiments, the variant PumA1 polymerase has at least or about 90%, 95%, 96%, 97%, 98%, 99%, or 99.5% sequence identity to the amino acid sequence set forth in SEQ ID NO:10.

In some embodiments, the variant PumA1 polymerase comprises amino acid substitutions at positions 545, 574, and 575, corresponding to the positions of the sequence set forth in SEQ ID NO:1. In some embodiments, in a wild-type PumA1, the amino acid residue at position 545, corresponding to the positions of the sequence set forth in SEQ ID NO:1, is an isoleucine (I), the amino acid residue at position 574, corresponding to the positions of the sequence set forth in SEQ ID NO:1, is an alanine (A), and the amino acid residue at position 575, corresponding to the positions of the sequence set forth in SEQ ID NO:1, is a proline (P). In some aspects, in an exemplary variant PumA1 polymerase, the isoleucine at position 545 (I545), the alanine at positon 574 (A574), and the proline at position 575 (P575) are substituted with different amino acid residues, such as any substitutions described herein. In some embodiments, the amino acid substitution at position 545 is, for example, I545E, I545D, I545Q, I545V, I545A, or I545G, the amino acid substitution at position 574 is, for example, A574S, A574A, A574C, A574N, A574P, A574T, A574W, or A574Y, and the amino acid substitution at position 575 is, for example, P575V, P575D, P575E, P575I, P575L, or P575M. In some embodiments, the amino acid substitution at position 545 is I545E or I545D, the amino acid substitution at position 574 is A574S or A574T, and the amino acid substitution at position 575 is P575V, P575I, or P575L. In some embodiments, the amino acid substitution at position 545 is I545E, the amino acid substitution at position 574 is A574S, and the amino acid substitution at position 575 is P575V. In some embodiments, the variant PumA1 polymerase comprises I545E, A574S, and P575V amino acid substitutions. In some embodiments, the amino acid substitutions at positions 545, 574, and 575 are I545E, A574S, and P575V, respectively. In some embodiments, the variant PumA1 polymerase has at or about or at least at or about 90%, 95%, 96%, 97%, 98%, 99%, or 99.5% sequence identity to the amino acid sequence set forth in SEQ ID NO:10. In some embodiments, the variant PumA1 polymerase comprises the amino acid sequence set forth in SEQ ID NO:10. In some embodiments, the variant PumA1 polymerase consists of the amino acid sequence set forth in SEQ ID NO:10.

In some aspects, amino acid sequence variants of a PumA1 polymerase may be prepared by introducing appropriate modifications into the nucleotide sequence encoding the wild-type PumA1 polymerase, or by peptide synthesis. Exemplary of modifications or variations include, deletions from, and/or insertions into and/or substitutions of residues within the amino acid sequences of the wild-type PumA1 polymerase.

Variants of a PumA1 polymerase may also be prepared by inserting or deleting one or more amino acids in reference to the sequence set forth in SEQ ID NO: 1 or SEQ ID NO:2. The variant PumA1 polymerase may include any combination of modifications or variations, such as insertion, deletion, and substitutions, including any combinations of modifications or variations described herein or with any known modifications or variations. In some aspects, the variant PumA1 polymerase possesses improved activity and/or properties, such as any described herein (e.g., improved thermostability). In some aspects, such modifications or variations can be used to improve aspects of protein production or altering one or more properties of the polymerase, such as to achieve the improved activity and/or properties.

Exemplary amino acid sequence insertions include N-and/or C-terminal fusions ranging in length from one amino acid to polypeptides containing a hundred or more amino acids, as well as internal insertions of single or multiple amino acids. Examples of terminal fusions include the addition of affinity tags, linkers, and/or solubility domains. Exemplary tags include purification, substrate binding, or other tags, such as a polyhistidine tag, a His10 tag, a His6 tag, an alanine tag, an Ala10 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an hemagglutinin (HA) tag, a DSB (Sso7D) tag, a lysine tag, a NanoTag, a Cmyc tag. Exemplary linkers include poly amino acid linkers, such as those that are rich in amino acids glycine, serine, alanine, histidine, arginine, lysine, glutamine and/or proline. Other polypeptide domains that can be fused at the N- and/or C-terminal include domains from polypeptides or proteins such as an antibody or antibody domain, antibody fragment, antigen, receptor, receptor domain, receptor fragment, binding protein, or ligand.

In some aspects, the variant PumA1 polymerase includes one or more deletions. In some aspects, deletions may include deletion of N- and/or C-terminal amino acids, as well as internal amino acids, with deletions ranging from a single amino acid to a hundred or more amino acids.

In some aspects, the variant PumA1 polymerase, such as any of those comprising one or more amino acid substitution described herein, further comprises one or more heterologous sequences. In some embodiments, the heterologous sequence comprises between 1 and 300, 2 and 250, 3 and 200, 4 and 150, 5 and 100, 10 and 90, 20 and 80, 30 and 70, or 40 and 60 amino acid residues. In some embodiments, the heterologous sequence comprises 1, 2, 3, 4, 5, 6, 7, 8, 9, 10, 20, 30, 40, 50, 60, 70, 80, 90, 100 or more amino acid residues, or a range defined by any of the foregoing. In some embodiments, the variant PumA1 polymerase comprises two or more heterologous sequences.

In some embodiments, the heterologous sequence is fused to the N- and/or C-terminal end of the variant PumA1 polymerase. In some embodiments, the heterologous sequence is fused to the N-terminal end of the variant PumA1 polymerase. In some embodiments, the heterologous sequence is fused to the C-terminal end of the variant PumA1 polymerase. In some embodiments, a first heterologous sequence is fused to the N-terminal end of the variant PumA1 polymerase, and a second heterologous sequence is fused to the C-terminal end of the variant PumA1 polymerase (optionally wherein the first and second heterologous sequences are different). In some embodiments, the heterologous sequence comprises a cleavable sequence. Cleavable sequences are often cleaved, for example, by enzymatic or reductive mechanisms. Exemplary cleavable sequences include protease sensitive sequences, cyclopeptide sequences, and/or disulfide sensitive sequences. In some embodiments, the variant PumA1 polymerase comprises two or more heterologous sequences. In some embodiments, the cleavable sequence is a SUMO tag.

In some embodiments, the recombinant polymerase or variant PumA1 polymerase comprises a heterologous sequence. In some cases, the heterologous sequence comprises a tag. In some aspects, the tag is a tag for purification, substrate binding, or other tags. In some embodiments, the tag is selected from among a poly histidine (HIS) tag, a solubility enhancement tag (SET), a small ubiquitin modified (SUMO) tag, a *Fasciola hepatica* 8-kDa antigen (Fh8) tag, a thioredoxin (Trx) tag, a glutathione-s-transferase (GST) tag, a maltose-binding protein (MBP) tag, an IgG domain B1 of protein G (GB1) tag, a mutated dehalogenase (Halo) tag, a streptavidin-binding peptide (SBP) tag, and a Tamavidin tag. In some aspects, exemplary tags include those described in, for example, Kimple et al., Curr Protoc Protein Sci. 2013; 73: Unit-9.9. In some embodiments, the tag is a SUMO tag. In some embodiments, the tag comprises an amino acid sequence set forth in SEQ ID NO:6. In some embodiments, the tag is a poly HIS tag. In some embodiments, the tag comprises an amino acid sequence set forth in SEQ ID NO:5.

In some embodiments, the tag is between 1 and 50, 2 and 40, 3 and 30, 5 and 20, 5 and 12, or 8 and 20 amino acid residues in length.

In some embodiments, the tag is a solubility enhancement tag (SET). In some embodiments, the tag has a net negative charge at pH 7. In some embodiments, the tag comprising a negative charge improves the variant PumA1 polymerase solubility and/or stability. In some embodiments, the tag has a net negative charge of at least or at least about −1, −2, −4, −6, −10, −12, −14, −15, −16, −17, or −18. In some embodiments, the tag has a net negative charge of −1, −2, −4, −6, −10, −12, −14, −15, −16, −17, or −18. In some embodiments, the tag comprises one or more acidic amino acid residue, for example, an aspartic acid (Asp, D) and/or a glutamic acid (Glu, E). In some embodiments, the tag comprises at least 2, 3, 4, 5, 6, 7, 8, 9, 10, or more acidic amino acid residues. In some embodiments, the tag is between 1 and 50, 2 and 40, 3 and 30, 5 and 20, 5 and 12, or 8 and 20 amino acid residues in length. In some embodiments, the tag has a sequence $S(E/D)_nK_m(E/D)_pG$ (SEQ ID NO:12), wherein S is serine, (E/D) is aspartate or glutamate, K is lysine, G is glycine, n is 5 or 6, m is 1 or 0, and p is an integer between 2 and 6. In some embodiments, the tag comprises a sequence set forth in any one of SEQ ID NOs: 13-18. In some embodiments, the tag comprises the sequence set forth in SEQ ID NO:14. In some embodiments, the tag is operably linked to the C-terminus of the recombinant polymerase or variant PumA1 polymerase.

In some embodiments, the recombinant polymerase comprises, from amino-terminus (N-terminus) to carboxy-terminus (C-terminus), an amino acid sequence having at least or about 90%, 95%, 96%, 97%, 98%, 99%, or 99.5% sequence identity to the sequence set forth in SEQ ID NO:1 or SEQ ID NO:2, and a heterologous sequence. In some embodiments, the recombinant polymerase comprises, from N-terminus to C-terminus, an amino acid sequence having at least or about 90%, 95%, 96%, 97%, 98%, 99%, or 99.5% sequence identity to the sequence set forth in SEQ ID NO:1 or SEQ ID NO:2, an affinity tag, and a solubility tag. In some embodiments, the recombinant polymerase comprises, from N-terminus to C-terminus, an amino acid sequence having at least or about 90%, 95%, 96%, 97%, 98%, 99%, or 99.5% sequence identity to the sequence set forth in SEQ ID NO:1 or SEQ ID NO:2, a polyhistidine (HIS) tag, and a solubility tag. In some embodiments, the polyhistidine tag comprises 4, 6, or 8 histidines. In some embodiments, the polyhistidine tag comprises 6 histidines. In some embodiments, the solubility tag comprises a sequence S(E/D)$_n$K$_m$(E/D)$_p$G (SEQ ID NO:12), wherein S is serine, (E/D) is aspartate or glutamate, K is lysine, G is glycine, n is 5 or 6, m is 1 or 0, and p is an integer between 2 and 6. In some embodiments, the solubility tag comprises a sequence set forth in any one of SEQ ID NOs: 13-18. In some embodiments, the solubility tag comprises the sequence set forth in SEQ ID NO:14. In some cases, the amino acid sequence having at least or about 90%, 95%, 96%, 97%, 98%, 99%, or 99.5% sequence identity to the sequence set forth in SEQ ID NO:1 or SEQ ID NO:2 comprises one or more amino acid substitutions at one or more positions selected from among positions 545, 574, and 575 corresponding to the positions of the sequence set forth in SEQ ID NO:1. In some cases, the more amino acid substitutions are selected from the group consisting of I545E, A574S, and P575V, wherein the amino acid numbering corresponds to the positions of the sequence set forth in SEQ ID NO: 1. In some cases, the one or more amino acid substitutions are I545E, A574S, and/or P575V, wherein the amino acid numbering corresponds to the positions of the sequence set forth in SEQ ID NO: 1. In some embodiments, the recombinant polymerase further comprises a linker sequence (e.g., a serine and/or glycine linker sequence), which is optionally positioned between the affinity tag and the amino acid sequence having at least or about 90%, 95%, 96%, 97%, 98%, 99%, or 99.5% sequence identity to the sequence set forth in SEQ ID NO:1 or SEQ ID NO:2. In some cases, the recombinant polymerase comprises an amino acid sequence having at least or about 90%, 95%, 96%, 97%, 98%, 99%, or 99.5% sequence identity to the sequence set forth in SEQ ID NO:7.

In some embodiments the recombinant polymerase comprises, from N-terminus to C-terminus, a heterologous sequence and an amino acid sequence having at least or about 90%, 95%, 96%, 97%, 98%, 99%, or 99.5% sequence identity to the sequence set forth in SEQ ID NO:1 or SEQ ID NO:2. In some embodiments the recombinant polymerase comprises, from N-terminus to C-terminus, an affinity tag, a solubility tag, and an amino acid sequence having at least or about 90%, 95%, 96%, 97%, 98%, 99%, or 99.5% sequence identity to the sequence set forth in SEQ ID NO: 1 or SEQ ID NO:2. In some embodiments, the solubility tag is a SUMO tag. In some cases, the solubility tag comprises the amino acid sequence of SEQ ID NO:6. In some cases, the amino acid sequence having at least or about 90%, 95%, 96%, 97%, 98%, 99%, or 99.5% sequence identity to the sequence set forth in SEQ ID NO:1 or SEQ ID NO:2 comprises one or more amino acid substitutions at one or more positions selected from among positions 545, 574, and 575 corresponding to the positions of the sequence set forth in SEQ ID NO:1. In some cases, the more amino acid substitutions are selected from the group consisting of I545E, A574S, and P575V, wherein the amino acid numbering corresponds to the positions of the sequence set forth in SEQ ID NO: 1. In some cases, the one or more amino acid substitutions are I545E, A574S, and/or P575V, wherein the amino acid numbering corresponds to the positions of the sequence set forth in SEQ ID NO: 1. In some cases, the heterologous sequence is removed after cleavage of the heterologous sequence (e.g., cleavage of the SUMO tag). In some cases, prior to cleavage, the recombinant polymerase comprises an amino acid sequence having at least or about 90%, 95%, 96%, 97%, 98%, 99%, or 99.5% sequence identity to the sequence set forth in SEQ ID NO:3. In some cases, after cleavage, the recombinant polymerase comprises an amino acid sequence having at least or about 90%, 95%, 96%, 97%, 98%, 99%, or 99.5% sequence identity to the sequence set forth in SEQ ID NO: 2.

In some embodiments, the heterologous sequence comprises a linker. In some embodiments, the linker comprises one or more glycine, serine, alanine, histidine, arginine, lysine, glutamine and/or proline residues. In some embodiments, the linker comprises one or more glycine and/or serine residues. In some embodiments, the linker is 1, 2, 3, 4, 5, 6, 7, 8, 9, 10, or more amino acid residues, or a range defined by any of the foregoing, in length. In some embodiments, the linker is between 1 and 30, 2 and 25, 3 and 20, 4 and 18, 5 and 16, 6 and 14, 7 and 12, or 8 and 10 amino acid residues in length. In some embodiments, the linker comprises the sequence set forth in any one of SEQ ID NOS: 19-26. In some embodiments, the linker comprises the sequence SSG, set forth in SEQ ID NO:4. In some embodiments, the linker comprises 2, 3, 4, 5, 6, or more repeats of any one of the sequences set forth in SEQ ID NOS: 19-26.

In some embodiments, the recombinant polymerase or the variant PumA1 polymerase comprises two or more linkers. In some embodiments, a linker is fused to the N- and/or C-terminal end of the recombinant polymerase or the variant PumA1 polymerase. In some embodiments, the linker sequence comprises a cleavable linker. Cleavable linkers are often cleaved, for example, by enzymatic or reductive mechanisms. Exemplary cleavable linkers include protease sensitive linkers, cyclopeptide linkers, and/or disulfide sensitive linkers. In some embodiments, the linker may be fused directly to the N- and/or C-terminal end of the recombinant polymerase or the variant PumA1 polymerase (e.g., to the N- and/or C-terminal end of the amino acid sequence that has at least or about 90%, 95%, 96%, 97%, 98%, 99%, 99.2%, 99.4%, 99.5%, or 99% sequence identity to the amino acid sequence set forth in any one of SEQ ID NOs: 1, 2, 10, or 11).

In any of the embodiments herein, the recombinant polymerase or the variant PumA1 polymerase may comprise the sequence of amino acid residues 2-30, 2-50, 2-100, 2-200, 2-300, 2-400, or 2-500 of SEQ ID NO:1. In any of the embodiments herein, the recombinant polymerase or the variant PumA1 polymerase may comprise the sequence of amino acid residues 2-150, 2-180, 2-190, or 2-200 of SEQ ID NO:1. In some embodiments, the recombinant polymerase or the variant PumA1 polymerase comprises the sequence of amino acid residues 2-540 of SEQ ID NO: 1. In some embodiments, the recombinant polymerase or the variant PumA1 polymerase comprises the sequence of amino acid residues 2-100 of SEQ ID NO:1.

In some aspects, provided are compositions comprising a recombinant polymerase or variant PumA1 polymerase disclosed herein, such as those comprising one or more amino acid substitution, insertion, and/or deletion, as described herein. In some aspects, the composition comprises a recombinant variant PumA1 polymerase comprising one or more heterologous sequences. In some embodiments, the composition has a purity of at least 70%, 75%, 80%, 85%, 90%, 95%, 96%, 97%, 98%, 99% or 99.5% with respect to the recombinant variant PumA1 polymerase. In some aspects, at least 70%, 75%, 80%, 85%, 90%, 95%, 96%, 97%, 98%, 99% or 99.5% of the biomolecules present in the composition is a recombinant variant PumA1 polymerase. In some aspects, at least 70%, 75%, 80%, 85%, 90%, 95%, 96%, 97%, 98%, 99% or 99.5% of the polypeptides or proteins of the composition is a recombinant variant PumA1 polymerase. In some aspects, the composition comprising the recombinant variant PumA1 polymerase has a high level of purity and/or is nearly pure with respect to other biomolecules present in the composition, for example, other polypeptides, proteins, amino acids, nucleotides or polynucleotides. In some aspects, biomolecules other than recombinant variant PumA1 polymerases may be considered contaminants within the composition. In some embodiments, the composition has less than at or about 30%, 25%, 20%, 15%, 10%, 5%, 4%, 3%, 2%, 1% or 0.5% contaminants.

B. Exemplary Features

In some aspects, the provided PumA1 polymerases, such as wild-type or those comprising one or more amino acid substitution, insertion, and/or deletion, exhibits one or more improved features or properties. These features or properties relate to the activity and function of a nucleic acid polymerase, such as, but not limited, DNA amplification. An exemplary improved feature may be related to the polymerase activity, performance, robustness, utility, or a combination thereof. Exemplary improved features (e.g., improved thermostability) of the provided PumA1 polymerases relate to, for example, thermostability, processivity, and polymerization rate. In some cases, an improved polymerization rate may be a slower polymerization rate compared to a reference polymerase (e.g., wild-type Phi29). In some cases, an improved polymerization rate may be a faster polymerization rate compared to a reference polymerase (e.g., wild-type Phi29). Other exemplary features may relate to increased yield, altered cofactor selectivity, exonuclease deficiency, and increased resistance to photodamage. In some aspects, the provided PumA1 polymerases exhibit improved thermostability, processivity, or polymerization rate, or that otherwise exhibit an improved ability to read through damaged, modified, or other difficult stretches of nucleic acid template, can be employed for precision amplification applications (e.g., RCA). In some embodiments, improved activity may be the production of more amplified DNA compared to a reference polymerase (e.g., wild-type Phi29). In some embodiments, improved activity may be the production of less amplified DNA compared to a reference polymerase (e.g., wild-type Phi29). In some aspects, the PumA1 polymerase has strand displacing activity. In some aspects, the PumA1 polymerase has exonuclease activity. In some aspects, the PumA1 polymerase has reverse transcriptase activity. In some embodiments, the one or more feature is of a variant PumA1 polymerase improved compared to a reference PumA1 polymerase (e.g., wild-type PumA1 polymerase). In some embodiments, the one or more feature is of a recombinant wild-type PumA1 polymerase compared to a reference polymerase (e.g., wild-type Phi29). In some embodiments, the one or more feature is assayed under the same conditions using a comparable amount of the reference polymerase. Improvements in one or more feature support an expanded application and/or utility of the variant PumA1 polymerase, for example for DNA amplification and/or sequencing. In some embodiments, the provided PumA1 polymerase possesses one or more feature resulting in improved nucleic acid amplification from a biological sample and/or nucleic acid amplification methods such as a rolling circle amplification (RCA).

1. Improved Thermostability

In some embodiments, the PumA1 polymerase described herein (e.g., recombinant wild-type PumA1 polymerase or variant PumA1 polymerase) exhibits improved thermostability. In some aspects, the improved thermostability includes improved polymerase activity. In some embodiments, the improved thermostability includes improved, more rapid, more robust, and/or more accurate polymerase activity, for example at elevated temperatures. In some embodiments, the PumA1 polymerase exhibiting improved thermostability can be used for a nucleic acid amplification reaction, such as a DNA amplification reaction. In some embodiments, the variant PumA1 polymerase is used in a nucleic acid amplification performed at a temperature of or about 5° C., 10° C., 15° C., 20° C., 25° C., 30° C., 35° C., 40° C., 42° C., 45° C., or higher. In some embodiments, the PumA1 polymerase is used in a nucleic acid amplification performed between at or about 5° C. and 50° C., 10° C. and 42° C., 10° C. and 45° C., 25° C. and 42° C., 25° C. and 45° C., 30° C. and 42° C., 30° C. and 45° C., 35° C. and 42° C., or 35° C. and 45° C. In some embodiments, the PumA1 polymerase is used in a nucleic acid amplification performed at an elevated temperature. In some embodiments, the PumA1 polymerase is used in a nucleic acid amplification performed at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C. or higher. In some embodiments, the PumA1 polymerase is used in a nucleic acid amplification performed between at or about 30° C. and 50° C., 32° C. and 48° C., 34° C. and 46° C., 36° C. and 44° C., or 38° C. and 42° C. In some embodiments, the PumA1 polymerase is used in a nucleic acid amplification performed at or about 42° C.

In some embodiments, the provided PumA1 polymerases (e.g., recombinant wild-type PumA1 polymerase or variant PumA1 polymerase), for example, those described in Section II.A, exhibit improved thermostability. In some aspects, a variant PumA1 polymerase exhibiting improved thermostability comprises one or more amino acid substitutions at one or more positions selected from among positions 545, 574, and 575 corresponding to the positions of the sequence set forth in SEQ ID NO:1. In some embodiments, the variant PumA1 polymerase exhibiting improved thermostability further comprises one or more amino acid substitutions other than at positions 545, 574, and 575. In some embodiments, the variant PumA1 polymerase exhibiting improved thermostability has at or about or at least at or about 90%, 95%, 96%, 97%, 98%, 99%, or 99.5% sequence identity to the amino acid sequence set forth in SEQ ID NO:10. In some embodiments, the variant PumA1 polymerase exhibiting improved thermostability comprises the amino acid sequence set forth SEQ ID NOS: 10. In some embodiments, the variant PumA1 polymerase exhibiting improved thermostability has at or about or at least at or about 90%, 95%, 96%, 97%, 98%, 99%, or 99.5% sequence identity to the amino acid sequence set forth in SEQ ID NO:11. In some embodiments, the variant PumA1 polymerase exhibiting improved thermostability comprises the amino acid sequence set forth SEQ ID NO:11.

In some embodiments, the provided PumA1 polymerases (e.g., recombinant wild-type PumA1 polymerase or variant PumA1 polymerase) produce more amplified DNA compared to a reference polymerase. In some embodiments, the provided variant PumA1 polymerases produce more amplified DNA at elevated temperatures compared to a reference PumA1 polymerase. In some embodiments, the provided recombinant wild-type PumA1 polymerases produce more amplified DNA at elevated temperatures compared to a reference Phi29 polymerase. In some embodiments, the increase in nucleic acid amplification and the generation of amplified nucleic acid product are measured or assessed using a fluorescent dye. Exemplary fluorescent dyes for measuring the increase in nucleic acid amplification and the generation of amplified nucleic acid product, such as in an RCA reaction, include any described herein. In some embodiments, the PumA1 polymerase produces at or about or more than at or about 1%, 5%, 10%, 15%, 20%, 25%, 30%, 40%, 50%, 75%, 100%, 150%, or 200% more amplified DNA compared to a reference polymerase. In some embodiments, the PumA1 polymerase produces between 10% and 200%, 25% and 175%, 50% and 150%, 75% and 125%, 90% and 110%, or 95% and 105% more amplified DNA compared to a reference polymerase.

In some embodiments, the PumA1 polymerase (e.g., recombinant wild-type PumA1 polymerase or variant PumA1 polymerase) produces more amplified DNA compared to a reference polymerase, such that the polymerization reaction time can be reduced, the amount of input template DNA can be reduced, the product signal from the increased DNA yield is increased, or a combination thereof. In some embodiments, the polymerization reaction time can be reduced by at or about or at least at or about 5%, 10%, 15%, 20%, 25%, 30%, 40%, 50%, or 75% using a provided variant PumA1 polymerase compared to a reference PumA1 polymerase. In some embodiments, the polymerization reaction time can be reduced by at or about or at least at or about 5%, 10%, 15%, 20%, 25%, 30%, 40%, 50%, or 75% using a provided recombinant wild-type PumA1 polymerase compared to a reference Phi-29 polymerase. In some embodiments, the required input template DNA can be reduced by at or about or at least at or about 5%, 10%, 15%, 20%, 25%, 30%, 40%, 50%, or 75% using a provided variant PumA1 polymerase compared to a reference PumA1 polymerase or using a provided recombinant wild-type PumA1 polymerase compared to a reference Phi-29 polymerase. In some embodiments, the signal from the increased DNA yield is increased by at or about or at least at or about 1%, 5%, 10%, 15%, 20%, 25%, 30%, 40%, 50%, 75%, 100%, 150%, or 200% using a provided variant PumA1 polymerase compared to a reference PumA1 polymerase or using a provided recombinant wild-type PumA1 polymerase compared to a reference Phi-29 polymerase. In some embodiments, the improved thermostability of the provided PumA1 polymerase results in increased DNA amplification and DNA yield at temperatures, including but not limited to a temperature of at or about 5° C., 10° C., 15° C., 20° C., 25° C., 30° C., 35° C., 40° C., 45° C., or higher. In some embodiments, the improved thermostability of the provided PumA1 polymerase results in increased DNA amplification and DNA yield at elevated temperatures, including but not limited to a temperature of at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the provided PumA1 polymerases amplify nucleic acids, e.g., DNA, faster compared to a reference polymerase. In some embodiments, the provided variant PumA1 polymerases amplify nucleic acids faster at elevated temperatures compared to a reference PumA1 polymerase. In some embodiments, the provided recombinant wild-type PumA1 polymerases amplify nucleic acids faster at elevated temperatures compared to a reference Phi29 polymerase. In some embodiments, the increase in the rate of nucleic acid amplification is measured or assessed using a fluorescent dye. Exemplary fluorescent dyes for measuring the total product and rate of nucleic acid amplification, such as in an RCA reaction, include any described herein. In some embodiments, the recombinant wild-type PumA1 polymerase amplifies nucleic acids, e.g., DNA, at a polymerization rate (e.g., nucleic acids, e.g., DNA, signal per unit of time) of at or about or at least at or about 1%, 5%, 10%, 15%, 20%, 25%, 30%, 40%, 50%, 75%, 100%, 150%, or 200% greater compared to a reference Phi29 polymerase. In some embodiments, the variant PumA1 polymerase amplifies nucleic acids, e.g., DNA, at a polymerization rate (e.g., nucleic acids, e.g., DNA, signal per unit of time) of at or about or at least at or about 1%, 5%, 10%, 15%, 20%, 25%, 30%, 40%, 50%, 75%, 100%, 150%, or 200% greater compared to a reference PumA1 polymerase. In some embodiments, the variant PumA1 polymerase produces between 10% and 200%, 25% and 175%, 50% and 150%, 75% and 125%, 90% and 110%, or 95% and 105% more amplified DNA in a unit of time compared to a reference PumA1 polymerase. For example, a provided PumA1 polymerase produces between 100% and 200% more amplified nucleic acids, e.g., DNA, in 1 hour compared to a reference polymerase. In some embodiments, the provided PumA1 polymerase amplifies nucleic acids, e.g., DNA, faster for at least 1, 2, 3, 4, 6, 8, 10, 12 hours or more compared to a reference polymerase.

In some aspects, the polymerization rate of a polymerase is the speed at which the polymerase is able to catalyze nucleotide incorporation into a growing polynucleotide strand during nucleic acid amplification, which can be described as the number of nucleotide bases incorporated per units of time (e.g., bases/second). The polymerization rate is dependent on different reaction conditions including temperature, buffer composition, substrate, substrate concentration, and time. In some embodiments, the provided PumA1 polymerase (e.g., recombinant wild-type PumA1 polymerase or variant PumA1 polymerase) described herein exhibits improved polymerization rate. In some embodiments, the wild-type PumA1 polymerase or variant PumA1 polymerase exhibits improved polymerization rate compared to a reference Phi29 polymerase or wild-type PumA1 polymerase, respectively. In some embodiments, the provided PumA1 polymerase (e.g., recombinant wild-type PumA1 polymerase or variant PumA1 polymerase) is used for a nucleic acid amplification process.

In some embodiments, the provided recombinant wild-type PumA1 polymerase produces more amplified nucleic acid compared to a reference Phi29 polymerase. In some embodiments, the nucleic acid amplification is a RCA reaction. In some embodiments, the provided recombinant wild-type polymerase generates a higher density of detected RCA products in an RCA reaction compared to a reference Phi29 polymerase. In some embodiments, the provided recombinant wild-type PumA1 polymerase generates a higher product signal intensity in an RCA reaction compared to a reference Phi29 polymerase.

In some embodiments, the provided variant PumA1 polymerase produces more amplified nucleic acid compared to a reference PumA1 polymerase. In some embodiments, the nucleic acid amplification is a RCA reaction. In some embodiments, the provided variant PumA1 polymerase generates a higher density of detected RCA products in an RCA reaction compared to a reference PumA1 polymerase. In some embodiments, the provided variant PumA1 polymerase generates a higher product signal intensity in an RCA reaction compared to a reference PumA1 polymerase.

In some embodiments, the provided PumA1 polymerase (e.g., recombinant wild-type PumA1 polymerase or variant PumA1 polymerase) produce amplified nucleic acids, e.g., DNA, at a faster rate compared to a reference polymerase, such that the polymerization reaction time can be reduced and/or the product signal from the increased nucleic acids, e.g., DNA, amplification is increased. In some embodiments, the polymerization reaction time can be reduced by at or about or at least at or about 5%, 10%, 15%, 20%, 25%, 30%, 40%, 50%, or 75% using a provided variant PumA1 polymerase compared to a reference PumA1 polymerase or using a provided recombinant wild-type PumA1 polymerase compared to a reference Phi-29 polymerase. In some embodiments, the amount of produced nucleic acid, e.g., DNA, or the yield of reaction product is increased at or about or at least at or about 1%, 5%, 10%, 15%, 20%, 25%, 30%, 40%, 50%, 75%, 100%, 150%, or 200% using a provided variant PumA1 polymerase compared to a reference PumA1 polymerase or using a provided recombinant wild-type PumA1 polymerase compared to a reference Phi-29 polymerase. In some embodiments, the improved thermostability of the variant PumA1 polymerase results in increased rate of nucleic acids amplification at a particular temperature, including but not limited to, at or about 5° C., 10° C., 15° C., 20° C., 25° C., 30° C., 35° C., 40° C., 45° C., or higher. In some embodiments, the improved thermostability of the variant PumA1 polymerase results in increased rate of nucleic acid amplification at an elevated temperature, including but not limited to, at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In some embodiments, the provided PumA1 polymerase (e.g., recombinant wild-type PumA1 polymerase or variant PumA1 polymerase) are used to amplify nucleic acids, e.g., DNA, using a particular method, such as in a rolling-circle amplification (RCA) reaction. In some embodiments, the provided variant PumA1 polymerases generate a higher density of detected rolling-circle amplification (RCA) products in an RCA reaction compared to a reference PumA1 polymerase. In some embodiments, the provided recombinant wild-type PumA1 polymerases generate a higher density of detected rolling-circle amplification (RCA) products in an RCA reaction compared to a reference Phi29 polymerase. In some embodiments, determining the density of detected RCA products (RCPs) involves the use and detection of a specific fluorescent dye, wherein the density of detected RCA products is measured in RCA product counts per $\mu m^2$ sample area. In some embodiments, the density of detected RCPs is related to the total sample signal. In some embodiments, the provided PumA1 polymerase generates a higher density of detected RCPs in an RCA reaction compared to a reference polymerase. In some embodiments, the provided PumA1 polymerases produce a density of detected RCA products that is at or about or at least at or about 1%, 5%, 10%, 15%, 20%, 25%, 30%, 40%, 50%, 75%, 100%, 150%, or 200% higher compared to a reference polymerase. In some embodiments, the provided PumA1 polymerases produce a density of detected RCA products that is between 10% and 200%, 25% and 175%, 50% and 150%, 75% and 125%, 90% and 110%, or 95% and 105% higher compared to a reference polymerase.

In some embodiments, the RCA reaction is assessed or evaluated for generated RCA product signal intensity. In some aspects, the product signal intensity is calculated as a local signal intensity over a local background mean intensity. In some embodiments, the provided variant PumA1 polymerases generate a higher product signal intensity in an RCA reaction compared to a reference PumA1 polymerase. In some embodiments, the provided PumA1 polymerases produce an RCA reaction product signal intensity at or about or at least at or about 1%, 5%, 10%, 15%, 20%, 25%, 30%, 40%, 50%, 75%, 100%, 150%, or 200% higher compared to a reference polymerase. In some embodiments, the provided PumA1 polymerases produce a RCA reaction product signal intensity at least between 10% and 200%, 25% and 175%, 50% and 150%, 75% and 125%, 90% and 110%, or 95% and 105% higher compared to a reference polymerase.

In some embodiments, an RCA reaction using the provided variant PumA1 polymerases is performed at a temperature of or about 5° C., 10° C., 15° C., 20° C., 25° C., 30° C., 35° C., 40° C., 45° C., or higher. In some embodiments, the RCA reaction is performed between 5° C. and 50° C., 10° C. and 45° C., 25° C. and 45° C., 30° C. and 45° C., or 35° C. and 45° C. In some embodiments, the RCA reaction using the provided PumA1 polymerases (e.g., recombinant wild-type PumA1 polymerase or variant PumA1 polymerase) is performed at an elevated temperature. In some embodiments, the RCA reaction is performed at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C. In some embodiments, the RCA reaction is performed between 30° C. and 50° C., 32° C. and 48° C., 34° C. and 46° C., 36° C. and 44° C., or 38° C. and 42° C.

2. Other Exemplary Features

In some aspects, the provided recombinant and/or variant PumA1 polymerases exhibit other features or improvements, for example, related to the polymerase activity and applications in analyzing or assessing biological samples, such as in nucleic acid amplifications and sequencing. Examples of other improved or altered properties and features include improved or altered processivity, polymerization rate, product yield, increased half-life, cofactor selectivity, exonuclease activity, and/or strand displacing activity. The provided recombinant and/or variant PumA1 polymerases can also exhibit two or more of the altered features in combination, or also possess additional improved or altered properties. In some aspects, the variant PumA1 polymerase has strand displacing activity. In some embodiments, the features or improvements exhibited by the provided recombinant and/or variant PumA1 polymerases are related to the polymerase activity in biological samples, such as a tissue sample or a section of a cell pellet or cell block.

In some aspects, polymerase processivity is the ability of a nucleic acid polymerase to carry out continuous nucleic acid synthesis on a template nucleic acid without frequent dissociation. Processivity can be measured by the average number of nucleotides incorporated by a nucleic acid polymerase on a single association-disassociation event. In any of the embodiments herein, the recombinant polymerase or the variant PumA1 polymerase may exhibit an average processivity of at least 10 kb, at least 20 kb, at least 30 kb, at least 40 kb, at least 50 kb, at least 60 kb, or at least 70 kb. In some embodiments, a recombinant and/or variant PumA1 polymerase described herein exhibits improved processivity relative to a reference polymerase, wherein the improved processivity improves polymerase activity. In some embodiments, the recombinant and/or variant PumA1 polymerase exhibits improved processivity compared to a reference polymerase (e.g., a reference Phi29 polymerase). In some cases, a variant PumA1 polymerase exhibits improved processivity compared to a reference polymerase (e.g., a reference Phi29 polymerase or a wild-type PumA1 polymerase). In some embodiments, the provided recombinant and/or variant PumA1 polymerase produces more amplified nucleic acid compared to a reference polymerase. In some embodiments, the provided recombinant and/or variant PumA1 polymerase amplifies nucleic acid faster compared to a reference polymerase. In some embodiments, the nucleic acid amplification is a RCA reaction. In some embodiments, the provided recombinant and/or variant PumA1 polymerase generates a higher density of detected RCA products in an RCA reaction compared to a reference polymerase. In some embodiments, the provided recombinant and/or variant PumA1 polymerase generates a higher product signal intensity in an RCA reaction compared to a reference polymerase.

In some embodiments, the provided variant PumA1 polymerases, for example, those described in Section II.A, exhibit one or more altered or improved features (e.g., thermostability, processivity, and/or polymerization rate). In some aspects, the variant PumA1 polymerase exhibiting altered or improved features comprises one or more amino acid substitutions at one or more positions selected from among positions 545 and 574, corresponding to the positions of the sequence set forth in SEQ ID NO:1. In some embodiments, the variant PumA1 polymerase exhibiting altered or improved features further comprises an amino acid substitution at position 575. In some embodiments, the variant PumA1 polymerase exhibiting altered or improved features further comprises one or more amino acid substitutions other than at positions 545, 574, and 575. In some embodiments, the variant PumA1 polymerase exhibiting altered or improved features has at or about or at least at or about 90%, 95%, 96%, 97%, 98%, 99%, or 99.5% sequence identity to the amino acid sequence set forth in any one of SEQ ID NOS: 10-11. In some embodiments, the variant PumA1 polymerase exhibiting altered or improved features comprises the amino acid sequence set forth in any one of SEQ ID NOS: 10-11. In some embodiments, the variant PumA1 polymerase exhibiting altered or improved features has at or about or at least at or about 90%, 95%, 96%, 97%, 98%, 99%, or 99.5% sequence identity to the amino acid sequence set forth in any one of SEQ ID NO: 10. In some embodiments, the variant PumA1 polymerase exhibiting altered or improved features comprises the amino acid sequence set forth in any one of SEQ ID NO:11.

In some embodiments, the recombinant and/or variant PumA1 polymerase exhibiting one or more altered features (e.g., thermostability, processivity, and/or polymerization rate) described herein is used for a nucleic acid amplification process.

In some embodiments, the variant PumA1 polymerase produces at least 10%, at least 15%, at least 20%, at least 25%, or at least 30% more rolling circle amplification products than a reference (wild-type) PumA1 polymerase under the same reaction conditions. In some embodiments, the variant PumA1 polymerase produces at least 10%, at least 15%, at least 20%, at least 25%, or at least 30% more rolling circle amplification products than a reference (wild-type) Phi29 polymerase under the same reaction conditions. In some embodiments, the recombinant polymerase produces at least 10%, at least 15%, at least 20%, at least 25%, or at least 30% more rolling circle amplification products than a reference (wild-type) Phi29 polymerase under the same reaction conditions.

In some embodiments, the variant PumA1 polymerase produces at or about or at least at or about 1%, 5%, 10%, 15%, 20%, 25%, 30%, 40%, 50%, 75%, 100%, 150%, or 200% more amplified nucleic acid compared to a reference polymerase (e.g., a reference wild-type PumA1 polymerase or a Phi29 polymerase). In some embodiments, the variant PumA1 polymerase produces between 10% and 200%, 25% and 175%, 50% and 150%, 75% and 125%, 90% and 110%, or 95% and 105% more amplified nucleic acid compared to a reference polymerase (e.g., a reference wild-type PumA1 polymerase or a Phi29 polymerase). In some embodiments, the variant PumA1 polymerase produces more amplified nucleic acid compared to a reference polymerase (e.g., a reference wild-type PumA1 polymerase or a Phi29 polymerase), such that the polymerization reaction time can be reduced, the amount of input template nucleic acid can be reduced, the product signal from the increased nucleic acid yield is increased, or a combination thereof. In some embodiments, the variant PumA1 polymerase amplifies nucleic acid (e.g., product signal per unit of time) at or about or at least at or about 1%, 5%, 10%, 15%, 20%, 25%, 30%, 40%, 50%, 75%, 100%, 150%, or 200% faster compared to a reference polymerase (e.g., a reference wild-type PumA1 polymerase or a Phi29 polymerase). In some embodiments, the variant PumA1 polymerase amplifies between 10% and 200%, 25% and 175%, 50% and 150%, 75% and 125%, 90% and 110%, or 95% and 105% more nucleic acid in a unit of time compared to a reference polymerase (e.g., a reference wild-type PumA1 polymerase or a Phi29 polymerase). For example, the variant PumA1 polymerase produces between 100% and 200% more amplified nucleic acid in 1 hour compared to a reference polymerase (e.g., a reference wild-type PumA1 polymerase or a Phi29 polymerase). In some embodiments, the variant PumA1 polymerase exhibiting improved thermostability amplifies nucleic acid faster for at least 1, 2, 3, 4, 6, 8, 10, 12 hours or more compared to a reference polymerase (e.g., a reference wild-type PumA1 polymerase or a Phi29 polymerase). In some embodiments, the variant PumA1 polymerase produces amplified nucleic acid at a faster rate compared to a reference polymerase (e.g., a reference wild-type PumA1 polymerase or a Phi29 polymerase), such that the polymerization reaction time can be reduced, the product signal from the increased nucleic acid amplification rate is increased, or a combination thereof.

In some embodiments, the PumA1 polymerase (e.g., recombinant wild-type PumA1 polymerase or variant PumA1 polymerase) exhibiting one or more altered features (e.g., thermostability, processivity, and/or polymerization rate) described herein is used for a nucleic acid amplification process, wherein the nucleic acid amplification is a RCA reaction. In some embodiments, the variant PumA1 polymerase produces a density of detected RCA products at or about or at least at or about 1%, 5%, 10%, 15%, 20%, 25%, 30%, 40%, 50%, 75%, 100%, 150%, or 200% higher compared to a reference polymerase (e.g., a reference wild-type PumA1 polymerase or a Phi29 polymerase). In some embodiments, the variant PumA1 polymerase described herein produces density of detected RCA products at least between 10% and 200%, 25% and 175%, 50% and 150%, 75% and 125%, 90% and 110%, or 95% and 105% higher compared to a reference polymerase (e.g., a reference wild-type PumA1 polymerase or a Phi29 polymerase). In some embodiments, the variant PumA1 polymerase described herein produces a product signal intensity at or about or at least at or about 1%, 5%, 10%, 15%, 20%, 25%, 30%, 40%, 50%, 75%, 100%, 150%, or 200% higher compared to a reference polymerase (e.g., a reference wild-type PumA1 polymerase or a Phi29 polymerase). In some embodiments, the variant PumA1 polymerase described herein produces a product signal intensity at least between 10% and 200%, 25% and 175%, 50% and 150%, 75% and 125%, 90% and 110%, or 95% and 105% higher to a reference polymerase (e.g., a reference wild-type PumA1 polymerase or a Phi29 polymerase).

In some embodiments, the provided PumA1 polymerase described herein (e.g., recombinant wild-type PumA1 polymerase or variant PumA1 polymerase) further exhibits a longer half-life in the absence of substrate compared to a reference PumA1 polymerase. In some embodiments, the provided variant PumA1 polymerase described herein further exhibits a longer half-life in the presence of substrate compared to a reference PumA1 polymerase. In some embodiments, the provided variant PumA1 polymerase is more stable in the presence and absence of substrate compared to a reference PumA1 polymerase. In some embodiments, the variant PumA1 polymerase substrate comprises a nucleotide, a nucleotide derivative, a polynucleotide, or a combination thereof. In some embodiments, the variant PumA1 polymerase exhibits an extended half-life that is or about 5%, 10%, 15%, 20%, 25%, 30%, 40%, 50%, 75%, 100%, 150%, 200%, 300%, 400%, or 500% longer compared to a reference PumA1 polymerase in the presence or absence of substrate. In some embodiments, the provided variant PumA1 polymerase described herein exhibits an extended half-life between 5% and 500%, 15% and 300%, 50% and 400%, 30% and 100%, 20% and 200%, 40% and 150%, 75% and 400%, or 50% and 300% longer compared to a reference PumA1 polymerase in the presence or absence of substrate.

In some embodiments, the recombinant polymerase (e.g., a recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2) produces a density of detected RCA products at or about or at least at or about 1%, 5%, 10%, 15%, 20%, 25%, 30%, 40%, 50%, 75%, 100%, 150%, or 200% higher compared to a reference polymerase (e.g., a Phi29 polymerase). In some embodiments, a recombinant polymerase described herein produces a density of detected RCA products between 10% and 200%, 25% and 175%, 50% and 150%, 75% and 125%, 90% and 110%, or 95% and 105% higher compared to a reference polymerase (e.g., a Phi29 polymerase). In some embodiments, a recombinant polymerase described herein produces a product signal intensity at or about or at least at or about 1%, 5%, 10%, 15%, 20%, 25%, 30%, 40%, 50%, 75%, 100%, 150%, or 200% higher compared to a reference polymerase (e.g., a Phi29 polymerase). In some embodiments, a recombinant polymerase described herein produces a product signal intensity at least between 10% and 200%, 25% and 175%, 50% and 150%, 75% and 125%, 90% and 110%, or 95% and 105% higher to a reference polymerase (e.g., a Phi29 polymerase).

In some embodiments, the recombinant polymerase (e.g., a recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2) produces smaller RCA products at or about or at least at or about 1%, 5%, 10%, 15%, 20%, 25%, 30%, 40%, 50%, 75%, or 100%, smaller compared to a reference polymerase (e.g., a Phi29 polymerase). In some embodiments, a recombinant polymerase described herein produces smaller RCA products between 10% and 100%, 25% and 75%, 50% and 100%, 75% and 10%, or 00% and 50%, smaller compared to a reference polymerase (e.g., a Phi29 polymerase). In some embodiments, a recombinant polymerase described herein produces smaller RCA products compared to a reference polymerase (e.g., a Phi29 polymerase) in similar amplification reaction conditions (e.g., same concentration of reagents and reaction time). In some embodiments, a recombinant polymerase described herein produces smaller RCA products due to slower activity compared to a reference polymerase (e.g., a Phi29 polymerase) in similar amplification reaction conditions (e.g., same concentration of reagents and reaction time).

In any of the embodiments herein, the recombinant polymerase or the variant PumA1 polymerase may have strand displacing activity. In any of the embodiments herein, the recombinant polymerase or variant PumA1 polymerase may exhibit a mean nucleotide polymerization rate of at least 1000 nucleotides (nt)/min, at least 1500 nt/min, at least 2000 nt/min, or at least 2280 nt/min. In some embodiments, the recombinant polymerase or variant PumA1 polymerase may exhibit a mean nucleotide polymerization rate of between 1000 nucleotides (nt)/min and 2500 nt/min, between 1000 nt/min and 2280 nt/min, between 1000 nt/min and 2000 nt/min, between 2000 nt/min and 2500 nt/min, or between 2000 nt/min and 2280 nt/min. In some cases, the mean polymerization rate is measured at a temperature of at least or about 30° C. In some cases, the mean polymerization rate is measured at a temperature of at least or about 37° C. In some cases, the mean polymerization rate is measured at a temperature of at least or about 40° C. In some cases, the mean polymerization rate is measured at a temperature of at least or about 42° C.

In any of the embodiments herein, the recombinant polymerase or variant PumA1 polymerase may exhibit a nucleic acid replication error rate of fewer than 10-5 errors/bp, fewer than 10-6 errors/bp, or fewer than 10-7 errors/bp. In any of the embodiments herein, the recombinant polymerase or the variant PumA1 polymerase may exonuclease activity. In any of the embodiments herein, the recombinant polymerase or the variant PumA1 polymerase may have reverse transcriptase activity.

In some aspects described herein, the reference polymerase is a wild-type PumA1 polymerase, such as any wild-type PumA1 polymerase described herein. In some aspects described herein, the reference polymerase is a PumA1 polymerase that does not comprise the one or more amino acid substitutions, such as any wild-type PumA1 polymerase described herein. In some aspects, the reference polymerase is a Phi29 polymerase (e.g., a wild-type Phi29 polymerase), and the recombinant polymerase or variant polymerase exhibits one or more improved features relative to the Phi29 polymerase.

III. NUCLEIC ACIDS, VECTORS AND EXPRESSION SYSTEMS

Also provided herein are polynucleotides, vectors, and expression systems encoding any of the provided recombinant polymerases or variant PumA1 polymerases disclosed herein, for example, any of those described in Section I.

The nucleic acids may include those encompassing natural and/or non-naturally occurring nucleotides and bases, e.g., including those with backbone modifications. The terms "nucleic acid molecule," "nucleic acid," and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

In some embodiments, the recombinant polymerase may comprise a heterologous sequence (e.g., one or more affinity tags and/or one or more solubility tags). In some embodiments, the recombinant polymerase comprises the sequence of a wild-type PumA1 polymerase (e.g., provided in SEQ ID NO:1). In some embodiments, the recombinant polymerase comprises the sequence of a variant PumA1 polymerase. In some embodiments, the variant PumA1 polymerase may be a recombinantly produced variant of the natural protein in which one or more property, such as thermostability, has been altered. In some aspects, the nucleic acid is synthetic. In some aspects, the nucleic acid molecule can be modified (e.g., codon optimization) for use in the constructs described herein. In some cases, the sequences can be designed to contain terminal restriction site sequences for purposes of cloning into vectors.

A. Polynucleotides

In some embodiments, provided herein is a polynucleotide encoding a recombinant polymerase comprising an amino acid sequence having at least or about 90%, 95%, 96%, 97%, 98%, 99%, or 99.5% sequence identity to the sequence set forth in SEQ ID NO: 1 or SEQ ID NO: 2. In some embodiments, provided herein is a polynucleotide encoding a recombinant polymerase comprising the sequence set forth in SEQ ID NO:1. In some embodiments, provided herein is a polynucleotide encoding a recombinant polymerase comprising the sequence set forth in SEQ ID NO:2. In some embodiments, provided herein is polynucleotide encoding a recombinant polymerase comprising an amino acid sequence having at least or about 90%, 95%, 96%, 97%, 98%, 99%, or 99.5% sequence identity to the sequence set forth in SEQ ID NO: 10 or SEQ ID NO:11. In some embodiments, provided herein is a polynucleotide encoding a recombinant polymerase comprising the sequence set forth in SEQ ID NO:10. In some embodiments, provided herein is a polynucleotide encoding a recombinant polymerase comprising the sequence set forth in SEQ ID NO: 11. In some embodiments, provided herein is a polynucleotide encoding a variant PumA1 polymerase. In some embodiments, the polynucleotide encodes a variant PumA1 polymerase comprising one or more amino acid modifications or variations (e.g., substitutions, insertions, deletions, and/or combinations thereof) compared to the sequence of the wild-type PumA1 polymerase. In some embodiments, provided herein is polynucleotide encoding a variant PumA1 polymerase comprising an amino acid sequence having at least or about 90%, 95%, 96%, 97%, 98%, 99%, or 99.5% sequence identity to the sequence set forth in SEQ ID NO:10 or SEQ ID NO:11. In some embodiments, provided herein is a polynucleotide encoding a variant PumA1 polymerase comprising the sequence set forth in SEQ ID NO:10. In some embodiments, provided herein is a polynucleotide encoding a variant PumA1 polymerase comprising the sequence set forth in SEQ ID NO: 11. In some embodiments, the polynucleotides encode any of the provided variant PumA1 polymerases described herein, such as those described in Section II.A.

Amino acid sequence variants of a PumA1 polymerase may be prepared by introducing appropriate modifications into the nucleotide sequence encoding the wild-type PumA1 polymerase. Such modifications include, for example, deletions from and/or insertions into and/or substitutions of residues within the nucleotide sequences encoding the wild-type PumA1 polymerase. The encoded variant PumA1 polymerase can comprise any combination of deletion, insertion, and substitutions. In some aspects, the encoded variant PumA1 polymerase exhibits desired characteristics, e.g., improved polymerase activity, features and/or properties.

In some aspects, provided is a polynucleotide sequence encoding any of the provided recombinant polymerases or variant PumA1 polymerases, such as any of those described in Section II.A. In some aspects, the encoded recombinant polymerase or variant PumA1 polymerase exhibits or possesses one or more of the exemplary features or properties, such as any of those described in Section II.B.

In some aspects, provided is a polynucleotide sequence encoding any of the recombinant polymerases provided herein, such as any of those described in Section II.A. In some aspects, provided is a polynucleotide sequence encoding any of the provided variant PumA1 polymerases, such as any of those described in Section II.A In some embodiments, the polynucleotide encodes a variant PumA1 polymerase comprising amino acid substitutions at positions 545, 574, and/or 575, corresponding to the positions of the wild-type PumA1 polymerase amino acid sequence set forth in SEQ ID NO:1. In some embodiments, the polynucleotide encodes an amino acid sequence that has at least at or about 90%, 95%, 96%, 97%, 98%, 99%, or 99.5% sequence identity to the sequence set forth in SEQ ID NO: 1. In some embodiments, the polynucleotide encodes a variant PumA1 polymerase comprising amino acid substitutions I545E, A574S, and/or P575V, corresponding to the positions of the wild-type PumA1 polymerase amino acid sequence set forth in SEQ ID NO:1. In some embodiments, the polynucleotide encodes a variant PumA1 polymerase comprising amino acid substitutions at positions 544, 573, and/or 574, corresponding to the positions of the amino acid sequence set forth in SEQ ID NO:2. In some embodiments, the polynucleotide encodes an amino acid sequence that has at least at or about 90%, 95%, 96%, 97%, 98%, 99%, or 99.5% sequence identity to the sequence set forth in SEQ ID NO:2. In some embodiments, the polynucleotide encodes a variant PumA1 polymerase comprising amino acid substitutions I544E, A573S, and/or P574V, corresponding to the positions of the amino acid sequence set forth in SEQ ID NO:2.

In some embodiments, provided is a polynucleotide sequence having at least at or about 90%, 95%, 96%, 97%, 98%, 99%, or 99.5% sequence identity to the nucleotide sequence set forth in SEQ ID NO:8 or SEQ ID NO:9. In some embodiments, provided is a polynucleotide sequence having at least at or about 90%, 95%, 96%, 97%, 98%, 99%, or 99.5% sequence identity to the nucleotide sequence set forth in SEQ ID NO:8. In some embodiments, provided is a polynucleotide sequence having at least at or about 90%, 95%, 96%, 97%, 98%, 99%, or 99.5% sequence identity to the nucleotide sequence set forth in SEQ ID NO:9. In some embodiments, the polynucleotide sequence comprises the sequence set forth in SEQ ID NO:8. In some embodiments, the polynucleotide sequence comprises the sequence set forth in SEQ ID NO:9.

In some embodiments, the polynucleotide sequence encoding the provided recombinant polymerase or variant PumA1 polymerase is codon-optimized for a host cell or a recombinant expression system to generate the variant PumA1 polymerase. Typically, codon optimization involves balancing the percentages of codons selected with the published abundance of transfer RNAs appropriate for the host cell or expression system so that none is overloaded or limiting. This may be advantageous in some cases because most amino acids are encoded by more than one codon, and codon usage varies from organism to organism. Differences in codon usage between transfected genes and host cells can have effects on protein expression and immunogenicity of a nucleic acid construct. In general, for codon optimization, codons are chosen to select for those codons that are in balance with the host cell usage frequency. Typically, the redundancy of the codons for amino acids is such that different codons code for one amino acid. In some embodiments, in selecting a codon for replacement, it may be desired that the resulting mutation is a silent mutation such that the codon change does not affect the amino acid sequence. Generally, the last nucleotide of the codon can remain unchanged without affecting the amino acid sequence.

B. Recombinant Nucleic Acids and Vectors

In some aspects, provided herein is a recombinant nucleic acid comprising any of the polynucleotides described in Section III.A. In some aspects, provided herein is a vector comprising any of the polynucleotides described in Section III.A. In some embodiments, the recombinant nucleic acid or vector comprises a polynucleotide encoding a recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2. In some embodiments, the recombinant polymerase comprises a heterologous sequence (e.g., one or more affinity tags and/or one or more solubility tags). In some embodiments, the recombinant nucleic acid or vector comprises a polynucleotide encoding a variant PumA1 polymerase described herein, that comprises one or more amino acid modifications or variations, e.g., substitutions, deletions, insertions, and/or mutations, compared to the sequence of the wild-type PumA1 polymerase.

In some embodiments, the recombinant nucleic acid molecule comprises a polynucleotide described in Section III.A.

In some embodiments, the recombinant nucleic acid molecule further comprises a transcription regulatory sequence operatively linked with the polynucleotide. In some embodiments, the transcription regulatory sequence comprises a promoter selected from among a bacterial, viral, and mammalian promoter. In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, a vector is provided comprising polynucleotide described in Section III.A or a recombinant nucleic acid molecule described herein, such as those encoding any of the recombinant polymerases or variant PumA1 polymerases described herein. In some embodiments, the vector is a plasmid, a viral vector, a cosmid, or a transposon. The expression vector can be any suitable recombinant expression vector, and can be used to transform or transfect any suitable host. Suitable vectors include those designed for propagation and expansion or for expression or both, such as plasmids and viruses. In some embodiments, the vector is an expression vector. Exemplary vectors can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as AG10, AGT11, AZapII (Stratagene), NEMBL4, and ANM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech). In some cases, the vector is a viral vector. In some such aspects, the viral vector is a retroviral vector, such as a lentiviral vector.

C. Host Cells and Expression Systems

In some instances, provided herein are host cells or recombinant expression systems comprising any of the polynucleotides, recombinant nucleic acid molecules, or vectors provided herein, such as any that are described in Section III. In some embodiments, the polynucleotide, the recombinant nucleic acid molecule, and/or the vector is for use in transforming the host cell or recombinant expression system to generate a transformed host cell or recombinant expression system.

The polynucleotide, the recombinant nucleic acid molecule, and/or the vector can be introduced into the host cell or recombinant expression system using various methods for introduction or transfer of nucleic acids, including via viral, e.g., retroviral or lentiviral, transduction, transposons, and electroporation. In some aspects, the recombinant expression system comprises a host cell, such as any host cells described herein.

In some embodiments, the transformed host cell or recombinant expression system generates a recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2. In some embodiments, the recombinant polymerase comprises a heterologous sequence. In some embodiments, the transformed host cell or recombinant expression system generates a variant PumA1 polymerase. In some embodiments, the host cell or recombinant expression system is used to produce the recombinant polymerase or variant PumA1 polymerase. In some embodiments, the host cell or recombinant expression system is a cell system or a cell-free system. In some embodiments, the host cell or recombinant expression system comprises one or more cell systems selected from among a bacterial cell, a fungal cell, an insect cell, and a mammalian cell. In some embodiments, a cell system may be selected from a group comprising *E. coli, S. cerevisiae, D. melanogaster*, and CHO cells. For example, *E. coli* is a bacterial cell that can be transformed with the polynucleotide, recombinant nucleic acid, and/or vector described herein for effective production of a recombinant polymerase or variant PumA1 polymerase. In some aspects, in a bacterial host cell or expression system, such as *E. coli*, protein translation is initiated with N-formyl-methionine (fMet), which during translation initiation is brought to the ribosome in the form of fMet-tRNA$^{fMet}$ In some aspects, the formylated methionine at the N-terminus of nascent bacterial proteins is typically removed co-translationally shortly after the nascent protein has emerged from the peptide exit tunnel of the ribosome, by peptide deformylase (PDF), and in the majority of cases, is followed by methionine excision by methionine aminopeptidase (MAP). Accordingly, in some aspects, bacterially produced proteins does not include an initial Met residue.

In some embodiments, the polynucleotide sequence encoding the recombinant polymerase or variant PumA1 polymerase is codon-optimized for the host cell or recombinant expression system, for example, as described in Section III.A.

IV. METHODS OF USING AND USES OF RECOMBINANT PUMA1 POLYMERASES, VARIANT PUMA1 POLYMERASES, AND COMPOSITIONS THEREOF, AND APPLICATIONS

Also provided herein are methods that involve or employ any of the provided variant and/or recombinant polymerases comprising PumA1 polymerases or variants thereof, compositions or kits that include a recombinant polymerase or variant PumA1 polymerase disclosed herein, or nucleic acids or vectors that encode the recombinant polymerases or variant PumA1 polymerases, and uses of any of the foregoing, such as for nucleic acid amplification and/or sequencing. In some aspects, the provided recombinant polymerase, variant PumA1 polymerase, or composition comprising the recombinant polymerase or variant PumA1 polymerase can be used in a variety of analysis or assessment methods or experiments (e.g., sequencing, genotyping, and amplification reactions), for assessing a biological sample. In some aspects, the provided variant PumA1 polymerases are used in amplifying nucleic acids, e.g., DNAs or RNAs, including in applications such as rolling circle amplification (RCA).

In some aspects, provided are methods for amplifying nucleic acids, such as DNA, that involve contacting a biological sample containing DNA to be amplified with any of the provided recombinant polymerases, variant PumA1 polymerases, or compositions disclosed herein.

In some aspects, provided are methods of performing a rolling circle amplification (RCA) that involves the use of any of the provided recombinant polymerases or variant PumA1 polymerases, compositions or kits that include a recombinant polymerase or variant PumA1 polymerase disclosed herein, or nucleic acids or vectors that encode the variant PumA1 polymerases. In some aspects, the method of performing RCA involves contacting a biological sample containing nucleic acids, e.g., DNA, to be amplified with any of the provided recombinant polymerases, variant PumA1 polymerases, or compositions comprising any of the recombinant polymerases or variant PumA1 polymerases disclosed herein. In some aspects, the methods thereby amplify the nucleic acid by RCA.

In some embodiments, the provided recombinant polymerase or variant PumA1 polymerase is used in a method that involves the amplification of a nucleic acid probe through rolling circle amplification. In some embodiments, RCA involves the use of circular or circularizable probes that recognize particular target nucleic acid sequences, and can be amplified via RCA (e.g., after circularization in the case of a circularizable probe) to be detected. In some embodiments, the circularizable probe or probe set (e.g., a padlock probe) contains one or more barcodes. In some embodiments, the barcodes are bound by detection probes, which do not need to be fluorescent, but that include a target-binding portion (e.g., for hybridizing to one or more primary probes) and multiple other barcodes (e.g., secondary barcodes, versus the primary barcodes on the primary probes). In some embodiments, the barcodes of the detection probes are targeted by detectably labeled detection oligonucleotides, such as fluorescently labeled oligonucleotides. In some embodiments, one or more decoding schemes are used to decode the signals, such as fluorescence, for sequence determination. Exemplary decoding schemes are described in Eng et al., Nature 2019; 568 (7751): 235-239; Chen et al., Science; 2015; 348 (6233): aaa6090; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, the provided recombinant polymerases, variant PumA1 polymerases, or compositions are used in methods that involve using a circular or circularizable construct hybridized to the nucleic acid of interest to generate a circular nucleic acid. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is a RNA-DNA templated ligation. In some embodiments, a splint is provided as a template for ligation.

In some embodiments, the method comprises contacting the biological sample with an amplification primer is added. In some instances, the amplification primer is added with one or more other probes, such as with the circular probe or circularizable probe or probe set. In some instances, the amplification primer may also be complementary to the target nucleic acid and the padlock probe (e.g., a SNAIL probe). In some embodiments, a washing step is performed to remove any unbound probes, primers, etc. In some embodiments, the wash is a stringency wash. Washing steps can be performed at any point during the process to remove non-specifically bound probes, probes that have ligated, etc.

In some instances, upon addition of the recombinant polymerase, variant PumA1 polymerase, or composition according to the present disclosure in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of a circularizable probe or probe set to generate a circularized probe) the circular or circularized probe is rolling-circle amplified to generate a RCA product (RCP) containing multiple copies of the RCP.

Following amplification, the sequence of the amplicon (e.g., RCA product) or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, a sequence of the RCA product is detected using, e.g., the secondary and higher order probes and detection oligonucleotides described herein.

In some instances, the provided recombinant polymerase or variant PumA1 polymerase can be used in a method for amplifying a DNA, such as a sequencing method, a genotyping method, or an amplification method. In some embodiments, the method involves contacting a biological sample containing DNA to be amplified with any of the provided recombinant polymerases, variant PumA1 polymerases, or compositions. In some embodiments, the method also involves incubating the biological sample and the recombinant polymerase, variant PumA1 polymerase, or composition.

In some embodiments, the biological sample containing DNA to be amplified with the recombinant polymerase or variant PumA1 polymerase comprises isolated or synthetic nucleic acids. In some embodiments, the biological sample is tested and/or analyzed in solution. In some embodiments, the biological sample is tested and/or analyzed in vitro. In some embodiments, the biological sample is an organ or a tissue sample. In some embodiments, the biological sample is tested in situ, for example, wherein the variant PumA1 polymerase is added to a freshly or previously prepared tissue sample for target analyte (e.g., gene or mRNA) analysis within a tissue slice. In some embodiments, the DNA is amplified by a rolling circle amplification (RCA) as described in this section. In some embodiments, the DNA is amplified by in situ RCA in the biological sample.

In some instances, the provided recombinant polymerases or variant PumA1 polymerases can be used in methods of performing a rolling circle amplification (RCA). In some embodiments, the methods involve contacting a biological sample containing DNA to be amplified with the recombinant polymerase, variant PumA1 polymerase, or composition. In some embodiments, the method also involves incubating the biological sample and the recombinant polymerase, variant PumA1 polymerase, or composition provided herein. In some embodiments, the recombinant polymerase, variant PumA1 polymerase, or composition used in the method of RCA can be any of those described in Section II.

In some embodiments, the method of RCA comprises incubating the biological sample and the recombinant polymerase, variant PumA1 polymerase, or composition at a specific temperature. In some embodiments, the temperature is optimal for maximizing activity of the PumA1 polymerase or variant thereof. In some embodiments, the PumA1 polymerase or variant thereof and the biological sample are incubated at a temperature of at or about 5° C., 10° C., 15° C., 20° C., 25° C., 30° C., 35° C., 40° C., 45° C., or higher. In some embodiments, the PumA1 polymerase or variant thereof and the biological sample are incubated at a temperature between 5° C. and 50° C., 10° C. and 45° C., 25° C. and 45° C., 30° C. and 45° C., or 35° C. and 45° C. In some embodiments, the PumA1 polymerase or variant thereof and the biological sample are incubated at an elevated temperature. In some embodiments, the PumA1 polymerase or variant thereof and the biological sample are incubated at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C. In some embodiments, the PumA1 polymerase or variant thereof and the biological sample are incubated between 30° C. and 50° C., 32° C. and 48° C., 34° C. and 46° C., 36° C. and 44° C., or 38° C. and 42° C.

In some embodiments, RCA is performed during incubation of the variant PumA1 polymerase and the biological sample. In some embodiments, the RCA is performed for about 0.25, 0.5, 0.75, 1, 1.5, 2, 2.5, 3, 4, 5, 6, 8, 10, 12, 14, 16, 18, 20, 22, or 24 hours. In some embodiments, the RCA is performed for 0.25, 0.5, 0.75, 1, 1.5, 2, 2.5, 3, 4, 5, 6, 8, 10, 12, 14, 16, 18, 20, 22, or 24 hours. In some embodiments, the RCA is performed for at or about 15 minutes, 30 minutes, 45 minutes, 1 hour, 2 hours, 3 hours, 6 hours, 12 hours, or longer. In some embodiments, the RCA is performed for more than 24 hours. In some embodiments, the RCA is performed for between 1 hour and 8 hours, 0.25 hour and 12 hours, 4 hour and 24 hours, 2 hour and 16 hours, 3 hour and 10 hours, 4 hour and 18 hours, 5 hour and 14 hours, or 0.5 hour and 20 hours. In some embodiments, RCA is performed for no more than 12 hours. In some embodiments, RCA is performed for no more than 8 hours. In some embodiments, RCA is performed for no more than 6 hours. In some embodiments, the incubation time used is sufficient to generate a detectable amount of an RCA product.

In some embodiments, the method of performing RCA further comprises detecting the amplification product. In some embodiments, the amplification product is an RCA product (RCP). In some embodiments, the amplification product is detected by contacting the biological sample with a fluorescent dye or affinity molecule. In some embodiments, the biological sample is contacted with a fluorescent dye or affinity molecule before initiating the RCA reaction. In some embodiments, the amplification product is detected by contacting the biological sample with SYBR gold or SYBR green. SYBR dyes are asymmetrical cyanine dyes used for staining double-stranded DNA, single-stranded DNA, and RNA molecules. In some embodiments, the amplification product is detected by contacting the biological sample with ATTO-532 (Rhodamine 6G). In some embodiments, the amplification product is detected in real time during the amplification.

In some embodiments, the provided methods employ a recombinant polymerase (e.g., comprising a PumA1 polymerase or variant thereof) or a variant PumA1 polymerase that exhibits one or more of any of the features described herein, such as those described in Section II.B.

Provided herein is a method for analysis comprising: contacting a sample with a nucleic acid probe that hybridizes to a target nucleic acid (e.g., an RNA) in the sample, wherein the nucleic acid probe is a circular probe or a circularizable probe comprising one or more barcodes; generating an amplification product by contacting the sample with an isolated recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2, or a variant thereof; and detecting a sequence of the amplification product. In some embodiments, the detecting of the sequence of the amplification product comprises contacting the biological sample with one or more detectably-labeled probes that directly or indirectly bind to the one or more barcode sequences or complements thereof in the amplification product, and detecting signals associated with the one or more detectably-labeled probes. In some embodiments, the one or more detectably-labeled probes indirectly bind to the one or more barcode sequences or complements thereof via one or more intermediate probes that bind to the one or more barcode sequences or complements thereof, wherein the one or more intermediate probes are detectable using one or more detectably-labeled probes.

A. Samples

A sample, such as a biological sample, that can be assessed or analyzed using any of the recombinant polymerases, variant PumA1 polymerases, compositions or kits that include recombinant polymerase or variant PumA1 polymerase disclosed herein, or nucleic acids or vectors that encode the recombinant polymerase or variant PumA1 polymerases as provided herein, can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can include nucleic acids (such as DNA or RNA), proteins/polypeptides, carbohydrates, and/or lipids. The biological sample can be obtained as a tissue sample, such as a tissue section, biopsy, a core biopsy, a cell pellet, a cell block, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface. In some embodiments, the biological sample is a tissue sample. In some embodiments, the tissue sample is an intact tissue sample or a non-homogenized tissue sample.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

B. Analytes

The methods and compositions provided herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a circularizable probe or circular probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

1. Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labeling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

2. Labeling Agents

In some embodiments, the methods and compositions provided herein can be used for analyzing endogenous analytes (e.g., RNA, ssDNA, cell surface or intracellular proteins and/or metabolites) in a sample using one or more labeling agents. In some embodiments, an analyte labeling agent may include an agent that interacts with an analyte (e.g., an endogenous analyte in a sample). In some embodiments, the labeling agents can comprise a reporter oligonucleotide that is indicative of the analyte or portion thereof interacting with the labelling agent. For example, the reporter oligonucleotide may comprise a barcode sequence that permits identification of the labeling agent. In some cases, the sample contacted by the labelling agent can be further contacted with a probe (e.g., a single-stranded probe sequence), that hybridizes to a reporter oligonucleotide of the labeling agent, in order to identify the analyte associated with the labeling agent. In some embodiments, the analyte labeling agent comprises an analyte binding moiety and a labeling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method involves one or more post-fixing (also referred to as post-fixation) steps after contacting the sample with one or more labeling agents.

In the methods and systems described herein, one or more labeling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labeling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labeling agents can include (e.g., are attached to) a reporter oligonucleotide that is indicative of the cell surface feature to which the binding group binds. For example, the reporter oligonucleotide may comprise a barcode sequence that permits identification of the labeling agent. For example, a labeling agent that is specific to one type of cell feature (e.g., a first cell surface feature) may have coupled thereto a first reporter oligonucleotide, while a labeling agent that is specific to a different cell feature (e.g., a second cell surface feature) may have a different reporter oligonucleotide coupled thereto. For a description of exemplary labeling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labeling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labeling agents are the same. In some embodiments in which the plurality of analytes includes a single species of analyte, the analyte binding moieties of the plurality of analyte labeling agents are the different (e.g., members of the plurality of analyte labeling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labeling agent that is specific to a particular cell feature may have a first plurality of the labeling agent (e.g., an antibody or lipophilic moiety) coupled to a first reporter oligonucleotide and a second plurality of the labeling agent coupled to a second reporter oligonucleotide.

In some aspects, these reporter oligonucleotides may comprise nucleic acid barcode sequences that permit identification of the labeling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using the in situ detection techniques described herein.

Attachment (coupling) of the reporter oligonucleotides to the labeling agents may be achieved through any of a variety of direct or indirect, covalent or non-covalent associations or attachments. For example, oligonucleotides may be covalently attached to a portion of a labeling agent (such a protein, e.g., an antibody or antibody fragment) using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labeling and Affinity Purification of Synthetic Oligonucleotides," Nucleic Acids Res. Jan. 15, 2003; 31 (2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labeling agents. Commercially available kits, such as those from Thunderlink and Abcam, and techniques common in the art may be used to couple reporter oligonucleotides to labeling agents as appropriate. In another example, a labeling agent is indirectly (e.g., via hybridization) coupled to a reporter oligonucleotide comprising a barcode sequence that identifies the label agent. For instance, the labeling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labeling agent to the reporter oligonucleotide. In some embodiments, the reporter oligonucleotides are releasable from the labeling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein.

In some cases, the labeling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labeling agent (or reporter oligonucleotide) either directly or indirectly (e.g., the label can be conjugated to a molecule that can bind to the labeling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety (ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labeling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

3. Products of Endogenous Analyte and/or Labeling Agent

In some embodiments, provided herein are methods and compositions for generating and/or analyzing one or more products of an endogenous analyte and/or a labeling agent in a biological sample. In some embodiments, an endogenous analyte (e.g., a viral or cellular DNA or RNA) or a product (e.g., an amplification product or an extension product, for example, produced by a recombinant polymerase comprising a PumA1 polymerase or variant thereof), a replication product, a transcription/reverse transcription product, and/or an amplification product such as a rolling circle amplification (RCA product) thereof is analyzed. In some embodiments, a labeling agent that directly or indirectly binds to an analyte in the biological sample is analyzed. In some embodiments, a product (e.g., an amplification product such as a rolling circle amplification (RCA product), an extension product (e.g., by a nucleic acid polymerase), a hybridization product, a ligation product, a replication product, a transcription/reverse transcription product), and/or of a labeling agent that directly or indirectly binds to an analyte in the biological sample is analyzed.

C. Detection and Analysis

In some aspects, provided herein are methods comprising in situ assays, such as an in situ assay that involves the use of any of the recombinant polymerases or variant PumA1 polymerases provided herein. In some aspects, the in situ assays involve generation of the amplification product in situ, for example using any of the recombinant polymerases or variant PumA1 polymerases or compositions provided herein, and detection of the amplified product in situ, for example, using microscopy or other detection or determination methods involving an optical readout. In other aspects, the nucleic acid amplification and/or detection is performed in vitro.

In some aspects, detection or determination of a sequence of a target nucleic acid or amplification product thereof is performed in situ in a cell in an intact tissue. In some aspects, the methods involve in situ generation of nucleic acid amplification product, such as an rolling circle amplification (RCA) product using any of the recombinant polymerases, variant PumA1 polymerases, or compositions provided herein, and detecting the amplification products.

In some embodiments, the method involves imaging the sample to detect a signal associated with a probe (e.g., circular or circularizable probe) hybridized to a target nucleic acid in the sample. In some embodiments, the probe hybridized to the target nucleic acid comprises one or more barcode sequences for detection and/or a means for signal amplification (e.g., RCA). In some embodiments, the signal can be amplified in situ in the sample. In some embodiments, the signal associated with the probe is amplified in the sample (e.g., using any of the recombinant polymerases or variant PumA1 polymerases or compositions provided herein). In some embodiments, an amplified signal associated with the probe and the associated RCA product can be generated in the sample (e.g., using detection probes such as fluorescently labeled probes).

In some embodiments, the methods involve imaging the biological sample to detect a particular nucleic acid or an amplification product thereof. In some embodiments, a sequence of the rolling circle amplification product, or other generated product can be analyzed in situ in the biological sample. In some of any embodiments, the imaging can comprise detecting a signal associated with a fluorescently labeled probe that directly or indirectly binds to a rolling circle amplification product of the circularized probe. In some embodiments, the sequence of the rolling circle amplification product, extension product, or other generated product can be analyzed by sequential hybridization, sequencing by hybridization, sequencing by ligation, sequencing by synthesis, sequencing by binding, or a combination thereof. In some embodiments, barcodes or complements thereof (e.g., barcode sequences or complements thereof comprised by the probes disclosed herein or products thereof) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the barcodes by sequential hybridization and detection with a plurality of labelled probes (e.g., detection probes (e.g., detection oligos) or barcode probes). In some instances, the barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte can be detected as performed in sequential fluorescent in situ hybridization (seqFISH).

In some aspects, an in situ hybridization based assay is used to localize and analyze nucleic acid sequences (e.g., a probe comprising one or more specific barcode sequences of interest) within a native biological sample, e.g., a portion or section of tissue. In some embodiments, the in situ assay is used to analyze the presence, absence, an amount or level of the probe hybridized to a nuclei acid substrate in a biological sample, while preserving spatial context.

In some embodiments, the methods involve in situ hybridization using directly or indirectly labeled molecules, e.g., complementary DNA or RNA or modified nucleic acids, as probes that bind or hybridize to an RNA substrate within a biological sample of interest. Nucleic acid probes or probe sets, in some examples, may be labelled with radioisotopes, epitopes, hapten, biotin, or fluorophores, to enable detection of the location of specific nucleic acid probes or probe sets in tissues.

In some embodiments, barcode sequences of the circular or circularizable probes (or products thereof, such as amplification, extension, ligation, or hybridization products) are targeted by detectably labeled detection probes, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," Nature 568 (7751): 235-239 (2019); Chen et al., "Spatially resolved, highly multiplexed RNA profiling in single cells," Science; 348 (6233): aaa6090 (2015); Gyllborg et al., Nucleic Acids Res (2020) 48 (19): e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, a barcode sequence in a probe herein (e.g., a circular or circularizable probe) or a product thereof can be analyzed by in situ sequencing. In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing by synthesis.

In some embodiments, the in situ hybridization comprises sequential fluorescent in situ hybridization. In some embodiments, the analysis and/or sequence determination comprises detecting a product generated by amplification using any of the recombinant polymerases or variant PumA1 polymerases or compositions provided herein. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the detection or determination is performed when the RNA substrate is in situ in the tissue sample.

In some aspects, in situ assays use microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, the detection or determination is of a sequence associated with or indicative of a target nucleic acid. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a provided method is quantitative and preserves the spatial information within a tissue sample without physically isolating cells or using homogenates.

In some aspects, the methods also involve imaging the amplification product (e.g., amplicon) and/or one or more portions of the polynucleotides, for example, via binding of a detection probe that is detectably labeled (e.g., to a sequence of circular or circularizable probe or a complement thereof) and detecting the detectable label. In some embodiments, the detectably labeled probe comprises a detectable label that can be measured and quantitated. A label or detectable label can be a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

A fluorophore can comprise a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. Autofluorescence can comprise background fluorescence (that can arise from a variety of sources, including aldehyde fixation, extracellular matrix components, red blood cells, lipofuscin, and the like), which is distinct from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (Max Vision Biosciences), and/or a very intense black dye (e.g., Sudan Black, or comparable dark chromophore).

In some embodiments, a detectable probe containing a detectable label can be used to detect one or more poly-nucleotide(s) and/or amplification products (e.g., amplicon) described herein (e.g., a probe hybridized to an RNA sub-strate). In some embodiments, the methods involve incubat-ing the detectable probe containing the detectable label with the sample, washing unbound detectable probe, and detect-ing the label, e.g., by imaging.

Examples of detectable labels comprise but are not lim-ited to various radioactive moieties, enzymes, prosthetic groups, fluorescent markers, luminescent markers, biolumi-nescent markers, metal particles, protein-protein binding pairs and protein-antibody binding pairs. Examples of fluo-rescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylam-ine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as 1251, 35S, 14C, or 3H. Identifiable markers are commercially available from a variety of sources.

Examples of fluorescent labels and nucleotides and/or polynucleotides conjugated to such fluorescent labels com-prise those described in, for example, Hoagland, Handbook of Fluorescent Probes and Research Chemicals, Ninth Edi-tion (Molecular Probes, Inc., Eugene, 2002); Keller and Manak, DNA Probes, 2nd Edition (Stockton Press, New York, 1993); Eckstein, editor, Oligonucleotides and Ana-logues: A Practical Approach (IRL Press, Oxford, 1991); and Wetmur, Critical Reviews in Biochemistry and Molecular Biology, 26:227-259 (1991). In some embodiments, exem-plary techniques and methods methodologies applicable to the provided embodiments comprise those described in, for example, U.S. Pat. Nos. 4,757,141, 5,151,507 and 5,091, 519. In some embodiments, one or more fluorescent dyes are used as labels for labeled target sequences, for example, as described in U.S. Pat. No. 5,188,934 (4,7-dichlorofluores-cein dyes); U.S. Pat. No. 5,366,860 (spectrally resolvable rhodamine dyes); U.S. Pat. No. 5,847,162 (4,7-dichlororho-damine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. A fluorescent label can comprise a signaling moiety that conveys information through the fluorescent absorption and/or emission proper-ties of one or more molecules. Exemplary fluorescent prop-erties comprise fluorescence intensity, fluorescence lifetime, emission spectrum characteristics and energy transfer.

Examples of commercially available fluorescent nucleo-tide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Nucleotides having other fluorophores can also be synthesized (See, Henegariu et al. (2000) Nature Biotechnol. 18:345).

Other fluorophores available for post-synthetic attach-ment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhod-amine B, Marina Blue, Oregon Green 488, Oregon Green 514, Pacific Blue, rhodamine 6G, rhodamine green, rhod-amine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/strepta-vidin derivative (e.g., phycoerythrin-conjugated streptavi-din), or a detectably labeled anti-biotin antibody. Digoxi-genin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy suc-cinimide (NHS) derivatized fluorescent dye. In general, any member of a conjugate pair may be incorporated into a detection polynucleotide provided that a detectably labeled conjugate partner can be bound to permit detection. In some embodiments, an antibody comprises an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahis-tidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxi-genin/a-digoxigenin, dinitrophenol (DNP)/a-DNP, 5-Car-boxyfluorescein (FAM)/a-FAM.

In some embodiments, a nucleotide and/or an polynucle-otide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and 5,192,782. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting comprises determining a signal, e.g., a fluorescent signal. In some aspects, the detection (comprising imaging) is carried out using any one of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The fluorescence microscope can be any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity-so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECS™), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequences can be analyzed in situ, e.g., by incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ analysis are described, for example, in Mitra et al., (2003) Anal. Biochem. 320, 55-65, and Lee et al., (2014) Science, 343 (6177), 1360-1363; US 2016/0024555; US 2019/0194709; U.S. Pat. Nos. 10,138,509; 10,494,662; 10,179,932.

In some cases, sequencing can be performed after the analytes are released from the biological sample. In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232.

In some embodiments, the method involve detecting the one or more barcode sequences in the circular or circularizable probe or a product thereof by contacting the biological sample that contains amplification products, with one or more detectably-labeled probes that directly or indirectly hybridize to the one or more barcode sequences, detecting signals associated with the one or more detectably-labeled probes, and dehybridizing the one or more detectably-labeled probes. In some embodiments, the contacting, detecting, and dehybridizing steps are repeated with the one or more detectably-labeled probes and/or one or more other detectably-labeled probes that directly or indirectly hybridize to the one or more barcode sequences. In some embodiments, the detectably labeled probes comprise a detectable label (e.g., are conjugated to a detectable label). In some embodiments, the detectably labeled probes are labeled with a sequence capable of hybridizing to a detection probe, wherein the detection probe comprises a detectable label (e.g., is conjugated to a detectable label). Methods of detecting and/or analyzing a sequence by sequential hybridization of probes have been described, for example, in U.S. Pat. Pub. 20210340618, the content of which is herein incorporated by reference in its entirety.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309:1728-1732, and in U.S. Pat. Nos. 5,599,675; 5,750,341; 6,969,488; 6,172,218; and 6,306,597.

In some embodiments, nucleic acid hybridization can be used for sequence detection. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

V. KITS, COMPOSITIONS, AND ARTICLES OF MANUFACTURE

Also provided herein are kits, compositions, and articles of manufacture, for example comprising a recombinant polymerase described in Section II or a variant PumA1 polymerase described in Section II and one or more additional components. In some embodiments, the kit comprises isolated and purified recombinant polymerases or a variant PumA1 polymerases as described in Section II.

In some embodiments, provided herein is a composition comprising a recombinant polymerase disclosed herein (e.g., a recombinant polymerase comprising an amino acid sequence having at least or about 90%, 95%, 96%, 97%, 98%, 99%, or 99.5% sequence identity to the sequence set forth in SEQ ID NO:1 or SEQ ID NO:2). In some embodiments, provided herein is a composition comprising a variant PumA1 polymerase disclosed herein (e.g., a variant PumA1 polymerase comprising one or more amino acid substitutions at one or more positions selected from among positions 545, 574, and 575 corresponding to the positions of the sequence set forth in SEQ ID NO: 1). In some embodiments, the variant PumA1 polymerase comprises one or more amino acid substitutions selected from the group consisting of I545E, A574S, and P575V.

In some embodiments, the composition has a pH of about 8.5. In some cases, the composition comprises between about 5 mM and about 10 mM $MgCl_2$. In some cases, the composition comprises between about 0.1 mM and about 0.2 mM dNTPs. In some instances, the composition comprises between about 1 mM and about 4 mM DTT. In some cases, the composition comprises between 1 mg/mL and 3 mg/mL BSA (e.g., about 2 mg/mL BSA). In some cases, the composition comprises between 5 mM and 15 mM $NH_4SO_4$ (e.g., about 10 mM $NH_4SO_4$).

In some embodiments, the composition comprises between about 0.05 UM and about 1 μM of the recombinant polymerase or variant PumA1 polymerase. In some cases, the composition comprises between about 0.5 μM and about 1 μM, between about 0.2 μM and about 1 μM, between about 0.8 μM and about 1 μM, or between about 0.05 UM and about 0.5 μM of the recombinant polymerase or variant PumA1 polymerase. In some cases, the composition comprises at least 1, 10, 50, or 100 μM of the recombinant polymerase or variant PumA1 polymerase. In some embodiments, the composition comprises between 10 and 50, between 10 and 100, between 50 and 100, between 25 and 50, or between 25 and 100 μM of the recombinant polymerase or variant PumA1 polymerase. In any of the embodiments herein, the recombinant polymerase or variant PumA1 polymerase may be at least 85%, at least 90%, or at least 95% soluble in the composition. In any of the embodiments herein, the recombinant polymerase or variant PumA1 polymerase may be at least 85%, at least 90%, or at least 95% soluble in the composition at 20° C., 30° C., 37° C., 40° C., or 42° C.

In some embodiments, the composition has a pH of about 8.5 and comprises 10 mM $MgCl_2$, 10 mM $NH_4SO_4$, 4 mM DTT, and 0.2 mg/mL BSA. In some embodiments, the composition further comprises 0.2 mM dNTPs.

In some embodiments, the composition has a pH of about 8.5 and comprises 10 mM $MgCl_2$, 10 mM $NH_4SO_4$, 1 mM DTT, and 0.2 mg/mL BSA. In some embodiments, the composition further comprises 0.1 mM dNTPs.

In some embodiments, the composition has a pH of about 8.5 and comprises 5 mM $MgCl_2$, 10 mM $NH_4SO_4$, 1 mM DTT, and 0.2 mg/mL BSA. In some embodiments, the composition further comprises 0.2 mM dNTPs.

In some embodiments, a kit comprises one or more additional reagents for performing the methods provided herein, for example reagents required for one or more steps for amplification, detection, sequencing, and/or sample preparation as described herein. In some embodiments, the kit comprises a recombinant polymerase or variant PumA1 polymerase, for example, any described herein in Section II, and/or a polynucleotide, recombinant nucleic acid molecule, or vector, for example, as described in Section III. In some cases, the kit comprises any of the compositions disclosed herein.

In some embodiments, the kit comprises a buffer or a buffer stock solution (e.g., a solution that can be diluted to form a working buffer solution. In some embodiments, the kit comprises a buffer stock solution that can be diluted 2-fold, 3-fold, 4-fold, 5-fold, 10-fold, 20-fold, 50-fold, or 100-fold to produce a working buffer having a pH of about 8.5 and comprising 10 mM $MgCl_2$, 10 mM $NH_4SO_4$, 4 mM DTT, and 0.2 mg/mL BSA. In some embodiments, the kit comprises a buffer stock solution that can be diluted 2-fold, 3-fold, 4-fold, 5-fold, 10-fold, 20-fold, 50-fold, or 100-fold to produce a working buffer having a pH of about 8.5 and comprising 10 mM $MgCl_2$, 10 mM $NH_4SO_4$, 1 mM DTT, and 0.2 mg/mL BSA. In some embodiments, the kit comprises a buffer stock solution that can be diluted 2-fold, 3-fold, 4-fold, 5-fold, 10-fold, 20-fold, 50-fold, or 100-fold to produce a working buffer having a pH of about 8.5 and comprising 5 mM $MgCl_2$, 10 mM $NH_4SO_4$, 1 mM DTT, and 0.2 mg/mL BSA. In some embodiments, the composition further comprises 0.2 mM dNTPs.

In some embodiments, the kit further comprises one or more components, such as a dNTP, a di-cation, and a reaction buffer. In some embodiments, the composition comprises $MgCl_2$, dNTPs, DTT, BSA, $NH_4SO$, or any combination thereof. In some embodiments, the kit further comprises a primer, a dNTP, a di-cation, and a reaction buffer. In some embodiments, the kit further comprises instructions for use, for example, instructions for amplifying a nucleic acid, e.g., using any of the recombinant polymerases or variant PumA1 polymerases or compositions provided herein.

In some embodiments, the kit further comprises a detection probe (e.g., a plurality of detectably labelled probes) for detection of a nucleic acid as described in Section IV, e.g., DNA or RNA. In some embodiments, the probe is a circular or circularizable probe (e.g., a padlock probe) for detection of the target nucleic acid, e.g., DNA or RNA.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection, such as barcode detection probes or detectable labels. In some embodiments, the kits optionally contain other components, for example nucleic acid primers, enzymes and reagents, buffers, nucleotides, modified nucleotides, reagents for additional assays.

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

VI. TERMINOLOGY

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined In some ways to accomplish the same objectives.

It is understood that aspects and embodiments of the invention described herein, in addition to embodiments "comprising" certain aspects and features, may include "consisting" and/or "consisting essentially of" aspects and embodiments. As used herein, the singular form "a", "an", and "the" includes plural references unless indicated otherwise. As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

In some aspects, conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine(S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g., U.S. Pat. No. 8,562,989; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270 (20): 11882-6, the contents of each of which are herein incorporated by reference in their entireties).

An amino acid substitution may include replacement of one amino acid in a polypeptide with another amino acid. Amino acid substitutions may be introduced to generate a variant PumA1 polymerase as described herein.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some contexts, conservative substitutions can involve the exchange of a member of one of these classes for another member of the same class. In some contexts, non-conservative amino acid substitutions can involve exchanging a member of one of these classes for another class. In some contexts, particular substitutions can be considered "conservative" or "non-conservative" depending on the stringency and context and environment of the particular residue in primary, secondary and/or tertiary structure of the protein.

The term "peptide" as used herein refers to a plurality of amino acids joined together, such as in a linear or circular chain. The term oligopeptide is typically used to describe peptides having between 2 and about 50 or more amino acids. Peptides larger than about 50 are often referred to as polypeptides or proteins.

The terms "polypeptide" and "protein" are used interchangeably to refer to a polymer of amino acid residues, and are not limited to a minimum length. Polypeptides, including the provided antibodies and antibody chains and other peptides, e.g., linkers, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An "isolated" protein, polypeptide or nucleic acid refers to a protein, polypeptide or nucleic acid molecule that has been separated from a component of its natural environment. An isolated protein or polypeptide can refer to a purified protein or polypeptide. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. An isolated protein or polypeptide (e.g., an isolated polymerase) includes a polymerase present in a composition comprising other molecules, including other proteins and/or nucleic acids, wherein the isolated protein or polypeptide has been separated from a component of its natural environment.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In some aspects, a "recombinant expression system" comprises a host cell.

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from among adenine (A), thymine (T), cytosine (C), or guanine (G), and a ribonucleic acid can have one or more bases selected from among uracil (U), adenine (A), cytosine (C), or guanine (G). Useful non-native bases that can be included in a nucleic acid or nucleotide are known in the art.

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

The term "polymerase" includes not only naturally-occurring enzymes but also all modified derivatives thereof, including also derivatives of naturally-occurring polymerase enzymes. For instance, in some embodiments, the polymerase can have been modified to remove 5'-3' exonuclease activity. Sequence-modified derivatives or mutants of polymerase enzymes that can be used include, but are not limited to, mutants that retain at least some of the functional, e.g. polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oNTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

The terms "detectable label," "optical label," and "label" are used interchangeably herein to refer to a directly or indirectly detectable moiety that is associated with (e.g., conjugated to) a molecule to be detected, e.g., a probe for in situ assay or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a probe associated with a feature. For example, detectably labeled features can include a fluorescent, a colorimetric, or a chemiluminescent label attached to a bead (see, for example, Rajeswari et al., J. Microbiol Methods 139:22-28, 2017, and Forcucci et al., J. Biomed Opt. 10:105010, 2015, the entire contents of each of which are incorporated herein by reference).

In some embodiments, a plurality of detectable labels can be attached to a feature, a probe, or composition to be detected. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPYR FL, BODIPYR TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18 (3)), DiO (DiOC18 (3)), DiR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTOR 11, SYTOR 13, SYTOR 17, SYTOR 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye@ 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions.

Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethyl-amino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

VII. EXAMPLES

The following examples are included for illustrative purposes only and are not intended to limit the scope of the present disclosure.

Example 1: Protein Solubility of Recombinant PumA1 Polypeptides

This example demonstrates protein solubility of two different recombinant PumA1 constructs: (1) a recombinant PumA1 polypeptide having an amino terminal polyhistidine/SUMO tag (N-His/Sumo) and (2) a recombinant PumA1 polypeptide having a carboxy-terminal polyhistidine/SET tag (C-His/SET).

*Escherichia coli* were transformed with plasmid vectors encoding the N-His/SUMO or C-His/SET recombinant PumA1 and expression of the recombinant polymerase was induced. The sequences of the N-His/SUMO and C-His/SET recombinant PumA1 constructs are shown in Table E1 below.

TABLE E1

| DNA and Amino Acid Sequences of N-His/SUMO and C-His/SET | | |
| --- | --- | --- |
| Construct | DNA sequence | Amino Acid Sequence |
| N-His/<br>SUMO | ATGGGTTCTAGCCACCATCATCATCATCACTCTT<br>CCGGTAGCGACAGCGAAGTCAATCAAGAGGCGA<br>AGCCTGAAGTTAAGCCAGAAGTCAAACCGGAAA<br>CGCACATTAACCTGAAAGTTTCGGATGGCTCAA<br>GCGAGATTTTCTTTAAGATCAAGAAAACCACGC<br>CGTTGCGTCGCCTGATGGAAGCGTTTGCCAAAC<br>GTCAGGGCAAAGAAATGGATTCCCTGCGCTTCC<br>TGTATGACGGCATCCGTATCCAGGCAGATCAAA<br>CGCCGGAAGATCTGGATATGGAAGATAACGACA<br>TTATTGAAGCGCACAGAGAGCAAATTGGTGGCA<br>GCGCGCGCAAAAAATACTCATGCGATTTCGAGA<br>CCACCACCGATCCGCTGGATTGTCGCGTGTGGGC<br>CTACGGCTACATGGAAATTGGCAAAGATAGCAA<br>TTATAAAATTGGCAACAGCCTGGATGAGTTCAT<br>GGAGTGGGTTAGCAAATGCAATGCGGATCTGTA<br>TTTTCACAACCTGCGTTTCGATGGCGAATTTATT<br>CTGATTTGGCTGCTGCAGAACGGCTTTAAATGGA<br>GCGATAAACGCAAACCGGAACCGATGACCTTTA<br>ACGGCGTGATTTCACGTGATAATGCGGTGTATCG<br>TTACGATATTTGCTATGGCTACACCAATAGCGGC<br>AAAAAAATTCACACCGTGATTTACGATAGCTAT<br>AAAAAACTGCCGTATCCGGTCAAAGTGATTGCG<br>AAAGCGTTCAACCTGACCCAGCTGAAAGGCGAT<br>ATTGATTACGATGCGTACCGCCCGGTGGGCCAT<br>AAAATTACCAAAGAAGAGTATAAATACATTTAT<br>AATGATATCAAAATCATTGCCGATGCCCTGAAA<br>ATTCAGTTTGAACAGGGCCTGAAAAAAATGACC<br>ATTGGAAGCGATTCACTGAACGGTTTTAAATCG | MGSSHHHHHHSSGSDSEVNQ<br>EAKPEVKPEVKPETHINLKVS<br>DGSSEIFFKIKKTTPLRRLMEA<br>FAKRQGKEMDSLRFLYDGIRI<br>QADQTPEDLDMEDNDIIEAH<br>REQIGGSARKKYSCDFETTTD<br>PLDCRVWAYGYMEIGKDSN<br>YKIGNSLDEFMEWVSKCNAD<br>LYFHNLRFDGEFILIWLLQNG<br>FKWSDKRKPEPMTFNGVISR<br>DNAVYRYDICYGYTNSGKKI<br>HTVIYDSYKKLPYPVKVIAKA<br>FNLTQLKGDIDYDAYRPVGH<br>KITKEEYKYIYNDIKIIADALK<br>IQFEQGLKKMTIGSDSLNGFK<br>SIFGKKQFEKTFPVLDMLTDD<br>FIRLSYKGGFTWLNPKFANIVI<br>NKGRVYDVNSMYPAIMYNE<br>LLPYGVPVRFKGKYEKDDKY<br>PLYIQQISCIFELKEGKIPMIQV<br>KNEPLKFKGSEYLTSSKGYEV<br>KLTLTNVELELFLENYKLNCV<br>EYLGGYKFRGVRGLFKTFIDK<br>WMNIKMNSEGAIRELAKLML<br>NNLYGKFATNPDVTGKYPEL<br>KEDGSLGFKMKPRELSEPVY<br>TAMGSFITAYGRCMTVRTGQ<br>SCYDRFIYADTDSVHVAGNE |

TABLE E1-continued

DNA and Amino Acid Sequences of N-His/SUMO and C-His/SET

| Construct | DNA sequence | Amino Acid Sequence |
|---|---|---|
| | ATTTTTGGCAAAAAACAGTTCGAAAAAAACCTTC<br>CCGGTGCTGGATATGCTGACCGATGATTTCATTC<br>GCCTGTCGTATAAAGGCGGCTTCACCTGGCTGA<br>ACCCGAAATTTGCCAACATTGTGATTAACAAAG<br>GCCGCGTGTATGATGTTAACAGCATGTACCCGG<br>CGATTATGTATAACGAACTGCTGCCGTATGGCGT<br>GCCGGTGCGCTTCAAAGGCAAATATGAAAAAGA<br>TGATAAATATCCGCTGTATATTCAGCAGATTAGC<br>TGCATTTTTGAACTGAAAGAAGGCAAAATTCCG<br>ATGATTCAGGTTAAAAACGAACCGCTGAAATTC<br>AAAGGCAGCGAATATCTGACCTCAAGCAAAGGT<br>TACGAAGTGAAACTGACCCTGACCAATGTGGAG<br>CTGGAACTGTTCCTCGAAAACTACAAACTGAAC<br>TGCGTGGAATATCTGGGCGGCTACAAATTTCGC<br>GGCGTGCGCGGCCTGTTTAAAACCTTTATTGATA<br>AATGGATGAACATTAAAATGAACAGCGAAGGCG<br>CCATTCGTGAACTGGCGAAACTGATGCTGAATA<br>ACCTGTATGGTAAATTTGCGACCAACCCGGATGT<br>GACGGGCAAATATCCGGAACTGAAAGAAGATGG<br>CAGCCTGGGCTTTAAAATGAAACCGCGCGAACT<br>GTCAGAACCGGTTTATACAGCGATGGGCAGCTT<br>TATTACCGCGTATGGCCGCTGCATGACCGTGCGC<br>ACCGGCCAGTCTTGCTACGATCGCTTTATTTATG<br>CGGATACCGATAGCGTGCATGTGGCGGGCAATG<br>AAGATATTCCGGAAATTGCGGATAAAATTGATA<br>GTAAAAAACTGGGCTACTGGGATCATGAAGCGA<br>CCTTTGAAACCGGCAAATATGTGCGCAGCAAGG<br>CGTATTTTCTGAACTTATACGCGAAAAAAGTGGT<br>GAAAGATGGCGAAGAAATTATTAAACCGTGCGG<br>CGAAGAAGAAGCAACCACCCGCAAACGTAAAGT<br>TGCCTGCGCGGGCATGCCGGAAACCCTGCGCAA<br>CATTGTGCCGTTCGAAGAATTTAAAATTGGCTAT<br>ACTGGTACCCGCCTGGCGCCGCGCCATGTTAAA<br>GGCGGCATTGTGCTGGTTGATGCGCCTTATACCC<br>TGAAAGAAGACATTTGGCGCTACGCC (SEQ ID<br>NO: 9) | DIPEIADKIDSKKLGYWDHEA<br>TFETGKYVRSKAYFLNLYAK<br>KVVKDGEEIIKPCGEEEATTR<br>KRKVACAGMPETLRNIVPFE<br>EFKIGYTGTRLAPRHVKGGIV<br>LVDAPYTLKEDIWRYA (SEQ<br>ID NO: 3) |
| C-His/<br>SET | ATGGCGCGCAAAAAATACTCATGCGATTTCG<br>AGACCACCACCGATCCGCTGGATTGTCGCGT<br>GTGGGCCTACGGCTACATGGAAATTGGCAA<br>AGATAGCAATTATAAAATTGGCAACAGCCT<br>GGATGAGTTCATGGAGTGGGTTAGCAAATG<br>CAATGCGGATCTGTATTTTCACAACCTGCGT<br>TTCGATGGCGAATTTATTCTGATTTGGCTGC<br>TGCAGAACGGCTTTAAATGGAGCGATAAAC<br>GCAAACCGGAACCGATGACCTTTAACGGCG<br>TGATTTCACGTGATAATGCGGTGTATCGTTA<br>CGATATTTGCTATGGCTACACCAATAGCGGC<br>AAAAAAATTCACACCGTGATTTACGATAGCT<br>ATAAAAAACTGCCGTATCCGGTCAAAGTGA<br>TTGCGAAAGCGTTCAACCTGACCCAGCTGAA<br>AGGCGATATTGATTACGATGCGTACCGCCCG<br>GTGGGCCATAAAATTACCAAAGAAGAGTAT<br>AAATACATTTATAATGATATCAAAATCATTG<br>CCGATGCCCTGAAAATTCAGTTTGAACAGGG<br>CCTGAAAAAAATGACCATTGGAAGCGATTC<br>ACTGAACGGTTTTAAATCGATTTTTGGCAAA<br>AAACAGTTCGAAAAAACCTTCCCGGGTGCTG<br>GATATGCTGACCGATGATTTCATTCGCCTGT<br>CGTATAAAGGCGGCTTCACCTGGCTGAACCC<br>GAAATTTGCCAACATTGTGATTAACAAAGGC<br>CGCGTGTATGATGTTAACAGCATGTACCCGG<br>CGATTATGTATAACGAACTGCTGCCGTATGG<br>CGTGCCGGTGCGCTTCAAAGGCAAATATGA<br>AAAAGATGATAAATATCCGCTGTATATTCAG<br>CAGATTAGCTGCATTTTTGAACTGAAAGAAG<br>GCAAAATTCCGATGATTCAGGTTAAAAACG<br>AACCGCTGAAATTCAAAGGCAGCGAATATC<br>TGACCTCAAGCAAAGGTTACGAAGTGAAAC<br>TGACCCTGACCAATGTGGAGCTGGAACTGTT<br>CCTCGAAAACTACAAACTGAACTGCGTGGA<br>ATATCTGGGCGGCTACAAATTTCGCGGCGTG<br>CGCGGCCTGTTTAAAACCTTTATTGATAAAT<br>GGATGAACATTAAAATGAACAGCGAAGGCG<br>CCATTCGTGAACTGGCGAAACTGATGCTGAA<br>TAACCTGTATGGTAAATTTGCGACCAACCCG | MARKKYSCDFETTTDPLDCR<br>VWAYGYMEIGKDSNYKIGNS<br>LDEFMEWVSKCNADLYFHNL<br>RFDGEFILIWLLQNGFKWSDK<br>RKPEPMTFNGVISRDNAVYR<br>YDICYGYTNSGKKIHTVIYDS<br>YKKLPYPVKVIAKAFNLTQL<br>KGDIDYDAYRPVGHKITKEE<br>YKYIYNDIKIIADALKIQFEQG<br>LKKMTIGSDSLNGFKSIFGKK<br>QFEKTFPVLDMLTDDFIRLSY<br>KGGFTWLNPKFANIVINKGR<br>VYDVNSMYPAIMYNELLPYG<br>VPVRFKGKYEKDDKYPLYIQ<br>QISCIFELKEGKIPMIQVKNEP<br>LKFKGSEYLTSSKGYEVKLTL<br>TNVELELFLENYKLNCVEYL<br>GGYKFRGVRGLFKTFIDKWM<br>NIKMNSEGAIRELAKLMLNN<br>LYGKFATNPDVTGKYPELKE<br>DGSLGFKMKPRELSEPVYTA<br>MGSFITAYGRCMTVRTGQSC<br>YDRFIYADTDSVHVAGNEDIP<br>EIADKIDSKKLGYWDHEATFE<br>TGKYVRSKAYFLNLYAKKVV<br>KDGEEIIKPCGEEEATTRKRK<br>VACAGMPETLRNIVPFEEFKI<br>GYTGTRLAPRHVKGGIVLVD<br>APYTLKEDIWRYAGGSHHHH<br>HHSEEDEEKEEDG (SEQ ID<br>NO: 7) |

TABLE E1-continued

DNA and Amino Acid Sequences of N-His/SUMO and C-His/SET

| Construct | DNA sequence | Amino Acid Sequence |
|---|---|---|
| | GATGTGACGGGCAAATATCCGGAACTGAAA | |
| | GAAGATGGCAGCCTGGGCTTTAAAATGAAA | |
| | CCGCGCGAACTGTCAGAACCGGTTTATACAG | |
| | CGATGGGCAGCTTTATTACCGCGTATGGCCG | |
| | CTGCATGACCGTGCGCACCGGCCAGTCTTGC | |
| | TACGATCGCTTTATTTATGCGGATACCGATA | |
| | GCGTGCATGTGGCGGGCAATGAAGATATTC | |
| | CGGAAATTGCGGATAAAATTGATAGTAAAA | |
| | AACTGGGCTACTGGGATCATGAAGCGACCTT | |
| | TGAAACCGGCAAATATGTGCGCAGCAAGGC | |
| | GTATTTTCTGAACTTATACGCGAAAAAAGTG | |
| | GTGAAAGATGGCGAAGAAATTATTAAACCG | |
| | TGCGGCGAAGAAGAAGCAACCACCCGCAAA | |
| | CGTAAAGTTGCCTGCGCGGGCATGCCGGAA | |
| | ACCCTGCGCAACATTGTGCCGTTCGAAGAAT | |
| | TTAAAATTGGCTATACTGGTACCCGCCTGGC | |
| | GCCGCGCCATGTTAAAGGCGGCATTGTGCTG | |
| | GTTGATGCGCCTTATACCCTGAAAGAAGACA | |
| | TTTGGCGCTACGCCGGTGGCTCACATCACCA | |
| | CCATCATCATTCAGAAGAGGACGAAGAGAA | |
| | AGAAGAGGACGGGTAATGAGGTTGA (SEQ | |
| | ID NO: 8) | |

The culture was centrifuged, and the cell pellet was resuspended in lysis buffer. The lysate was centrifuged at a high speed to obtain a soluble and insoluble fraction. Samples were run on an SDS-PAGE for protein solubility analysis, as shown in FIG. 1. As shown in FIG. 1, the N-His/SUMO recombinant PumA1 produced a doublet with a first band at the expected size of approximately 80 kDa, and a smaller band at approximately 75 kDa. The C-His/SET recombinant PumA1 produced a single band at the expected size of approximately 70 kDa. As shown in FIG. 1, both N-His/SUMO and C-His/SET recombinant PumA1 were at least about 90% soluble. Additionally, the majority of both recombinant PumA1 polypeptides remained in the PEI supernatant (lane 5 on both blots), rather than the PEI pellet, indicating that the majority of PumA1 was stable.

Example 2: Heparin Purification of Recombinant PumA1

This example demonstrates purification of N-His/SUMO or C-His/SET recombinant PumA1.

Figure 2:
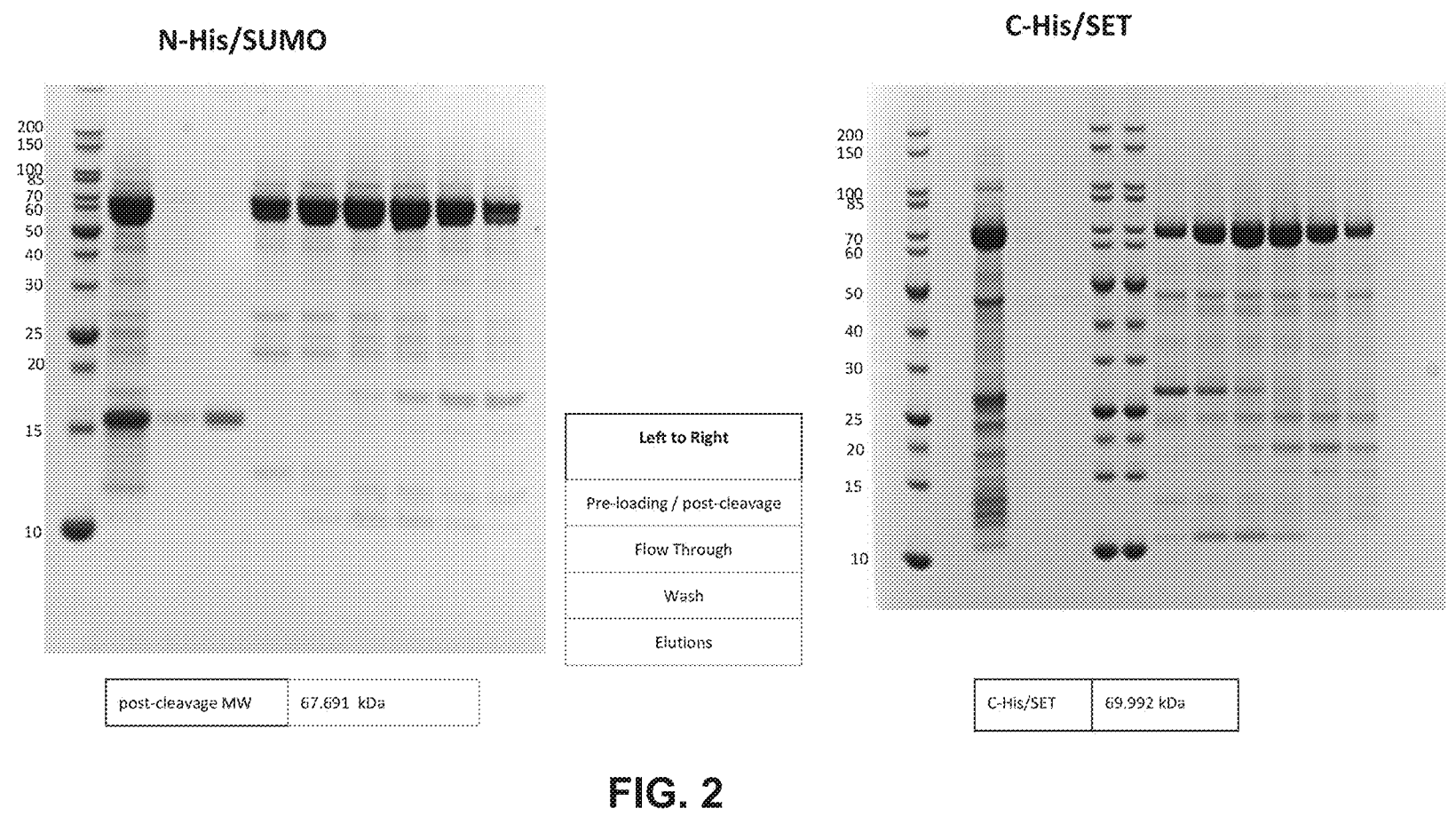

N-His/SUMO or C-His/SET recombinant PumA1 polypeptides were expressed as described in Example 1. The soluble fraction was collected and run on a heparin column. Fractions were collected for pre-loading (post-cleavage for the N-His/SUMO vector), flow-through, wash, and six elution fractions, as shown in FIG. 2. Each elution fraction was collected as 1 mL aliquots using an 80-100% gradient of 1 M NaCl. As shown in FIG. 2, eluted fractions of the cleaved N-His/SUMO recombinant PumA1 produced a doublet band running at approximately 68 kDa, indicating that the doublet is retained with heparin purification. Eluted fractions of the C-His/SET recombinant PumA1 produced a single band at approximately 70 kDa.

Minor impurities at lower molecular weights were present at low concentrations and could be removed by an additional Nickel chromatography step, or by using a 50 kDa MWCO concentrator.

Example 3: Characterization of Recombinant PumA1 Polymerase Activity in an In Vitro Rolling Circle Amplification Assay This example demonstrates that the recombinant PumA1 polypeptides had a slower rate of amplification, but pro- duced more rolling circle products (RCPs), compared to the Phi29 polymerase control, in an in vitro rolling circle amplification (RCA) assay. An RCA reaction mixture containing the polymerase, polymerase reaction buffer, dNTP, BSA, and SYBR Gold was prepared. The reactions were performed under Phi29-optimized conditions (NEB Phi29 buffer, containing 50 mM Tris-Cl, pH 7.5, 10 mM $MgCl_2$, 10 mM $NH_4SO_4$, 4 mM DTT, 0.2 mM dNTPs, 0.2 mg/mL BSA; reactions performed at 37° C.).

Figure 3:
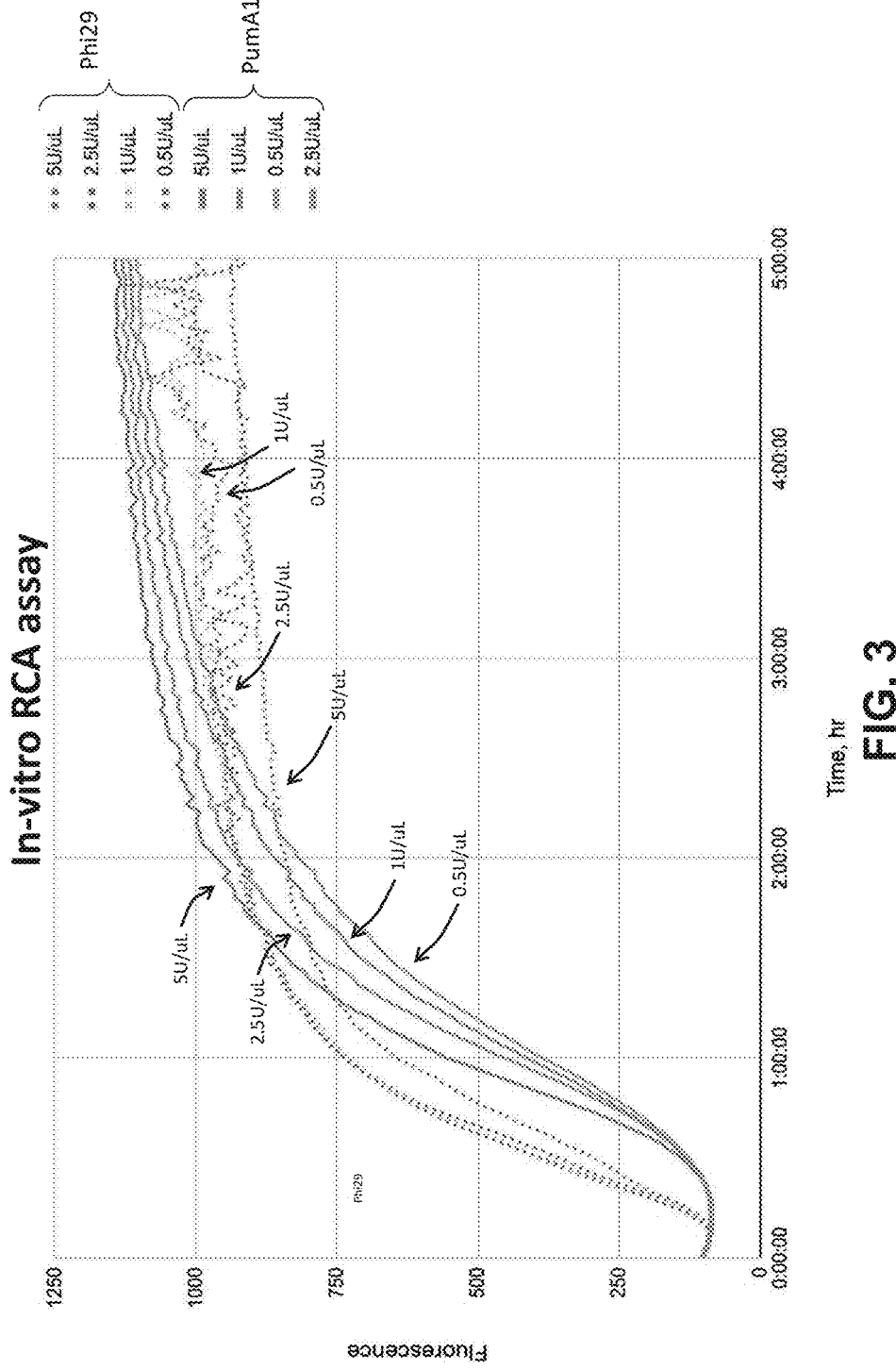
FIG. 3 depicts results from an in situ rolling circle amplification (RCA) assay comparing the activities of a wild-type (WT) Phi29 and an exemplary recombinant PumA1 polymerase. Shown in the figure is a fluorescence intensity readout for the amount of rolling circle products (RCPs) generated by amplification.

After RCA was initiated, SYBR Gold incorporation was monitored in real-time for 5 hours, followed by polymerase inactivation. Varying concentrations from 0.5 U/μL-5 U/μL of either Phi29 or recombinant PumA1 (C-His/SET PumA1) were used (the same unit definition was used for the polymerases). As shown in FIG. 3, the exponential phase of amplification for all concentrations of the recombinant PumA1 polypeptide began later than that of Phi29, suggesting that recombinant PumA1 had a slower RCA rate. However, the fluorescence intensity for all concentrations of recombinant PumA1 plateaued at a higher fluorescence intensity readout than that of Phi29, indicating that recombinant PumA1 produced more RCPs.

Example 4: Characterization of Recombinant PumA1 Activity in a Tissue Sample

An exemplary recombinant PumA1 polypeptide was next tested in an in situ rolling circle amplification assay in a tissue sample. This example demonstrates that a recombinant PumA1 polymerase produces a larger number of detectable RCPs than Phi29 in an RCA assay performed in a tissue sample, and that the detectable spots for the RCPs were smaller and slightly dimmer than those produced by Phi29.

A tissue sample was obtained and cryosectioned onto a glass slide for processing. The tissue was fixed by incubating in 3.7% paraformaldehyde (PFA) and permeabilized. To prepare for probe hybridization, a wash buffer was added to the tissue section. Circularizable probes were hybridized to target nucleic acids in the tissue sample and ligated to form circular templates for RCA. Rolling circle amplification was then performed using a primer and one of two different recombinant PumA1 polypeptides (a recombinant PumA1 without a heterologous tag (referred to as "PumA1") and C-His/SET PumA1) or Phi29. The sample was contacted with the respective polymerase and incubated under conditions optimized for Phi29, as described in Example 2 above. A fluorescently labeled probe capable of hybridizing to a common sequence in the RCPs was added to the sample and the sample was washed to remove unbound probe. The sample was then imaged to determine the size, intensity, and number of detectable spots (corresponding to detectable RCPs).

Figure 4:
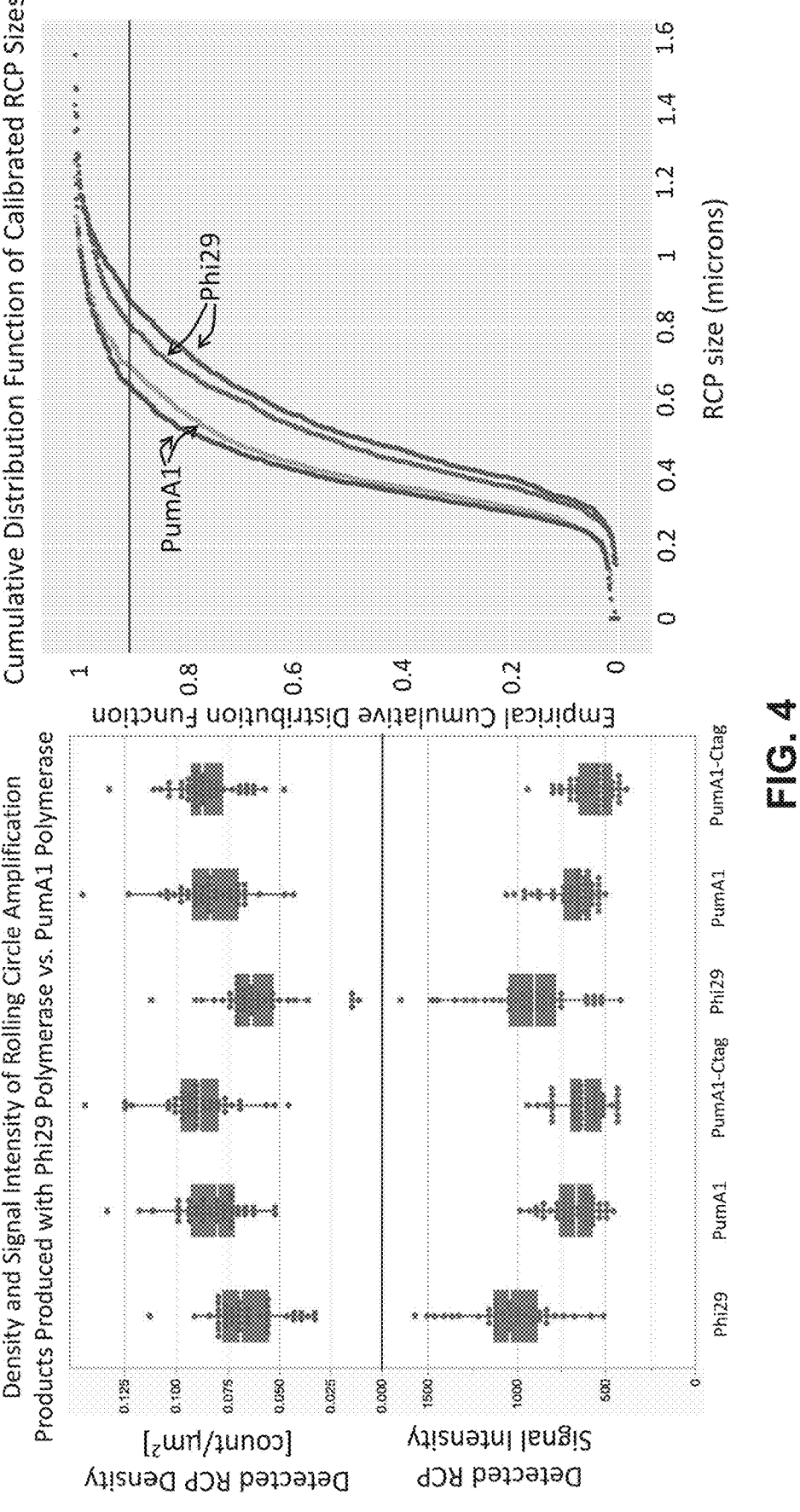
FIG. 4 depicts results from an in situ rolling circle amplification (RCA) assay comparing the activities of a wild-type (WT) Phi29 and an exemplary recombinant PumA1 polymerase in a tissue sample. Shown in the figure are signal density and signal intensity of rolling circle products (RCPs) generated by amplification.

As shown in FIG. 4, left panel, the detected object density was higher for both PumA1 and C-His/SET PumA1 compared to Phi29, suggesting recombinant PumA1 provides higher sensitivity in an RCA assay performed in situ in a tissue sample. The detected object signal intensity mean was lower for both PumA1 and C-his/SET PumA1, demonstrating that the use of a recombinant PumA1 polypeptide resulted in RCPs that are dimmer compared to Phi29-dependent RCA products (FIG. 4, left panel). As shown in FIG. 4, right panel, a recombinant PumA1 polypeptide also produced smaller RCPs compared to Phi29. In some aspects, smaller RCP sizes may be advantageous for RCA-based assays (e.g., to reduce optical crowding and facilitate resolution of individual RCP spots).

Example 5: Improved Buffer for Nucleic Acid Amplification by PumA1 Polymerase This example demonstrates the development of an RCA buffer with improved characteristics for nucleic acid amplification using a recombinant PumA1 polymerase polypeptide. NEB's Phi29 buffer (50 mM Tris-Cl pH 7.5, 10 mM $MgCl_2$, 10 mM $NH_4SO_4$, 4 mM DTT, 0.2 mM dNTPs, 0.2 mg/mL BSA) was used as a starting point for developing an improved buffer. Aside from the original recipe of the NEB Phi29 buffer, PumA1 enzyme and KCl were included in the buffers tested.

Different buffer conditions were tested by changing a single variable (dNTP concentration, $MgCl_2$ concentration, enzyme concentration, KCl concentration, DTT concentration, and $NH_4SO_4$ concentration) while maintaining other variables constant according to NEB's Phi29 buffer.

Figure 5A:
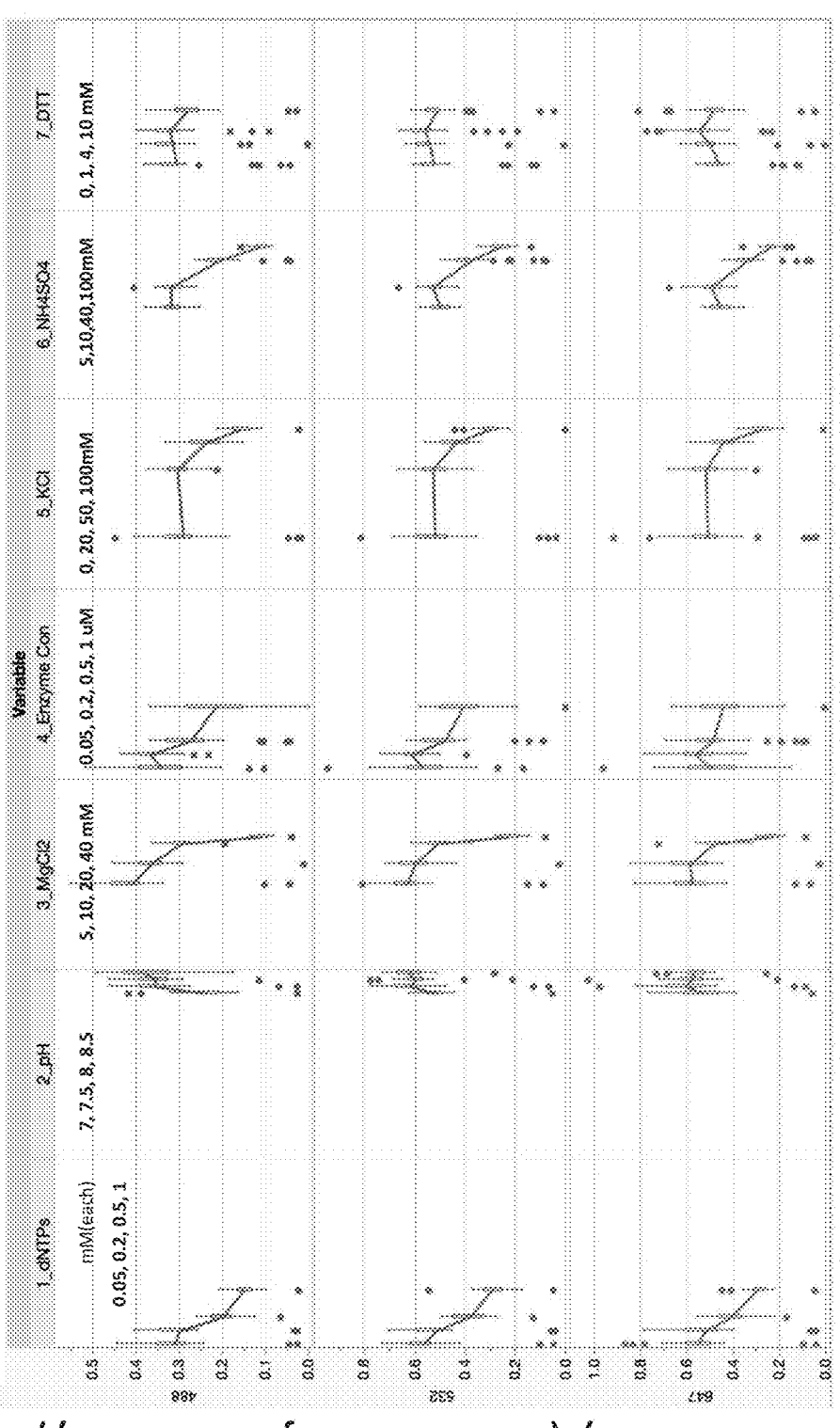
FIGS. 5A-5B depict the results of the optimization conditions for an RCA buffer specific for C-His/SET recombinant PumA1 polymerase.
Figure 5B:
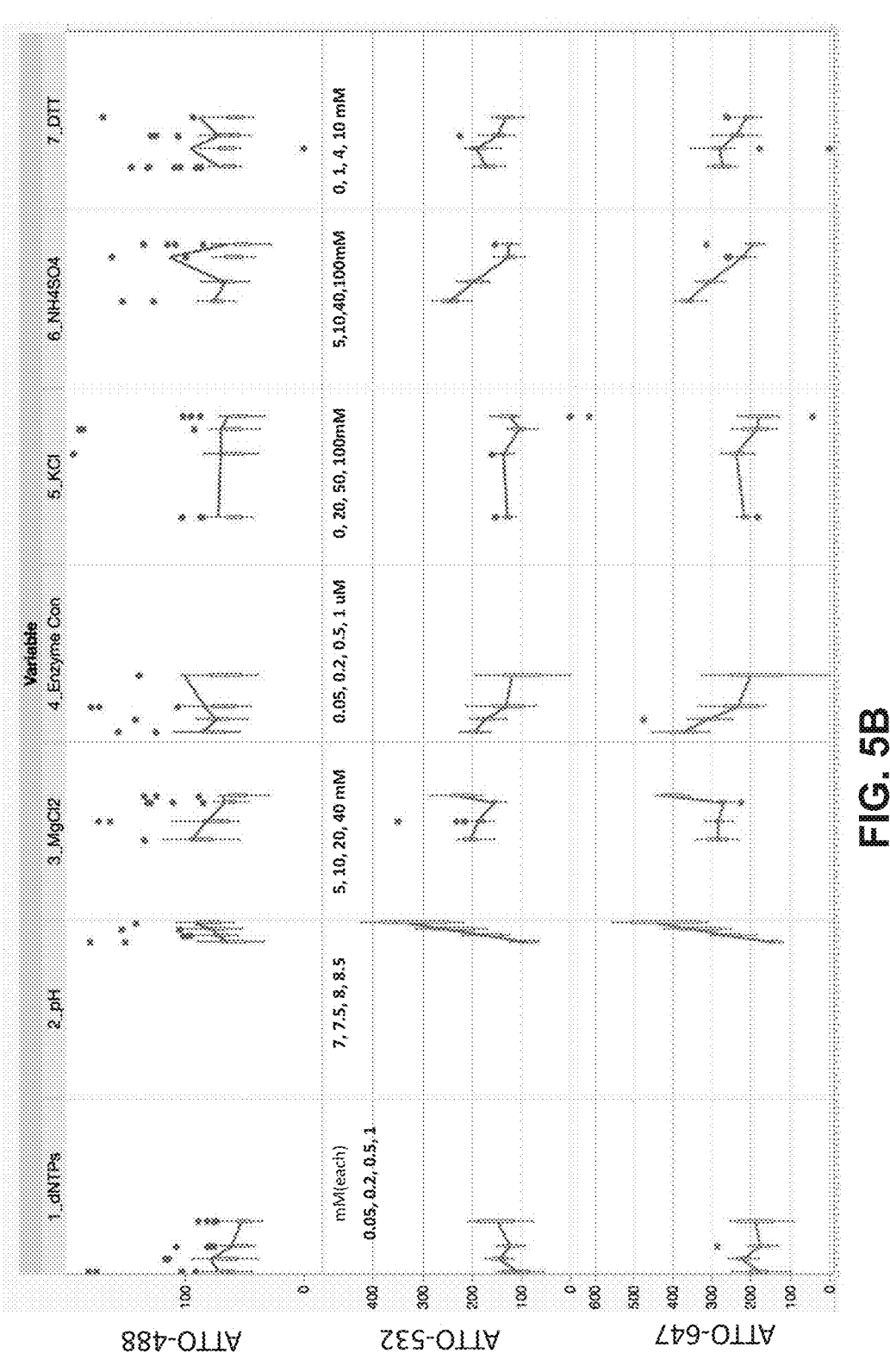

Each buffer was tested in an in situ RCA assay for 3 wells of a 96-well plate seeded with NIH 3T3 cells. Prior to RCA, circularizable probes were hybridized to target nucleic acids in the cells and ligated to form circular templates for RCA. RCA was then performed using PumA1 polymerase under each of the conditions indicated in Table E2. Three different fluorescently labeled probes were hybridized to a common sequence in the RCPs, and each experimental condition was measured for detected RCP density (reflecting sensitivity of an RCA-based assay) and signal intensity with dyes detected in three different channels (488 nm, 532 nm, and 647 nm). FIG. 5A shows the sensitivity of the RCA assay in the different buffers (detected RCP density). FIG. 5B signal intensities of detected RCPs for each condition. Based on the results shown in FIGS. 5A-5B, three improved buffers were selected for further characterization (Table E2).

TABLE E2

| Improved buffers for PumA1 RCA | | |
|---|---|---|
| Buffer1 | Buffer2 | Buffer3 |
| 50 mM Tris-Cl, pH 8.5 | 50 mM Tris-Cl, pH 8.5 | 50 mM Tris-Cl, pH 8.5 |
| 10 mM MgCl2 | 10 mM MgCl2 | 5 mM MgCl2 |
| 10 mM NH4S04 | 10 mM NH4S04 | 10 mM NH4S04 |
| 4 mM DTT | 1 mM DTT | 1 mM DTT |
| 0.2 mM dNTPs | 0.1 mM dNTPs | 0.2 mM dNTPs |
| 0.2 mg/mL BSA | 0.2 mg/mL BSA | 0.2 mg/mL BSA |

Example 6: Detection of Nucleic Acids In Situ Using Improved Buffers for PumA1

This example demonstrates that the three improved buffers for a recombinant PumA1 polymerase polypeptide (Buffer1, Buffer2, and Buffer3) described in Example 5 can be used in RCA assays to comparably or better detect nucleic acids than RCA assays performed with Phi29 and its standard buffer (Phi29_SOP). An in situ RCA assay was performed on fresh frozen mouse brain tissue to compare the detection of nucleic acids by PumA1 and the optimized buffers, compared to the Phi29 control. Recombinant PumA1 polymerase in Buffer2 and Buffer3 yielded a higher fraction of objects decoded with quality score>=20 and assigned to a cell, whereas Buffer1 was half the fraction of the Phi29 control, as shown in Table E3 below. While the recombinant PumA1 polymerase in Buffer1 yielded a similar number of median transcripts per non-empty cell as the Phi29 control, recombinant PumA1 polymerase in Buffer2 or Buffer3 led to higher median transcripts. Additionally, all three optimized buffers resulted in higher total objects detected, compared to control.

TABLE E3

| Characterization of PumA1 RCA activity in tissue samples using optimized buffers | | | | |
|---|---|---|---|---|
| Metric | Phi29_SOP | PumA1 Buffer1 | PumA1 Buffer2 | PumA1 Buffer3 |
| Fraction of objects decoded with quality score >=20 and assigned to a cell | 0.139 | 0.075 | 0.182 | 0.187 |
| Fraction of objects that are assigned to a cell | 0.925 | 0.826 | 0.878 | 0.841 |
| Mean transcripts per non-empty cell | 18.698 | 16.828 | 26.587 | 31.424 |
| Median transcripts per cell | 12 | 12 | 21 | 23 |
| Median transcripts per non-empty cell | 14 | 13 | 21 | 24 |
| Number of cells detected | 11,011 | 10,373 | 10,543 | 10,895 |
| Total objects detected | 1,365,217 | 2,260,255 | 1,524,426 | 1,801,054 |

Example 7: Variant PumA1 I545E/A574S/P575V Polymerase Shows Higher Thermostability, Density, and Signal Intensity This example demonstrates that a PumA1 polymerase comprising amino acid substitutions I545E, A574S, P575V (abbreviated as PumA1-ESV, wherein the numbering is based on SEQ ID NO:1) showed higher thermostability in an in vitro RCA assay and produced denser and brighter RCPs in an RCA assay performed in a tissue sample compared to a wild-type PumA1 polymerase.

Figure 6:
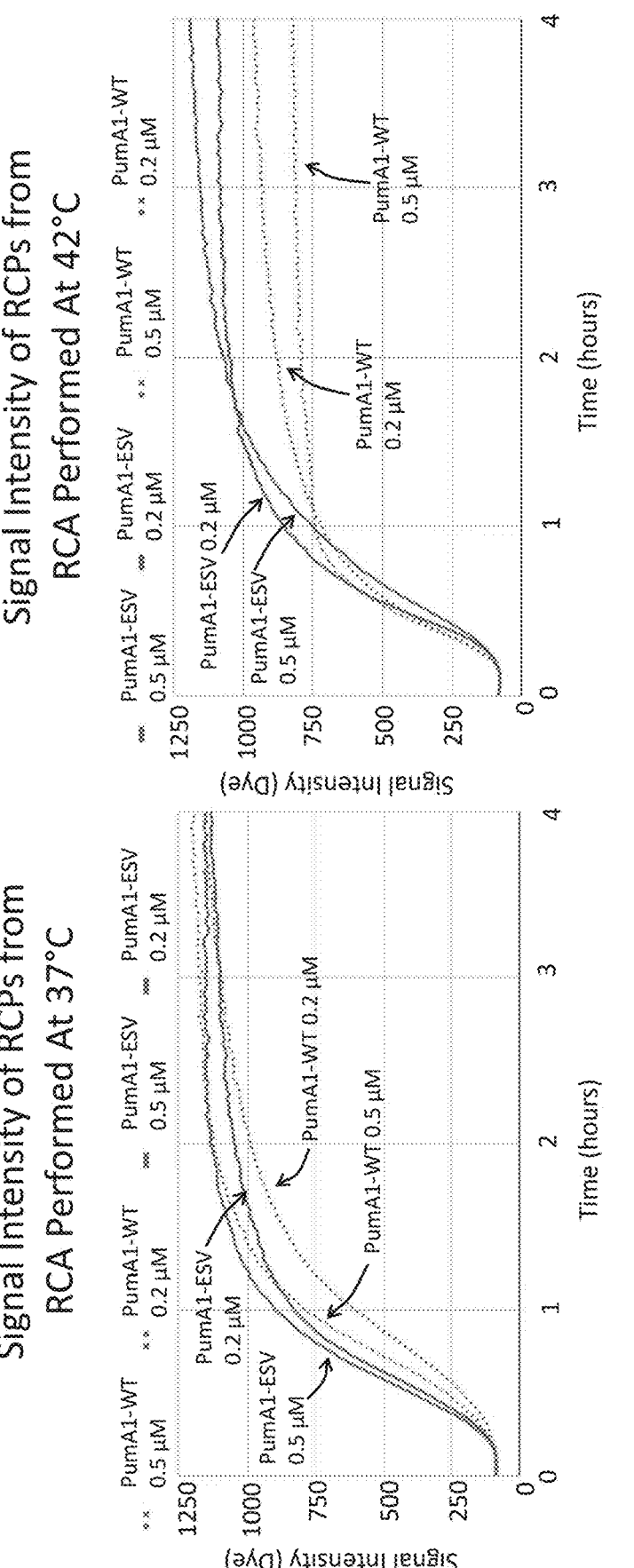
FIG. 6 depicts results for signal intensity from an in situ rolling circle amplification (RCA) assay comparing the thermostability of a wild-type (WT) recombinant PumA1 polymerase and an exemplary variant PumA1 polymerase ("PumA1-ESV," comprising I545E, A574S, P575V substitutions, wherein the amino acid numbering is based on SEQ ID NO:1). RCA assays were performed at 37° C. and 42° C. using tissue samples with two concentrations of polymerase (0.2μ M or 0.5 μM).

In an in vitro RCA assay, PumA1-ESV displayed better signal intensity at 37° C. at the initial stages of amplification and was similar to wildtype PumA1 (PumA1-WT) control overall whereas at 42° C., PumA1-ESV signal intensity was similar to PumA1-WT control in the exponential amplification step, but was significantly improved once amplification had plateaued (FIG. 6). These results demonstrate that PumA1-ESV had better thermostability at 42° C. than PumA1-WT.

Figure 7:
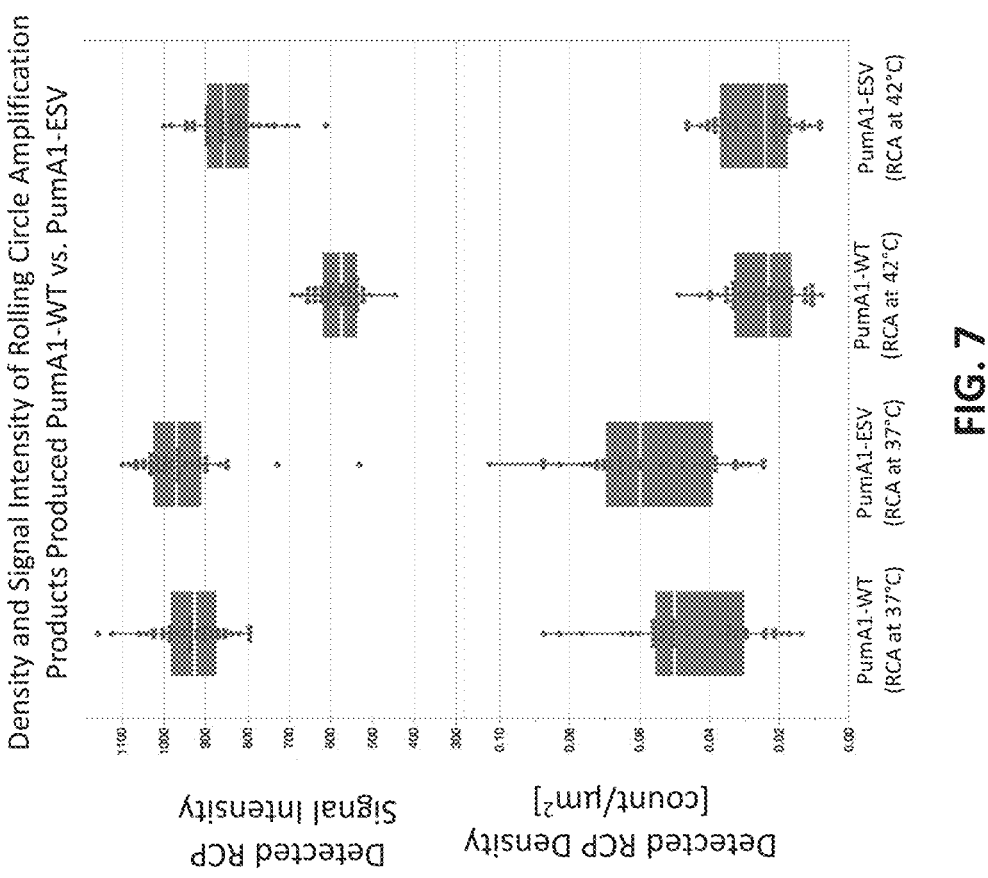
FIG. 7 depicts results from an in situ rolling circle amplification (RCA) assay comparing the signal intensity and quantity for of rolling circle products (RCPs) of a wild-type ("PumA1-WT") recombinant PumA1 polymerase and an exemplary variant recombinant PumA1 polymerase "PumA1-ESV" (I545E, A574S, P575V). RCA assays were performed at 37° C. and 42° C. using tissue samples.

In an RCA assay performed in tissue sections, at 37° C., PumA1-ESV had slightly higher signal intensity as quantified by the box plot, and produced an increased density of RCPs. At 42° C., PumA1-ESV had significantly higher signal intensity and comparable number of RCPs, compared to PumA1-WT (FIG. 7).

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | MARKKYSCDFETTTDPLDCRVWAYGYMEIGKDSNYKIGNSLDEFMEWVSK CNADLYFHNLREDGEFILIWLLQNGFKWSDKRKPEPMTENGVISRDNAVY RYDICYGYTNSGKKIHTVIYDSYKKLPYPVKVIAKAFNLTQLKGDIDYDA YRPVGHKITKEEYKYIYNDIKIIADALKIQFEQGLKKMTIGSDSLNGEKS IFGKKQFEKTFPVLDMLTDDFIRLSYKGGFTWLNPKFANIVINKGRVYDV NSMYPAIMYNELLPYGVPVRFKGKYEKDDKYPLYIQQISCIFELKEGKIP MIQVKNEPLKFKGSEYLTSSKGYEVKLTLTNVELELFLENYKLNCVEYLG GYKFRGVRGLFKTFIDKWMNIKMNSEGAIRELAKLMLNNLYGKFATNPDV TGKYPELKEDGSLGFKMKPRELSEPVYTAMGSFITAYGRCMTVRTGQSCY DRFIYADTDSVHVAGNEDIPEIADKIDSKKLGYWDHEATFETGKYVRSKA YFLNLYAKKVVKDGEEIIKPCGEEEATTRKRKVACAGMPETLRNIVPFEE FKIGYTGTRLAPRHVKGGIVLVDAPYTLKEDIWRYA | PumA1 Protein including N-terminal met |
| 2 | ARKKYSCDFETTTDPLDCRVWAYGYMEIGKDSNYKIGNSLDEFMEWVSKC NADLYFHNLREDGEFILIWLLQNGFKWSDKRKPEPMTENGVISRDNAVYR YDICYGYTNSGKKIHTVIYDSYKKLPYPVKVIAKAFNLTQLKGDIDYDAY RPVGHKITKEEYKYIYNDIKIIADALKIQFEQGLKKMTIGSDSLNGFKSI FGKKQFEKTFPVLDMLTDDFIRLSYKGGFTWLNPKFANIVINKGRVYDVN SMYPAIMYNELLPYGVPVRFKGKYEKDDKYPLYIQQISCIFELKEGKIPM IQVKNEPLKFKGSEYLTSSKGYEVKLTLTNVELELFLENYKLNCVEYLGG YKFRGVRGLFKTFIDKWMNIKMNSEGAIRELAKLMLNNLYGKFATNPDVT GKYPELKEDGSLGFKMKPRELSEPVYTAMGSFITAYGRCMTVRTGQSCYD RFIYADTDSVHVAGNEDIPEIADKIDSKKLGYWDHEATFETGKYVRSKAY FLNLYAKKVVKDGEEIIKPCGEEEATTRKRKVACAGMPETLRNIVPFEEF KIGYTGTRLAPRHVKGGIVLVDAPYTLKEDIWRYA | PumA1 Protein without N-terminal met |
| 3 | MGSSHHHHHHSSGSDSEVNQEAKPEVKPEVKPETHINLKVSDGSSEIFFK IKKTTPLRRLMEAFAKRQGKEMDSLRFLYDGIRIQADQTPEDLDMEDNDI IEAHREQIGGSARKKYSCDFETTTDPLDCRVWAYGYMEIGKDSNYKIGNS LDEFMEWVSKCNADLYFHNLREDGEFILIWLLQNGFKWSDKRKPEPMTEN GVISRDNAVYRYDICYGYTNSGKKIHTVIYDSYKKLPYPVKVIAKAFNLT QLKGDIDYDAYRPVGHKITKEEYKYIYNDIKIIADALKIQFEQGLKKMTI GSDSLNGFKSIFGKKQFEKTFPVLDMLTDDFIRLSYKGGFTWLNPKFANI VINKGRVYDVNSMYPAIMYNELLPYGVPVRFKGKYEKDDKYPLYIQQISC IFELKEGKIPMIQVKNEPLKFKGSEYLTSSKGYEVKLTLTNVELELFLEN YKLNCVEYLGGYKFRGVRGLFKTFIDKWMNIKMNSEGAIRELAKLMLNNL YGKFATNPDVTGKYPELKEDGSLGFKMKPRELSEPVYTAMGSFITAYGRC MTVRTGQSCYDRFIYADTDSVHVAGNEDIPEIADKIDSKKLGYWDHEATF ETGKYVRSKAYFLNLYAKKVVKDGEEIIKPCGEEEATTRKRKVACAGMPE TLRNIVPFEEFKIGYTGTRLAPRHVKGGIVLVDAPYTLKEDIWRYA | N-His/SUMO |
| 4 | SSG | Linker |
| 5 | HHHHHH | His-tag |
| 6 | SDSEVNQEAKPEVKPEVKPETHINLKVSDGSSEIFFKIKKTTPLRRLMEA FAKRQGKEMDSLRFLYDGIRIQADQTPEDLDMEDNDIIEAHREQIGGS | SUMO tag |
| 7 | MARKKYSCDFETTTDPLDCRVWAYGYMEIGKDSNYKIGNSLDEFMEWVSK CNADLYFHNLREDGEFILIWLLQNGEKWSDKRKPEPMTENGVISRDNAVY RYDICYGYTNSGKKIHTVIYDSYKKLPYPVKVIAKAFNLTQLKGDIDYDA YRPVGHKITKEEYKYIYNDIKIIADALKIQFEQGLKKMTIGSDSLNGFKS IFGKKQFEKTFPVLDMLTDDFIRLSYKGGFTWLNPKFANIVINKGRVYDV | C-HIS/SET |

-continued

| SEQUENCES | | |
|---|---|---|
| SEQ ID NO. | SEQUENCE | DESCRIPTION |

NSMYPAIMYNELLPYGVPVREKGKYEKDDKYPLYIQQISCIFELKEGKIP
MIQVKNEPLKFKGSEYLTSSKGYEVKLTLTNVELELFLENYKLNCVEYLG
GYKFRGVRGLFKTFIDKWMNIKMNSEGAIRELAKLMLNNLYGKFATNPDV
TGKYPELKEDGSLGFKMKPRELSEPVYTAMGSFITAYGRCMTVRTGQSCY
DRFIYADTDSVHVAGNEDIPEIADKIDSKKLGYWDHEATFETGKYVRSKA
YFLNLYAKKVVKDGEEIIKPCGEEEATTRKRKVACAGMPETLRNIVPFEE
FKIGYTGTRLAPRHVKGGIVLVDAPYTLKEDIWRYAGGSHHHHHHSEEDE
EKEEDG 8        atggcgcgcaaaaaatactcatgcgatttcgagaccaccaccgatccgct        C-His/SET
         ggattgtcgcgtgtgggcctacggctacatggaaattggcaaagatagca        coding
         attataaaattggcaacagcctggatgagttcatggagtgggttagcaaa        sequence
         tgcaatgcggatctgtattttcacaacctgcgtttcgatggcgaatttat
         tctgatttggctgctgcagaacggctttaaatggagcgataaacgcaaac
         cggaaccgatgacctttaacggcgtgatttcacgtgataatgcggtgtat
         cgttacgatatttgctatggctacaccaatagcggcaaaaaaattcacac
         cgtgatttacgatagctataaaaaactgccgtatccggtcaaagtgattg
         cgaaagcgttcaacctgacccagctgaaaggcgatattgattacgatgcg
         taccgcccggtgggccataaaattaccaaagaagagtataaatacattta
         taatgatatcaaaatcattgccgatgccctgaaaattcagtttgaacagg
         gcctgaaaaaaatgaccattggaagcgattcactgaacggttttaaatcg
         atttttggcaaaaaacagttcgaaaaaaaccttcccggtgctggatatgct
         gaccgatgatttcattcgcctgtcgtataaaggcggcttcacctggctga
         acccgaaatttgccaacattgtgattaacaaaggccgcgtgtatgatgtt
         aacagcatgtaccggcgattatgtataacgaactgctgccgtatggcgt
         gccggtgcgcttcaaaggcaaatatgaaaaagatgataaatatccgctgt
         atattcagcagattagctgcatttttgaactgaaagaaggcaaaattccg
         atgattcaggttaaaaacgaaccgctgaaattcaaaggcagcgaatatct
         gacctcaagcaaaggttacgaagtgaaactgaccctgaccaatgtggagc
         tggaactgttcctcgaaaactacaaactgaactgcgtggaatatctgggc
         ggctacaaatttcgcggcgtgcgcggcctgtttaaaacctttattgataa
         atggatgaacattaaaatgaacagcgaaggcgccattcgtgaactggcga
         aactgatgctgaataacctgtatggtaaatttgcgaccaacccggatgtg
         acgggcaaatatccggaactgaaagaagatggcagcctgggctttaaaat
         gaaaccgcgcgaactgtcagaaccggtttatacagcgatgggcagcttta
         ttaccgcgtatggccgctgcatgaccgtgcgcaccggccagtcttgctac
         gatcgctttatttatgcggataccgatagcgtgcatgtggcgggcaatga
         agatattccggaaattgcggataaaattgatagtaaaaaactgggctact
         gggatcatgaagcgacctttgaaaccggcaaatatgtgcgcagcaaggcg
         tattttctgaacttatacgcgaaaaaagtggtgaaagatggcgaagaaat
         tattaaaccgtgcggcgaagaagaagcaaccacccgcaaacgtaaagttg
         cctgcgcgggcatgccggaaaccctgcgcaacattgtgccgttcgaagaa
         tttaaaattggctatactggtacccgcctggcgccgcgccatgttaaagg
         cggcattgtgctggttgatgcgccttatacccctgaaagaagacatttggc
         gctacgccggtggctcacatcaccaccatcatcattcagaagaggacgaa
         gagaaagaagaggacgggtaatgaggttga 9        ATGGGTTCTAGCCACCATCATCATCATCATCACTCTTCCGGTAGCGACAGCGA        N-HIS/SUMO
         AGTCAATCAAGAGGCGAAGCCTGAAGTTAAGCCAGAAGTCAAACCGGAAA        coding
         CGCACATTAACCTGAAAGTTTCGGATGGCTCAAGCGAGATTTTCTTTAAG        sequence
         ATCAAGAAACCACGCCGTTGCGTCGCCTGATGGAAGCGTTTGCCAAACG
         TCAGGGCAAAGAAATGGATTCCCTGCGCTTCCTGTATGACGGCATCCGTA
         TCCAGGCAGATCAAACGCCGGAAGATCTGGATATGGAAGATAACGACATT
         ATTGAAGCGCACAGAGAGCAAATTGGTGGCAGCGCGCGCAAAAAATACTC
         ATGCGATTTCGAGACCACCACCGATCCGCTGGATTGTCGCGTGTGGGCCT
         ACGGCTACATGGAAATTGGCAAAGATAGCAATTATAAAATTGGCAACAGC
         CTGGATGAGTTCATGGAGTGGGTTAGCAAATGCAATGCGGATCTGTATTT
         TCACAACCTGCGTTTCGATGGCGAATTTATTCTGATTTGGCTGCTGCAGA
         ACGGCTTTAAATGGAGCGATAAACGCAAACCGGAACCGATGACCTTTAAC
         GGCGTGATTTCACGTGATAATGCGGTGTATCGTTACGATATTTGCTATGG
         CTACACCAATAGCGGCAAAAAAATTCACACCGTGATTTACGATAGCTATA
         AAAAACTGCCGTATCCGGTCAAAGTGATTGCGAAAGCGTTCAACCTGACC
         CAGCTGAAAGGCGATATTGATTACGATGCGTACCGCCCGGTGGGCCATAA
         AATTACCAAAGAAGAGTATAAATACATTTATAATGATATCAAAATCATTG
         CCGATGCCCTGAAAATTCAGTTTGAACAGGGCCTGAAAAAAATGACCATT
         GGAAGCGATTCACTGAACGGTTTTAAATCGATTTTTGGCAAAAAACAGTT
         CGAAAAAACCTTCCCGGTGCTGGATATGCTGACCGATGATTTCATTCGCC
         TGTCGTATAAAGGCGGCTTCACCTGGCTGAACCCGAAATTTGCCAACATT
         GTGATTAACAAAGGCCGCGTGTATGATGTTAACAGCATGTACCCGGCGAT
         TATGTATAACGAACTGCTGCCGTATGGCGTGCCGGTGCGCTTCAAAGGCA
         AATATGAAAAAGATGATAAATATCCGCTGTATATTCAGCAGATTAGCTGC
         ATTTTTGAACTGAAAGAAGGCAAAATTCCGATGATTCAGGTTAAAAACGA
         ACCGCTGAAATTCAAAGGCAGCGAATATCTGACCTCAAGCAAAGGTTACG
         AAGTGAAACTGACCCTGACCAATGTGGAGCTGGAACTGTTCCTCGAAAAC -continued

| | SEQUENCES | |
|---|---|---|
| SEQ ID NO. | SEQUENCE | DESCRIPTION |
| | TACAAACTGAACTGCGTGGAATATCTGGGCGGCTACAAATTTCGCGGCGT GCGCGGCCTGTTTAAAACCTTTATTGATAAATGGATGAACATTAAAATGA ACAGCGAAGGCGCCATTCGTGAACTGGCGAAACTGATGCTGAATAACCTG TATGGTAAATTTGCGACCAACCCGGATGTGACGGGCAAATATCCGGAACT GAAAGAAGATGGCAGCCTGGGCTTTAAAATGAAACCGCGCGAACTGTCAG AACCGGTTTATACAGCGATGGGCAGCTTTATTACCGCGTATGGCCGCTGC ATGACCGTGCGCACCGGCCAGTCTTGCTACGATCGCTTTATTTATGCGGA TACCGATAGCGTGCATGTGGCGGGCAATGAAGATATTCCGGAAATTGCGG ATAAAATTGATAGTAAAAAACTGGGCTACTGGGATCATGAAGCGACCTTT GAAACCGGCAAATATGTGCGCAGCAAGGCGTATTTTCTGAACTTATACGC GAAAAAAGTGGTGAAAGATGGCGAAGAAATTATTAAACCGTGCGGCGAAG AAGAAGCAACCACCCGCAAACGTAAAGTTGCCTGCGCGGGCATGCCGGAA ACCCTGCGCAACATTGTGCCCGTTCGAAGAATTTAAAATTGGCTATACTGG TACCCGCCTGGCGCCGCGCCATGTTAAAGGCGGCATTGTGCTGGTTGATG CGCCTTATACCCTGAAAGAAGACATTTGGCGCTACGCC | |
| 10 | ARKKYSCDFETTTDPLDCRVWAYGYMEIGKDSNYKIGNSLDEFMEWVSKC NADLYFHNLREDGEFILIWLLQNGEKWSDKRKPEPMTENGVISRDNAVYR YDICYGYTNSGKKIHTVIYDSYKKLPYPVKVIAKAFNLTQLKGDIDYDAY RPVGHKITKEEYKYIYNDIKIIADALKIQFEQGLKKMTIGSDSLNGEKSI FGKKQFEKTFPVLDMLTDDFIRLSYKGGFTWLNPKFANIVINKGRVYDVN SMYPAIMYNELLPYGVPVREKGKYEKDDKYPLYIQQISCIFELKEGKIPM IQVKNEPLKFKGSEYLTSSKGYEVKLTLTNVELELFLENYKLNCVEYLGG YKFRGVRGLFKTFIDKWMNIKMNSEGAIRELAKLMLNNLYGKFATNPDVT GKYPELKEDGSLGFKMKPRELSEPVYTAMGSFITAYGRCMTVRTGQSCYD RFIYADTDSVHVAGNEDIPEIADKIDSKKLGYWDHEATFETGKYVRSKAY FLNLYAKKVVKDGEEIIKPCGEEEATTRKRKVACAGMPETLRNEVPFEEF KIGYTGTRLAPRHVKGGIVLVDSVYTLKEDIWRYA | PumA1-ESV(without N-terminal met) |
| 11 | MARKKYSCDFETTTDPLDCRVWAYGYMEIGKDSNYKIGNSLDEFMEWVSK CNADLYFHNLREDGEFILIWLLQNGFKWSDKRKPEPMTENGVISRDNAVY RYDICYGYTNSGKKIHTVIYDSYKKLPYPVKVIAKAFNLTQLKGDIDYDA YRPVGHKITKEEYKYIYNDIKIIADALKIQFEQGLKKMTIGSDSLNGEKS IFGKKQFEKTFPVLDMLTDDFIRLSYKGGFTWLNPKFANIVINKGRVYDV NSMYPAIMYNELLPYGVPVREKGKYEKDDKYPLYIQQISCIFELKEGKIP MIQVKNEPLKFKGSEYLTSSKGYEVKLTLTNVELELFLENYKLNCVEYLG GYKFRGVRGLFKTFIDKWMNIKMNSEGAIRELAKLMLNNLYGKFATNPDV TGKYPELKEDGSLGFKMKPRELSEPVYTAMGSFITAYGRCMTVRTGQSCY DRFIYADTDSVHVAGNEDIPEIADKIDSKKLGYWDHEATFETGKYVRSKA YFLNLYAKKVVKDGEEIIKPCGEEEATTRKRKVACAGMPETLRNEVPFEE FKIGYTGTRLAPRHVKGGIVLVDSVYTLKEDIWRYA | PumA1-ESV(with N-terminal met) |
| 12 | $S(E/D)_n K_m (E/D)_p G$ | Solubility tag consensus sequence: S is serine, (E/D) is aspartate or glutamate, K is lysine, G is glycine, n is 5 or 6, m is 1 or 0, and p is an integer between 2 and 6 |
| 13 | SEDDEEKEEDG | SET tag |
| 14 | SEEDEEKEEDG | SET tag |
| 15 | SEEDEEEKEEG | SET tag |
| 16 | SEEEEDEEEEG | SET tag |
| 17 | SEEEEDEEEEEG | SET tag |
| 18 | SEEEEEEEEEG | SET tag |
| 19 | SSG | Linker |
| 20 | GGS | Linker |

-continued

| SEQUENCES | | |
|---|---|---|
| SEQ ID NO. | SEQUENCE | DESCRIPTION |
| 21 | GGSGG | Linker |
| 22 | GGGGG | Linker |
| 23 | GGAGG | Linker |
| 24 | GGGGSSS | Linker |
| 25 | GGGGAAA | Linker |
| 26 | GGGGS | Linker |

SEQUENCE LISTING

```
Sequence total quantity: 26
SEQ ID NO: 1            moltype = AA  length = 586
FEATURE                Location/Qualifiers
REGION                 1..586
                       note = PumA1 Protein including N-terminal met
source                 1..586
                       mol_type = protein
                       organism = Synthetic construct
SEQUENCE: 1
MARKKYSCDF ETTTDPLDCR VWAYGYMEIG KDSNYKIGNS LDEFMEWVSK CNADLYFHNL  60
RFDGEFILIW LLQNGFKWSD KRKPEPMTFN GVISRDNAVY RYDICYGYTN SGKKIHTVIY  120
DSYKKLPYPV KVIAKAFNLT QLKGDIDYDA YRPVGHKITK EEYKYIYNDI KIIADALKIQ  180
FEQGLKKMTI GSDSLNGFKS IFGKKQFEKT FPVLDMLTDD FIRLSYKGGF TWLNPKFANI  240
VINKGRVYDV NSMYPAIMYN ELLPYGVPVR FKGKYEKDDK YPLYIQQISC IFELKEGKIP  300
MIQVKNEPLK FKGSEYLTSS KGYEVKLTLT NVELELFLEN YKLNCVEYLG GYKFRGVRGL  360
FKTFIDKWMN IKMNSEGAIR ELAKLMLNNL YGKFATNPDV TGKYPELKED GSLGFKMKPR  420
ELSEPVYTAM GSFITAYGRC MTVRTGQSCY DRFIYADTDS VHVAGNEDIP EIADKIDSKK  480
LGYWDHEATF ETGKYVRSKA YFLNLYAKKV VKDGEEIIKP CGEEEATTRK RKVACAGMPE  540
TLRNIVPFEE FKIGYTGTRL APRHVKGGIV LVDAPYTLKE DIWRYA            586

SEQ ID NO: 2            moltype = AA  length = 585
FEATURE                Location/Qualifiers
REGION                 1..585
                       note = PumA1 Protein without N-terminal met
source                 1..585
                       mol_type = protein
                       organism = Synthetic construct
SEQUENCE: 2
ARKKYSCDFE TTTDPLDCRV WAYGYMEIGK DSNYKIGNSL DEFMEWVSKC NADLYFHNLR  60
FDGEFILIWL LQNGFKWSDK RKPEPMTFNG VISRDNAVYR YDICYGYTNS GKKIHTVIYD  120
SYKKLPYPVK VIAKAFNLTQ LKGDIDYDAY RPVGHKITKE EYKYIYNDIK IIADALKIQF  180
EQGLKKMTIG SDSLNGFKSI FGKKQFEKTF PVLDMLTDDF IRLSYKGGFT WLNPKFANIV  240
INKGRVYDVN SMYPAIMYNE LLPYGVPVRF KGKYEKDDKY PLYIQQISCI FELKEGKIPM  300
IQVKNEPLKF KGSEYLTSSK GYEVKLTLTN VELELFLENY KLNCVEYLGG YKFRGVRGLF  360
KTFIDKWMNI KMNSEGAIRE LAKLMLNNLG KFATNPDVT GKYPELKEDG SLGFKMKPRE  420
LSEPVYTAMG SFITAYGRCM TVRTGQSCYR FIYADTDSV HVAGNEDIPE IADKIDSKKL  480
GYWDHEATFE TGKYVRSKAY FLNLYAKKVV KDGEEIIKPC GEEEATTRKR KVACAGMPET  540
LRNIVPFEEF KIGYTGTRLA PRHVKGGIVL VDAPYTLKED IWRYA            585

SEQ ID NO: 3            moltype = AA  length = 696
FEATURE                Location/Qualifiers
REGION                 1..696
                       note = N-His/SUMO
source                 1..696
                       mol_type = protein
                       organism = Synthetic construct
SEQUENCE: 3
MGSSHHHHHH SSGSDSEVNQ EAKPEVKPEV KPETHINLKV SDGSSEIFFK IKKTTPLRRL  60
MEAFAKRQGK EMDSLRFLYD GIRIQADQTP EDLDMEDNDI IEAHREQIGG SARKKYSCDF  120
ETTTDPLDCR VWAYGYMEIG KDSNYKIGNS LDEFMEWVSK CNADLYFHNL RFDGEFILIW  180
LLQNGFKWSD KRKPEPMTFN GVISRDNAVY RYDICYGYTN SGKKIHTVIY DSYKKLPYPV  240
KVIAKAFNLT QLKGDIDYDA YRPVGHKITK EEYKYIYNDI KIIADALKIQ FEQGLKKMTI  300
GSDSLNGFKS IFGKKQFEKT FPVLDMLTDD FIRLSYKGGF TWLNPKFANI VINKGRVYDV  360
NSMYPAIMYN ELLPYGVPVR FKGKYEKDDK YPLYIQQISC IFELKEGKIP MIQVKNEPLK  420
FKGSEYLTSS KGYEVKLTLT NVELELFLEN YKLNCVEYLG GYKFRGVRGL FKTFIDKWMN  480
```

```
IKMNSEGAIR ELAKLMLNNL YGKFATNPDV TGKYPELKED GSLGFKMKPR ELSEPVYTAM   540
GSFITAYGRC MTVRTGQSCY DRFIYADTDS VHVAGNEDIP EIADKIDSKK LGYWDHEATF   600
ETGKYVRSKA YFLNLYAKKV VKDGEEIIKP CGEEEATTRK RKVACAGMPE TLRNIVPFEE   660
FKIGYTGTRL APRHVKGGIV LVDAPYTLKE DIWRYA                            696

SEQ ID NO: 4              moltype =    length =
SEQUENCE: 4
000

SEQ ID NO: 5              moltype = AA   length = 6
FEATURE                   Location/Qualifiers
REGION                    1..6
                          note = His-tag
source                    1..6
                          mol_type = protein
                          organism = Synthetic construct
SEQUENCE: 5
HHHHHH                                                              6

SEQ ID NO: 6              moltype = AA   length = 98
FEATURE                   Location/Qualifiers
REGION                    1..98
                          note = SUMO tag
source                    1..98
                          mol_type = protein
                          organism = Synthetic construct
SEQUENCE: 6
SDSEVNQEAK PEVKPEVKPE THINLKVSDG SSEIFFKIKK TTPLRRLMEA FAKRQGKEMD   60
SLRFLYDGIR IQADQTPEDL DMEDNDIIEA HREQIGGS                          98

SEQ ID NO: 7              moltype = AA   length = 606
FEATURE                   Location/Qualifiers
REGION                    1..606
                          note = C-HIS/SET
source                    1..606
                          mol_type = protein
                          organism = Synthetic construct
SEQUENCE: 7
MARKKYSCDF ETTTDPLDCR VWAYGYMEIG KDSNYKIGNS LDEFMEWVSK CNADLYFHNL   60
RFDGEFILIW LLQNGFKWSD KRKPEPMTFN GVISRDNAVY RYDICYGYTN SGKKIHTVIY   120
DSYKKLPYPV KVIAKAFNLT QLKGDIDYDA YRPVGHKITK EEYKYIYNDI KIIADALKIQ   180
FEQGLKKMTI GSDSLNGFKS IFGKKQFEKT FPVLDMLTDD FIRLSYKGGF TWLNPKFANI   240
VINKGRVYDV NSMYPAIMYN ELLPYGVPVR FKGKYEKDDK YPLYIQQISC IFELKEGKIP   300
MIQVKNEPLK FKGSEYLTSS KGYEVKLTLT NVELELFLEN YKLNCVEYLG GYKFRGVRGL   360
FKTFIDKWMN IKMNSEGAIR ELAKLMLNNL YGKFATNPDV TGKYPELKED GSLGFKMKPR   420
ELSEPVYTAM GSFITAYGRC MTVRTGQSCY DRFIYADTDS VHVAGNEDIP EIADKIDSKK   480
LGYWDHEATF ETGKYVRSKA YFLNLYAKKV VKDGEEIIKP CGEEEATTRK RKVACAGMPE   540
TLRNIVPFEE FKIGYTGTRL APRHVKGGIV LVDAPYTLKE DIWRYAGGSH HHHHHSEEDE   600
EKEEDG                                                             606

SEQ ID NO: 8              moltype = DNA   length = 1830
FEATURE                   Location/Qualifiers
misc_feature              1..1830
                          note = C-His/SET coding sequence
source                    1..1830
                          mol_type = other DNA
                          organism = Synthetic construct
SEQUENCE: 8
atggcgcgca aaaaatactc atgcgatttc gagaccacca ccgatccgct ggattgtcgc   60
gtgtgggcct acggctacat ggaaattggc aaagatagca attataaaat tggcaacagc   120
ctggatgagt tcatggagtg ggttagcaaa tgcaatgcgg atctgtattt tcacaacctg   180
cgtttcgatg gcgaatttat tctgatttgg ctgctgcaga acggctttaa atggagcgat   240
aaacgcaaac cggaaccgat gacctttaac ggcgtgattt cacgtgataa tgcggtgtat   300
cgttacgata tttgctatgg ctacaccaat agcggcaaaa aaattcacac cgtgatttac   360
gatagctata aaaaactgcc gtatccggtc aaagtgattg cgaaagcgtt caacctgacc   420
cagctgaaag cgatattga ttacgatgcg taccgcccgg tgggccataa aattaccaaa   480
gaagagtata aatacattta taatgatatc aaaatcattg ccgatgccct gaaaattcag   540
tttgaacagg gcctgaaaaa aatgaccatt ggaagcgatt cactgaacgg ttttaaatcg   600
atttttggca aaaaacagtt cgaaaaaacc ttcccggtgc tggatatgct gaccgatgat   660
ttcattcgcc tgtcgtataa aggcggcttc acctggctga cccgaaatt tgccaacatt   720
gtgattaaca aaggccgcgt gtatgatgtt aacagcatgt acccggcgat tatgtataac   780
gaactgctgc cgtatggcgt gccggtgcgc ttcaaaggca atatgaaaa agatgataaa   840
tatccgctgt atattcagca gattagctgc atttttgaac tgaaagaagg caaaattccg   900
atgattcagg ttaaaaacga accgctgaaa ttcaaaggca gcgaatatct gacctcaagc   960
aaaggttacg aagtgaaact gaccctgacc aatgtggagc tggaactgtt cctcgaaaac   1020
tacaaactga actgcgtgga atatctgggc ggctacaaaa ttcgcggcgt gcgcggcctg   1080
tttaaaacct ttattgataa atggatgaac attaaaatga acagcgaagg cgccattcgt   1140
gaactggcga aactgatgct gaataacctg tatggtaaat ttgcgaccaa cccggatgtg   1200
acgggcaaat atccggaact gaaagaagat ggcagcctgg gctttaaaat gaaaccgcgc   1260
```

-continued

```
gaactgtcag aaccggttta tacagcgatg ggcagcttta ttaccgcgta tggccgctgc   1320
atgaccgtgc gcaccggcca gtcttgctac gatcgcttta tttatgcgga taccgatagc   1380
gtgcatgtgg cgggcaatga agatattccg gaaattgcgg ataaaattga tagtaaaaaa   1440
ctgggctact gggatcatga agcgaccttt gaaaccggca aatatgtgcg cagcaaggcg   1500
tattttctga acttatacgc gaaaaaagtg gtgaaagatg gcgaagaaat tattaaaccg   1560
tgcggcgaag aagaagcaac cacccgcaaa cgtaaagttg cctgcgcggg catgccggaa   1620
accctgcgca acattgtgcc gttcgaagaa tttaaaattg gctatactgg tacccgcctg   1680
gcgccgcgcc atgttaaagg cggcattgtg ctggttgatg cgccttatac cctgaaagaa   1740
gacatttggc gctacgccgg tggctcacat caccaccatc atcattcaga gaggacgaa   1800
gagaaagaag aggacgggta atgaggttga                                     1830
```

```
SEQ ID NO: 9           moltype = DNA  length = 2088
FEATURE                Location/Qualifiers
misc_feature           1..2088
                       note = N-HIS/SUMO coding sequence
source                 1..2088
                       mol_type = other DNA
                       organism = Synthetic construct
SEQUENCE: 9
atgggttcta gccaccatca tcatcatcac tcttccggta gcgacagcga agtcaatcaa   60
gaggcgaagc ctgaagttaa gccagaagtc aaaccggaaa cgcacattaa cctgaaagtt   120
tcggatggct caagcgagat tttctttaag atcaagaaac ccacgccgtt gcgtcgcctg   180
atggaagcgt ttgccaaacg tcagggcaaa gaaatggatt ccctgcgctt cctgtatgac   240
ggcatccgta tccaggcaga tcaaacgccg gaagatctgg atatggaaga taacgacatt   300
attgaagcgc acagagagca aattggtggc agcgcgcgca aaaaatactc atgcgatttc   360
gagaccacca ccgatccgct ggattgtcgc gtgtgggcct acggctacat ggaaattggc   420
aaagatagca attataaaat tggcaacagc ctggatgagt tcatggagtg ggttagcaaa   480
tgcaatgcgg atctgtattt tcacaacctg cgtttcgatg gcgaatttat tctgatttgg   540
ctgctgcaga acggctttaa atggagcgat aaacgcaaac cggaaccgat gaccttaac   600
ggcgtgattt cacgtgataa tgcggtgtat cgttacgata tttgctatgg ctacaccaat   660
agcggcaaaa aaattcacac cgtgatttac gatagctata aaaaactgcc gtatccggtc   720
aaagtgattg cgaaagcgtt caacctgacc cagctgaaag cgatattgaa ttacgatgcg   780
taccgcccgg tgggccataa aattaccaaa gaagagtata aatacattta taatgatatc   840
aaaatcattg ccgatgccct gaaaattcag tttgaacagg gcctgaaaaa aatgaccatt   900
ggaagcgatt cactgaacgg ttttaaatcg atttttggca aaaaacagtt cgaaaaaacc   960
ttcccggtgc tggatatgct gaccgatgat ttcattcgcc tgtcgtataa aggcggcttc   1020
acctggctga acccgaaatt tgccaacatt gtgattaaca aaggccgcgt gtatgatgtt   1080
aacagcatgt acccggcgat tatgtataac gaactgctgc cgtatggcgt gccggtcgcg   1140
ttcaaaggca aatatgaaaa agatgataaa tatccgctgt atattcagca gattagctgc   1200
atttttgaac tgaaagaagg caaaattccg atgattcagg ttaaaaacga accgctgaaa   1260
ttcaaaggca gcgaatatct gacctcaagc aaaggttacg aagtgaaact gaccctgacc   1320
aatgtgggag ctggaactgtt cctcgaaaac tacaaactga actcgtgga atatctgggc   1380
ggctacaaat ttcgcggcgt gcgcggcctg tttaaaacct ttattgataa atggatgaac   1440
attaaaatga cagcgaagg cgccattcgt gaactggcga aactgatgct gaataacctg   1500
tatggtaaat ttgcgaccaa cccggatgtg acgggcaaat atccggaact gaaagaagat   1560
ggcagcctgg gctttaaaat gaaaccgcgc gaactgtcag aaccggttta tacagcgatg   1620
ggcagcttta ttaccgcgta tggccgctgc atgaccgtgc gcaccggcca gtcttgctac   1680
gatcgcttta tttatgcgga taccgatagc gtgcatgtgg cgggcaatga agatattccg   1740
gaaattgcgg ataaaattga tagtaaaaaa ctgggctact gggatcatga agcgaccttt   1800
gaaaccggca aatatgtgcg cagcaaggcg tattttctga acttatacgc gaaaaaagtg   1860
gtgaaagatg gcgaagaaat tattaaaccg tgcggcgaag aagaagcaac cacccgcaaa   1920
cgtaaagttg cctgcgcggg catgccggaa accctgcgca acattgtgcc gttcgaagaa   1980
tttaaaattg gctatactgg tacccgcctg gcgccgcgcc atgttaaagg cggcattgtg   2040
ctggttgatg cgccttatac cctgaaagaa gacatttggc gctacgcc                2088
```

```
SEQ ID NO: 10          moltype = AA  length = 585
FEATURE                Location/Qualifiers
REGION                 1..585
                       note = PumA1-ESV(without N-terminal met)
source                 1..585
                       mol_type = protein
                       organism = Synthetic construct
SEQUENCE: 10
ARKKYSCDFE TTTDPLDCRV WAYGYMEIGK DSNYKIGNSL DEFMEWVSKC NADLYFHNLR   60
FDGEFILIWL LQNGFKWSDK RKPEPMTFNG VISRDNAVYR YDICYGYTNS GKKIHTVIYD   120
SYKKLPYPVK VIAKAFNLTQ LKGDIDYDAY RPVGHKITKE EYKYIYNDIK IIADALKIQF   180
EQGLKKMTIG SDSLNGFKSI FGKKQFEKTF PVLDMLTDDF IRLSYKGGFT WLNPKFANIV   240
INKGRVYDVN SMYPAIMYNE LLPYGVPVRF KGKYEKDDKY PLYIQQISCI FELKEGKIPM   300
IQVKNEPLKF KGSEYLTSSK GYEVKLTLTN VELELFLENY KLNCVEYLGG YKFRGVRGLF   360
KTFIDKWMNI KMNSEGAIRE LAKLMLNNLY GKFATNPDVT GKYPELKEDG SLGFKMKPRE   420
LSEPVYTAMG SFITAYGRCM TVRTGQSCYD RFIYADTDSV HVAGNEDIPE IADKIDSKKL   480
GYWDHEATFE TGKYVRSKAY FLNLYAKKVV KDGEEIIKPC GEEEATTRKR KVACAGMPET   540
LRNEVPFEEF KIGYTGTRLA PRHVKGGIVL VDSVYTLKED IWRYA                    585
```

```
SEQ ID NO: 11          moltype = AA  length = 586
FEATURE                Location/Qualifiers
REGION                 1..586
                       note = PumA1-ESV(with N-terminal met)
source                 1..586
```

-continued

```
                              mol_type = protein
                              organism = Synthetic construct
SEQUENCE: 11
MARKKYSCDF ETTTDPLDCR VWAYGYMEIG KDSNYKIGNS LDEFMEWVSK CNADLYFHNL    60
RFDGEFILIW LLQNGFKWSD KRKPEPMTFN GVISRDNAVY RYDICYGYTN SGKKIHTVIY   120
DSYKKLPYPV KVIAKAFNLT QLKGDIDYDA YRPVGHKITK EEYKYIYNDI KIIADALKIQ   180
FEQGLKKMTI GSDSLNGFKS IFGKKQFEKT FPVLDMLTDD FIRLSYKGGF TWLNPKFANI   240
VINKGRVYDV NSMYPAIMYN ELLPYGVPVR FKGKYEKDDK YPLYIQQISC IFELKEGKIP   300
MIQVKNEPLK FKGSEYLTSS KGYEVKLTLT NVELELFLEN YKLNCVEYLG GYKFRGVRGL   360
FKTFIDKWMN IKMNSEGAIR ELAKLMLNNL YGKFATNPDV TGKYPELKED GSLGFKMKPR   420
ELSEPVYTAM GSFITAYGRC MTVRTGQSCY DRFIYADTDS VHVAGNEDIP EIADKIDSKK   480
LGYWDHEATF ETGKYVRSKA YFLNLYAKKV VKDGEEIIKP CGEEEATTRK RKVACAGMPE   540
TLRNEVPFEE FKIGYTGTRL APRHVKGGIV LVDSVYTLKE DIWRYA                  586

SEQ ID NO: 12         moltype =   length =
SEQUENCE: 12
000

SEQ ID NO: 13         moltype = AA   length = 11
FEATURE               Location/Qualifiers
REGION                1..11
                      note = SET tag
source                1..11
                      mol_type = protein
                      organism = Synthetic construct
SEQUENCE: 13
SEDDEEKEED G                                                         11

SEQ ID NO: 14         moltype = AA   length = 11
FEATURE               Location/Qualifiers
REGION                1..11
                      note = SET tag
source                1..11
                      mol_type = protein
                      organism = Synthetic construct
SEQUENCE: 14
SEEDEEKEED G                                                         11

SEQ ID NO: 15         moltype = AA   length = 11
FEATURE               Location/Qualifiers
REGION                1..11
                      note = SET tag
source                1..11
                      mol_type = protein
                      organism = Synthetic construct
SEQUENCE: 15
SEEDEEKEE G                                                          11

SEQ ID NO: 16         moltype = AA   length = 11
FEATURE               Location/Qualifiers
REGION                1..11
                      note = SET tag
source                1..11
                      mol_type = protein
                      organism = Synthetic construct
SEQUENCE: 16
SEEEEDEEEE G                                                         11

SEQ ID NO: 17         moltype = AA   length = 12
FEATURE               Location/Qualifiers
REGION                1..12
                      note = SET tag
source                1..12
                      mol_type = protein
                      organism = Synthetic construct
SEQUENCE: 17
SEEEEDEEEE EG                                                        12

SEQ ID NO: 18         moltype = AA   length = 11
FEATURE               Location/Qualifiers
REGION                1..11
                      note = SET tag
source                1..11
                      mol_type = protein
                      organism = Synthetic construct
SEQUENCE: 18
SEEEEEEEEE G                                                         11

SEQ ID NO: 19         moltype =   length =
```

-continued

```
SEQUENCE: 19
000

SEQ ID NO: 20          moltype =   length =
SEQUENCE: 20
000

SEQ ID NO: 21          moltype = AA  length = 5
FEATURE                Location/Qualifiers
REGION                 1..5
                       note = Linker
source                 1..5
                       mol_type = protein
                       organism = Synthetic construct
SEQUENCE: 21
GGSGG                                                            5

SEQ ID NO: 22          moltype = AA  length = 5
FEATURE                Location/Qualifiers
REGION                 1..5
                       note = Linker
source                 1..5
                       mol_type = protein
                       organism = Synthetic construct
SEQUENCE: 22
GGGGG                                                            5

SEQ ID NO: 23          moltype = AA  length = 5
FEATURE                Location/Qualifiers
REGION                 1..5
                       note = Linker
source                 1..5
                       mol_type = protein
                       organism = Synthetic construct
SEQUENCE: 23
GGAGG                                                            5

SEQ ID NO: 24          moltype = AA  length = 7
FEATURE                Location/Qualifiers
REGION                 1..7
                       note = Linker
source                 1..7
                       mol_type = protein
                       organism = Synthetic construct
SEQUENCE: 24
GGGGSSS                                                          7

SEQ ID NO: 25          moltype = AA  length = 7
FEATURE                Location/Qualifiers
REGION                 1..7
                       note = Linker
source                 1..7
                       mol_type = protein
                       organism = Synthetic construct
SEQUENCE: 25
GGGGAAA                                                          7

SEQ ID NO: 26          moltype = AA  length = 5
FEATURE                Location/Qualifiers
REGION                 1..5
                       note = Linker
source                 1..5
                       mol_type = protein
                       organism = Synthetic construct
SEQUENCE: 26
GGGGS                                                            5
```

The invention claimed is:

1. A method of performing a rolling circle amplification (RCA), the method comprising contacting a biological sample containing a circular DNA to be amplified with a recombinant polymerase comprising an amino acid sequence having at least 99% sequence identity to the sequence set forth in SEQ ID NO:2, wherein the circular DNA is amplified by rolling circle amplification (RCA) using the recombinant polymerase.

2. The method of claim 1, wherein the recombinant polymerase and the biological sample are incubated at a temperature of between 35° C. and 45° C.

3. The method of claim 1, wherein the recombinant polymerase comprises the amino acid sequence of SEQ ID NO:10.

4. The method of claim 3, wherein the method results in an increased signal intensity for a detected RCA product compared to a reference RCA product produced using a reference polymerase, wherein the reference polymerase is a wild-type Phi29 or a wild-type PumA1 polymerase.

5. The method of claim 1, wherein the method comprises detecting or analyzing an RCA product generated by the RCA using the recombinant polymerase.

6. The method of claim 5, wherein the RCA product is detected at a location in the biological sample.

7. The method of claim 5, wherein the detecting comprises:

contacting the biological sample with one or more detectably-labeled probes that directly or indirectly bind to one or more barcode sequences or complements thereof in the RCA product, and detecting signals associated with the one or more detectably-labeled probes.

8. The method of claim 5, wherein the detecting comprises:

contacting the biological sample with one or more intermediate probes that directly or indirectly bind to one or more barcode sequences or complements thereof in the RCA product, wherein the one or more intermediate probes are detectable using one or more detectably-labeled probes, and detecting signals associated with the one or more detectably-labeled probes.

9. The method of claim 1, wherein the recombinant polymerase has strand displacing activity.

10. The method of claim 1, wherein the recombinant polymerase produces at least 10% more RCA products than a reference Phi29 polymerase under the same reaction conditions.

11. The method of claim 1, wherein the method comprises contacting the biological sample with a buffer, wherein the buffer:

(i) has a pH of about 8.5, (ii) comprises between about 5 mM and about 10 mM $MgCl_2$, (iii) comprises between about 0.1 mM and about 0.2 mM dNTPs, (iv) comprises between about 1 mM and about 4 mM DTT, (v) comprises about 0.2 mg/mL BSA, and/or (vi) comprises about 10 mM $NH_4SO_4$.

12. The method of claim 1, wherein the recombinant polymerase further comprises a heterologous sequence.

13. The method of claim 12, wherein the heterologous sequence comprises an affinity tag and the affinity tag is a His-tag.

14. The method of claim 12, wherein the heterologous sequence comprises a small ubiquitin modified (SUMO) tag or a solubility-enhancement tag (SET).

15. The method of claim 1, further comprising contacting the biological sample with a primer that hybridizes to the nucleic acid circular DNA.

16. The method of claim 1, wherein the biological sample is a cell or tissue sample.

17. The method of claim 1, wherein the recombinant polymerase comprises one or more amino acid substitutions at positions selected from among 545, 574 and 575, corresponding to the positions of the sequence set forth in SEQ ID NO:1.

18. The method of claim 1, wherein the recombinant polymerase comprises I545E and A574S amino acid substitutions, corresponding to the positions of the sequence set forth in SEQ ID NO:1.

19. The method of claim 1, wherein the recombinant polymerase comprises I545E and P575V amino acid substitutions, corresponding to the positions of the sequence set forth in SEQ ID NO:1.

20. The method of claim 1, wherein the recombinant polymerase comprises amino acid substitutions I545E, A574S, and P575V in a sequence at least 90% identical to SEQ ID NO:1, wherein the amino acid numbering corresponds to the positions of the sequence set forth in SEQ ID NO:1.

* * * * *